United States Patent
Hofer et al.

(10) Patent No.: US 9,944,685 B2
(45) Date of Patent: Apr. 17, 2018

(54) COMPLEMENT SPLIT PRODUCT C4D FOR THE TREATMENT OF INFLAMMATORY CONDITIONS

(71) Applicant: Medizinische Universität Wien, Vienna (AT)

(72) Inventors: Johannes Hofer, Vienna (AT); Peter Steinberger, Vienna (AT); Gerhard Zlabinger, Vienna (AT); Georg Böhmig, Vienna (AT); Florian Forster, Ösmo (SE); Judith Leitner, Vienna (AT); Markus Wahrmann, Vienna (AT); Margarethe Merio, Vienna (AT); Johannes Kovarik, Vienna (AT); Markus Hölzl, New York, NY (US); David E. Isenman, Toronto (CA)

(73) Assignee: Medizinische Universität Wien, Vienna (AT)

( * ) Notice: Subject to any disclaimer, the term of this patent is extended or adjusted under 35 U.S.C. 154(b) by 0 days.

(21) Appl. No.: 14/412,449

(22) PCT Filed: Jul. 2, 2013

(86) PCT No.: PCT/EP2013/063973
§ 371 (c)(1),
(2) Date: Jan. 1, 2015

(87) PCT Pub. No.: WO2014/006063
PCT Pub. Date: Jan. 9, 2014

(65) Prior Publication Data
US 2015/0191520 A1 Jul. 9, 2015

(30) Foreign Application Priority Data

Jul. 2, 2012 (EP) .................................... 12174644

(51) Int. Cl.
*A61K 38/16* (2006.01)
*C07K 14/47* (2006.01)
*G01N 33/50* (2006.01)

(52) U.S. Cl.
CPC ............ *C07K 14/472* (2013.01); *A61K 38/16* (2013.01); *G01N 33/5041* (2013.01); *G01N 2333/4716* (2013.01); *G01N 2333/705* (2013.01); *G01N 2500/02* (2013.01); *G01N 2500/10* (2013.01)

(58) Field of Classification Search
None
See application file for complete search history.

(56) References Cited

U.S. PATENT DOCUMENTS

2003/0181362 A1  9/2003  Inal
2010/0233752 A1  9/2010  Ahearn et al.

FOREIGN PATENT DOCUMENTS

WO  2004030615     11/2008
WO  2009041026 A1  4/2009
WO  2010091183 A2  8/2010

OTHER PUBLICATIONS

Number of atoms in Hmolpedia (2016) two pages.*
Yaturu, Insulin therapies: Current and future trends at dawn, World J Diabetes. Feb. 15, 2013;4(1):1-7.*
Van Den Elsen J M H et al, "X-ray Crystal Structure of the C4d Fragment of Human Complement Component C4", Journal of Molecular Biology, Academic Press, United Kingdom vo 1. 322, No. 5, Oct. 4, 2002 (Oct. 4, 2002), pp. 1103-1115, XP004449797, the whole document.
Written Opinion of the International Searching Authority in parent International application No. PCT/EP2013/063973.
Z Chen et al: "Complement C4 inhibits systemic autoimmunity through a mechanism independent of complement receptors CRI and CR2", The Journal of experimental medicine Nov. 6, 2000 (Nov. 6, 2000), pp. 1339-1352, XP055085697, abstract, p. 1339 col. 1, p. 1340 cols. 4,6, p. 1344 col. 3, p. 1348 col. 2, p. 1349 col. 4.
Office of Action dated Nov. 23, 2016 received in corresponding European Application, Application No. 13 747 983.8.

* cited by examiner

Primary Examiner — Thomas S Heard
(74) Attorney, Agent, or Firm — Michele M. Wales; InHouse Patent Counsel, LLC

(57) ABSTRACT

The present invention relates to a pharmaceutical composition comprising complement split product C4d for use in treating an inflammatory condition, such as graft rejection, graft versus host disease, an autoimmune disease or atopy. The C4d to be used may be a multimer. Accordingly, also C4d multimers and their use in medicine, like the treatment of inflammatory conditions, is provided. Furthermore, the present invention provides a protein complex comprising C4d interacting with its ILT4 receptor. This protein complex may be used in screening methods Also antibodies specifically binding to the C4d multimer or the C4d/ILT4-protein complex are subject of the present invention.

Figure 1:
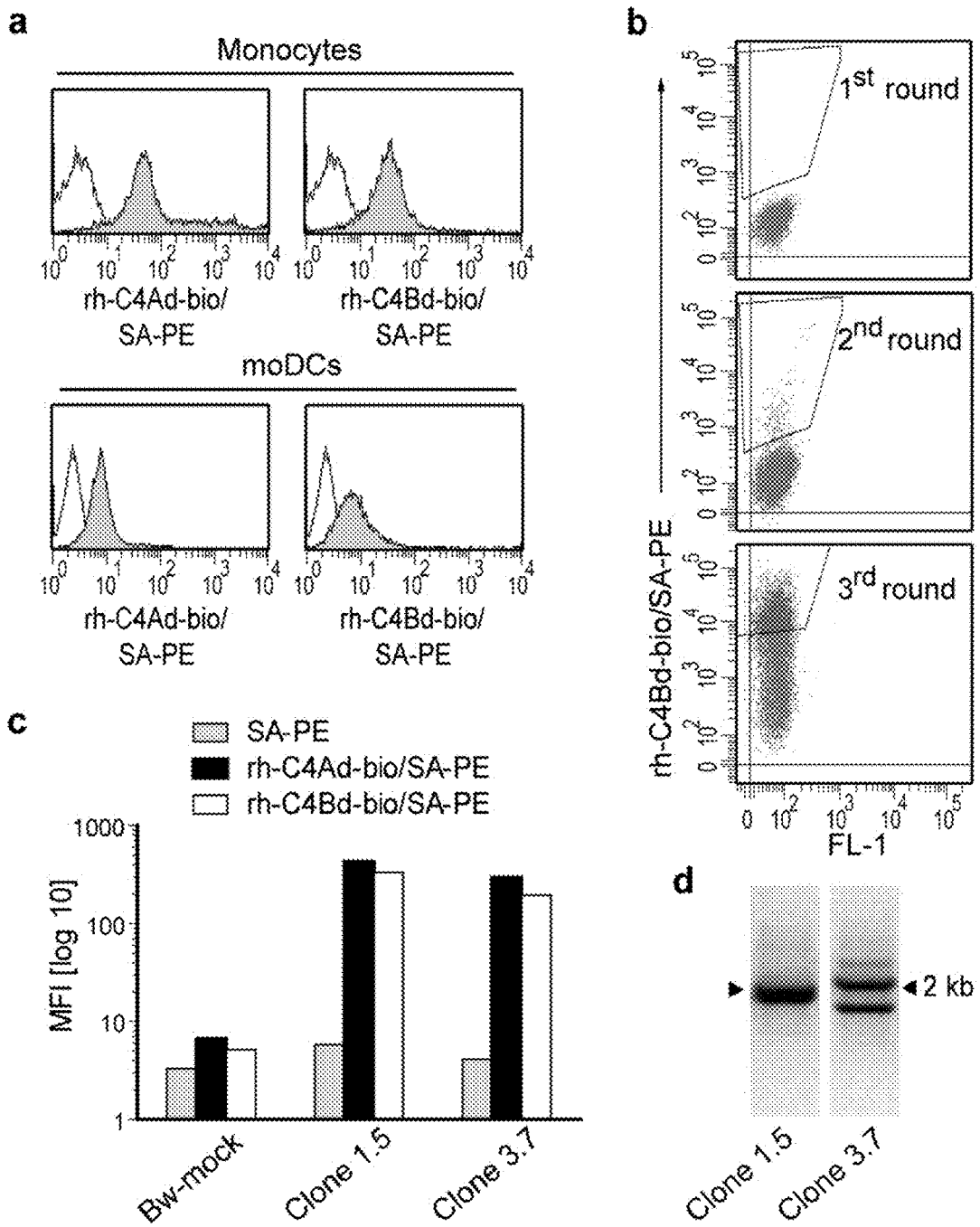
Figure 1:
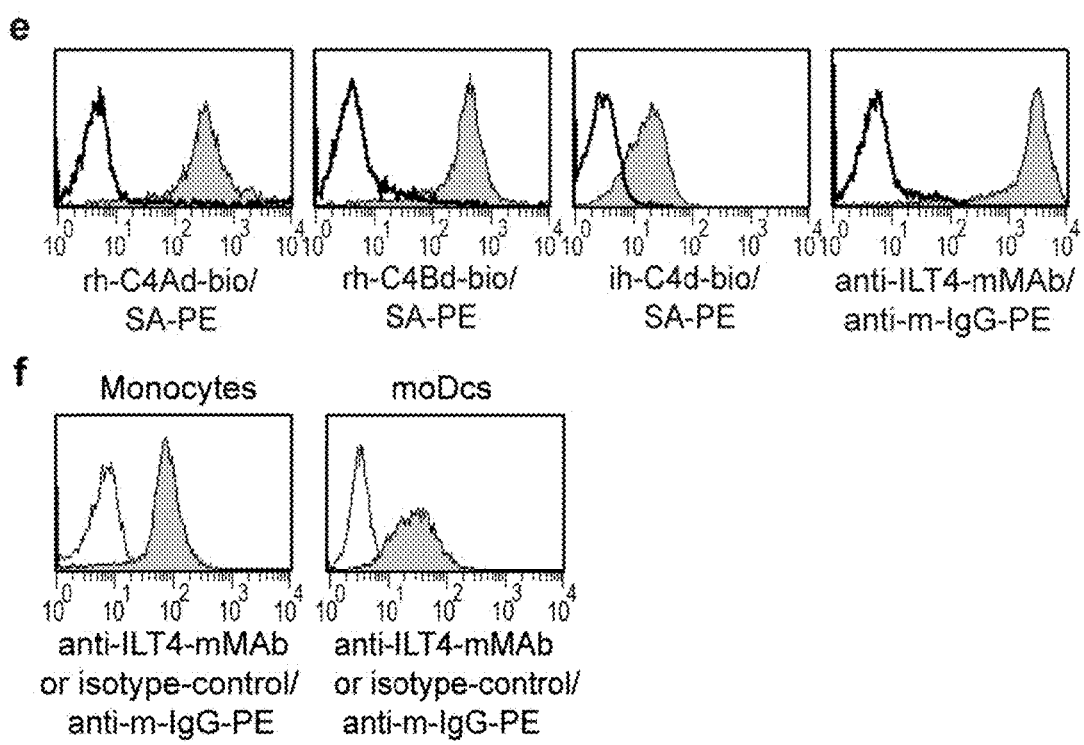

31 Claims, 12 Drawing Sheets d.

COMPLEMENT SPLIT PRODUCT C4D FOR THE TREATMENT OF INFLAMMATORY CONDITIONS

The present invention relates to a pharmaceutical composition comprising complement split product C4d for use in treating an inflammatory condition, such as graft rejection, graft versus host disease, autoimmune disease, or atopy. The C4d to be used may be a multimer. Accordingly, also C4d multimers and their use in medicine, like the treatment of inflammatory conditions, are provided. Furthermore, the present invention relates to a protein complex comprising C4d interacting with its ILT4 receptor. This protein complex may be used in screening methods, like drug screening methods. Also antibodies specifically binding to the C4d multimer or the C4d/ILT4-protein complex are subject of the present invention.

In addition to defence against invading pathogens the complement system crucially contributes to host homeostasis by clearing circulating immune complexes (ICs) from blood. The complement system as a potentially harmful effector system is tightly regulated leading to the generation of complement split products (CSPs) such as C4d. Complement component C4 plays a key role in both the classical and the lectin pathways of complement activation. C4 is cleaved by activated C1s or MASP2. Activation of C1s from its zymogen form is a consequence of the binding of the C1q moiety of the C1qr$_2$s$_2$ complex to the Fc arrays of ICs, or directly to apoptotic cellular material or some pathogen surfaces. Similarly, zymogen MASP2 exists in complex with mannose binding lectin (MBL) or ficolins and becomes activated when MBL or ficolin bind to terminal mannoses or acetylated entities on invading pathogens. A portion of the C1s- or MASP2-cleaved C4 covalently attaches to target antigen through its highly reactive intrinsic thioester bond. This is pivotal for the generation of the C3 (C4b2a) and the C5 (C4b2a3b) convertases of the classical and lectin pathways of complement activation[8-13]. These convertases mediate opsonisation and formation of the terminal lytic complex required for the elimination of "non-self"/"dangerous" target cells. By contrast, "self"/"non-dangerous" tissues are protected from detrimental complement activation by membrane-bound and soluble regulator proteins, which act by disrupting convertases either through their decay-dissociation activities or through their factor I cofactor activities that lead to the enzymatic cleavage of C4b and C3b. This process yields the complement degradation products C4d, iC3b, C3dg and C3d, all of which remain covalently bound to the target surface. Except for C4d these molecules are known to act as opsonins mediating specific interaction between target structures and complement receptors. Although evidence of C4d-deposition on lymphocytes and erythrocytes correlates with SLE-activity[1,2] and its deposition in renal allografts is an established marker of antibody-mediated rejection (AMR)[3,14,15], C4d itself is an orphan ligand with no attributed function per se.

Thus, the technical problem underlying the present invention is the provision of a medical application of C4d in the treatment of a disease or disorder.

The technical problem is solved by provision of the embodiments characterized in the claims.

Accordingly, the present invention relates to a pharmaceutical composition comprising complement split product C4d for use in treating an inflammatory condition.

The present invention solves the above identified technical problem since, as documented herein below and in the appended examples, it was surprisingly found that C4d is capable of triggering an anti-inflammatory response (likewise C4d is capable of down-regulating a pro-inflammatory response) and can, therefore, be used in the treatment of an inflammatory condition. Moreover, it was found that C4d binds to ILT4. This is the first identification of a medical use of C4d and the first identification of a receptor for C4d.

Figure 4:
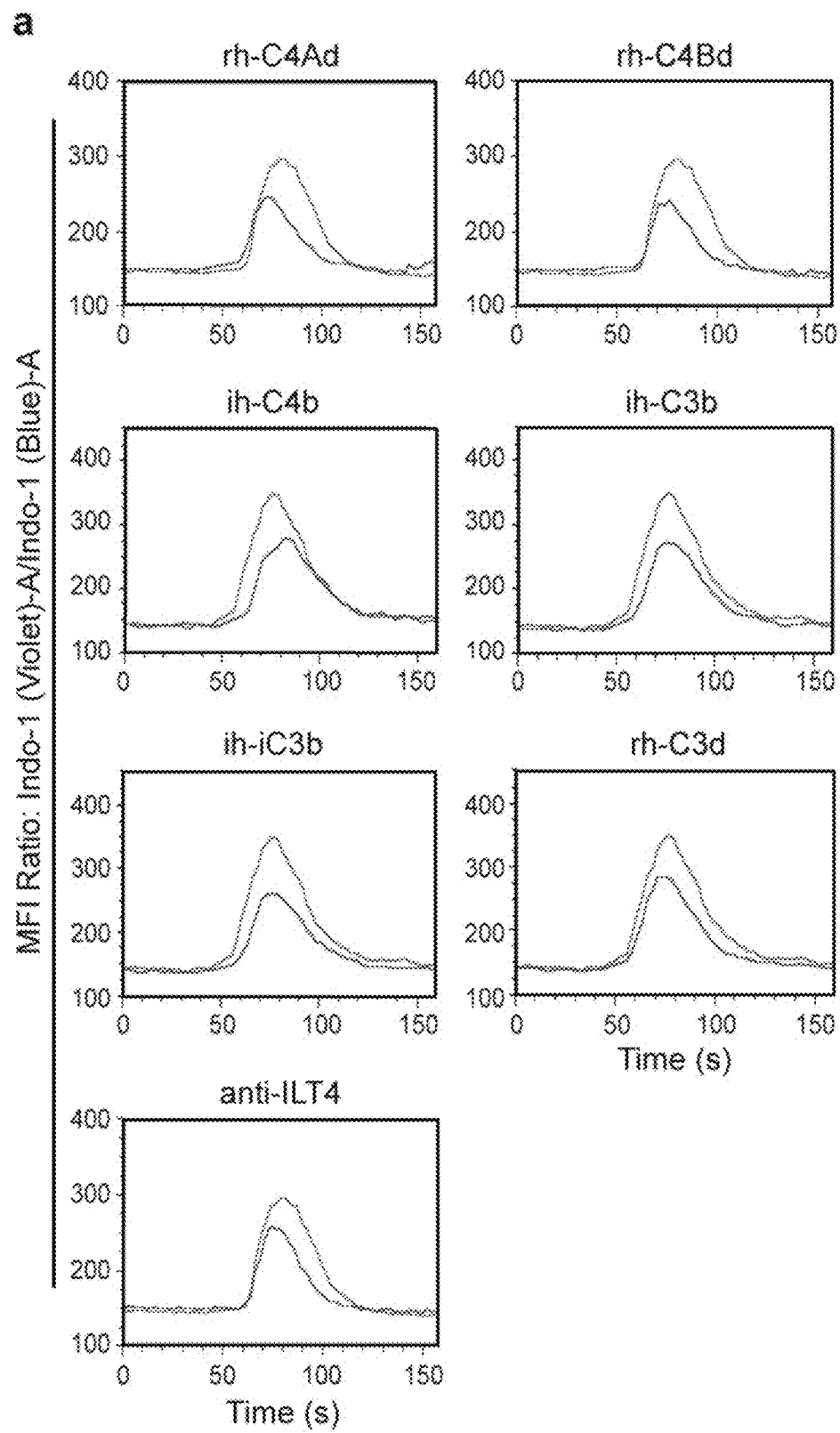
Figure 4:
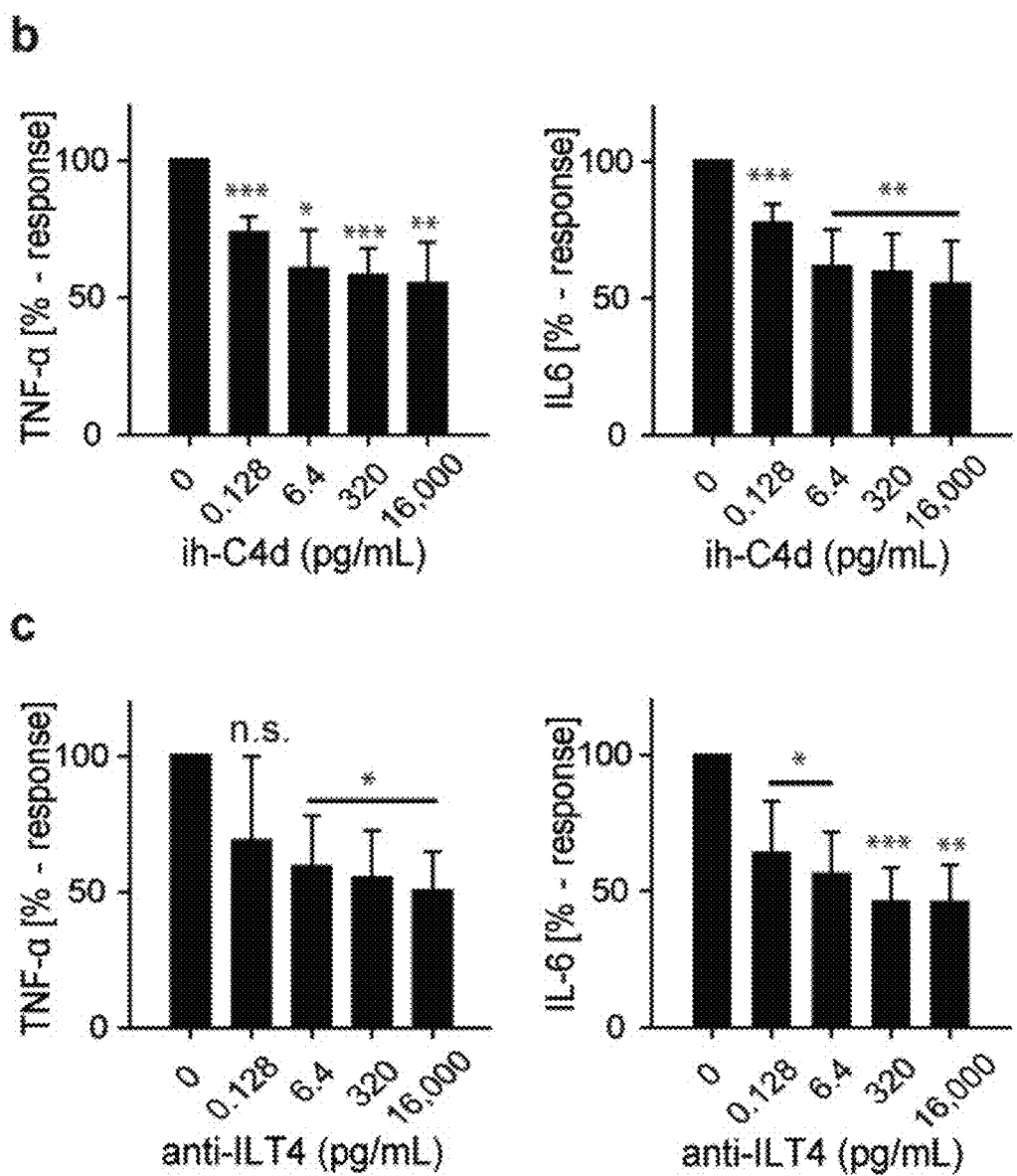

FIG. 4 shows that C4d is capable of decreasing TNF-α and IL-6 production in monocytes. TNFα and IL6 are pro-inflammatory cytokines and known markers for inflammatory conditions. Thus, the appended data show that C4d is, by decreasing TNF-α and IL-6 production, capable of downregulating a pro-inflammatory response. Therefore, the therapeutic use of C4d is beneficial in the treatment of an inflammatory condition, such as graft rejection, graft versus host disease, an autoimmune disease, or atopy.

The finding that C4d is capable of downregulating a pro-inflammatory response is unexpected, since C4d is regarded in the art as a mere by-product of C4 processing during complement activation, which may, at most, be useful as marker for antibody mediated rejection or antibody-mediated autoimmune disorders; for a review see Murata (2009), Transplanation Reviews 23, 139-150 or Botto (2009), Mol Immunology 46, 2774-2783. The use of C4d as marker for inflammatory diseases is also described in Haas (2009), J Am Soc Nephrol 20, 197-204, US-A1 2005/0042602 and U.S. Pat. No. 7,361,517. JP-A 02293665 discloses the use of C4d as marker for renal disease in urine and WO 2007/118983 discloses that C4d can be used to analyze the risk of transplant rejection. However, none of these documents attributes a biological function to C4d and, moreover, up to date no receptors binding to C4d have been identified. Therefore, the present finding that C4d binds to the receptor ILT4 and triggers an anti-inflammatory response (or likewise down-regulates a pro-inflammatory response) was unexpected. The above is in line with the conventional view that C4d is a mere by-product of complement activation, which has no biological activity of its own; see below.

C4 is activated by enzymatic cleavage, whereby its split products C4b and iC4b are formed. Together with C2-split product C2a, C4b forms the C3 convertase of the classical and the lectin pathway of complement activation (C4b2a), which contribute to the stimulation of an inflammatory response (reflected e.g. in the production of proinflammatory cytokines, such as TNF-α, IL-6, IL-1, and IL-8). Accordingly, C4b and other complement compounds involved in the complement activation have been proposed in the art for stimulating the immune system. For example, WO 96/17625 describes the C3d-CD21 interaction and proposes the use of C3d for the modulation of the immune response. WO 02/33081 describes the use of C3d for immunization and for stimulating the immune response. In the same vein, WO 02/10199 describes C3b/C4b peptides and proposes their use in medicine. Also agonists thereof for the treatment of inflammatory diseases are described therein. Vice versa, the prior art also described the use of antagonists of C3b/C4b for the inhibition of the immune response. For example, WO 98/45430 describes that soluble complement receptor sCR1 binds to and antagonizes C4b and C3b and can therefore be used for inhibiting the immune response. WO 95/08343 proposes the use of short or modified analogues of complement proteins, like C4b. These analogues are said to have decreased activity compared to their natural forms; therefore, the use of such analogues (e.g. as competitive inhibitors) is said to be useful for complement inhibition, and hence, for the treatment of autoimmune diseases or for preventing xenograft rejection. Also WO 02/10388 describes C3d/C4b for stimulating the immune response and, vice versa, the use of antagonists for suppression of the immune system.

Thus, the above prior art documents show that compounds of the complement system, especially C3d and C4b, have been disclosed in the art for stimulating the immune response (or vice versa, antagonists of C3d or C4b for inhibiting the immune response). The prior art has, however, not proposed that the split product C4d derived from C4b (which is, in turn, derived from C4) could have any potential effect on the modulation of the immune response. The following relates more specifically to the split product C4d derived from C4b.

The split product C4b, which is covalently bound to cells, can be further cleaved into an enzymatically inactive form, termed "inactive C4b" or "iC4b" (it is termed "inactive", because it not able to function as part of the C3 convertase). "iC4b" can be further cleaved, which results in the surface-bound C4d. C4d was identified in the art as a marker for antibody-mediated rejection (AMR), especially in renal and cardiac transplants. C4d is known to be a reliable marker for complement activation because it covalently binds to tissue close to the site of activation, and the covalent bond does not break spontaneously. However, Murata (loc. cit.) notes that no biological function has been attributed to C4d and no receptors have been identified.

In the present invention it has been surprisingly found that C4d is not merely an end-product or by-product of the complement activation. To the contrary, for the first time a receptor of C4d has been identified demonstrating that C4d has indeed a biological activity: it is shown herein that C4d triggers an anti-inflammatory response (or likewise down-regulates a pro-inflammatory response).

Without being bound by theory, it is believed that the binding of C4d to ILT4 (as shown herein) is beneficial in downregulating a pro-inflammatory response. As illustrated below, ILT4 is known to be involved in the modulation of the immune response (especially inhibition of the immune response). Also for this reason, it may be that C4d down-regulates a pro-inflammatory response upon binding to and activating ILT4. This is described in more detail in the following.

The ILT4 receptor is known in the art to be involved in the modulation of the immune response. For example, PIR-B deficient mice (PIR-B is the murine ortholog of ILT-4) showed excessive autoantibody production and autoimmunity; see Kubo (2009) J Exp Med 206, 1971-1982. Ristich (2007) reports that interaction between ILT4-receptor and HLA-G (a nonclassical major histocompatibility complex (MHC) molecule) may prevent transplant rejection; see Ristich (2007), Human Immunology 68, 264-271. Similarly, WO 2009/100135 discloses that HLA-G binds to ILT-4 and thereby induces the ILT-4 mediated inhibitory signaling. According to WO 2009/100135 microparticles comprising an HLA-G dimer can therefore be used to treat inflammatory diseases or disorders. Thus, it was known in the art that triggering of ILT-4 may induce an anti-inflammatory response. However, none of these publications propose that C4d might bind to ILT4, let alone that C4d might induce an anti-inflammatory response (or likewise that C4d might down-regulate a pro-inflammatory response) by potentially binding to ILT4.

Deposition of C4d on blood cells has been associated with disease activity in autoimmune syndromes like systemic lupus erythematosus (SLE)[1,2], and presence of C4d in renal[3] allografts is an established marker of antibody-mediated rejection. However, to date no physiologic function has been ascribed to C4d. Herein, the identification of Immunoglobulin-Like Transcript 4 (ILT4) and its close relative ILT5 antigenic variant 2 (ILT5v2) as novel cellular receptors for C4d is disclosed. Furthermore, it is shown that ILT4 and ILT5v2 also bind CSPs C3d, C4b, C3b and iC3b. It is demonstrated that interaction of these CSPs with ILT4, a well-known negative immune regulator[4-7], confers inhibitory activity on monocytes activated ex-vivo. While C4b, C3b, iC3b and C3d are known to mediate a variety of effector functions via established complement receptors, e.g. enhanced clearance of CSP-opsonised particles, immune cell activation and the induction of humoral immune responses, herein evidence for a novel regulatory activity of these molecules through interaction with ILT4 is provided. Thus, the herein presented findings reveal a thus far unknown regulatory mechanism that might contribute to host homeostatic regulation and the maintenance of self-tolerance. As mentioned, C4b, C3b, iC3b and C3d bind to various receptors which are primarily involved in complement activation. In contrast to C4b, C3b, iC3b and C3d, C4d specifically interacts with ILT4 and ILT5v2, but not with conventional complement receptors. Thus, C4d is the only split product derived from C4 during complement activation that specifically binds to ILT4. Without being bound by theory, it is shown that the binding of C4d to ILT4 downregulates a pro-inflammatory stimulus.

These findings provide the basis for the herein provided novel therapies for the treatment of a variety of inflammatory conditions such as autoimmune diseases, allograft rejection or atopic diseases. As described further below, the herein provided medical use of C4d can be further assessed in pre-clinical in-vivo models, since it has been found that C4d, C3b and iC3b also interact with PIR-B, the murine ortholog of ILT4. Thus, the medical use of C4d could be confirmed in C4d transgenic animals. As pointed out above, nothing in the prior art provided a hint that C4d might be useful in the treatment of inflammatory conditions.

As mentioned, the present invention relates to a pharmaceutical composition comprising complement split product C4d for use in treating an inflammatory condition. The terms "inflammatory condition", "disorder associated with immune-mediated inflammation" or "conditionassociated with an excessive immune response" are synonyms and are accordingly used interchangeably herein.

The term "C4d" used herein refers primarily to (a) polypeptide(s) having a biological activity specific for C4d polypeptides like the polypeptides shown in SEQ ID NO:2 (isoform C4d-A, also known as C4Ad) (UniProtKB POCOL4, "C4Ad": AA 957-1336) or SEQ ID NO: 4 (isoform C4d-B, also known as C4Bd) (UniProtKB POCOL5, "C4Bd": AA 957-1336). The terms "complement split product C4d-A", "C4d-A", "complement split product C4Ad" and "C4Ad" and the like as well as grammatical variants thereof can be used interchangeably herein. The terms "complement split product C4d-B", "C4d-B", "complement split product C4Bd" and "C4Bd" and the like as well as grammatical variants thereof can be used interchangeably herein. The polypeptides to be used in accordance with the present invention are, for example, capable of triggering/inducing/stimulating an anti-inflammatory response (i.e. triggering/inducing/stimulating an anti-inflammatory response is an exemplary biological activity of the "C4d" polypeptides to be used herein). Preferably, the polypeptides to be used in accordance with the present invention are capable of downregulating a pro-inflammatory response (i.e. downregulating a pro-inflammatory response is a biological activity of the "C4d" polypeptides to be used herein). As described herein and shown in the appended example, C4d polypeptides are capable of downregulating a pro-inflammatory response as they reduce intracellular calcium-flux or the production of inflammatory cytokines, like TNF-α or IL-6. Whether a polypeptide has this capacity can be tested by routine procedures exemplified in the appended example. A "pro-inflammatory response" is indicative of "inflammatory condition"/"disorders associated with immune-mediated inflammation" as described and defined herein. Thus, the following assays can also be used to confirm that the C4d to be used herein has a therapeutic effect in an "inflammatory condition"/"disorder associated with immune-mediated inflammation".

The term "biological activity" refers to triggering/inducing/stimulating an anti-inflammatory response. The term "biological activity" refers to the capacity to bind ILT4. The term "biological activity" refers preferably to the downregulation of a pro-inflammatory response. The activity to down-regulate a pro-inflammatory response can, for example, be assessed by the capacity to reduce intracellular calcium-flux. The activity to downregulate a pro-inflammatory response can, for example, be assessed by the capacity to reduce the level (or production) of inflammatory cytokines, like TNF-α or IL-6, for example in an "inflammatory model system". Such model systems are well known in the art. Exemplary "inflammatory model systems" are, for example, murine models of systemic lupus erythematosus as described in "Murine models of systemic lupus erythematosus".—Perry D et al., J Biomed Biotechnol. 2011; 2011:271694), murine models of erosive arthritis and/or rheumatoid arthritis as described in "Antiinflammatory effects of tumor necrosis factor on hematopoietic cells in a murine model of erosive arthritis".—Blüml S, et al., Arthritis Rheum. 2010 June; 62(6):1608-19), or murine models of graft rejection and graft versus host disease as described in "Allograft outcomes in outbred mice".—Reichenbach D K et al., Am J Transplant. 2013 March; 13(3):580-8.

For example, the following murine models can be used: NZB/W F1 (the oldest classical model of lupus in which the F1 hybrid is generated between the NZB and NZW strains), the MRL/lpr and BXSB/Yaa models (spontaneous Lupus), pristane-induced Lupus and induced Chronic Graft-versus-Host Disease models (models of inducible Lupus comprise pristane-induced Lupus and induced Chronic Graft-versus-Host Disease), C3H mice immunized with DBA/2 splenocytes (allo-transplant models/models for graft rejection; Larsen, 1996), and inbred and outbred mice, like the Tg197 mouse model (human TNF transgenic; genetic background C57BL/6; model of erosive arthritis and/or rheumatoid arthritis). These murine models are in detail described in Perry D et al., J Biomed Biotechnol. 2011; 2011:271694), Blüml S, et al., Arthritis Rheum. 2010 June; 62(6):1608-19), and Reichenbach D K et al., Am J Transplant. 2013 March; 13(3):580-8, which are incorporated herein by reference.

For assaying such a "biological activity" standard techniques can be used, like enzyme linked-immunosorbent assay (ELISA), Luminex or similar fluorescence bead based multiplex assay. Alternatively, Western Blot analysis or immunohistochemical staining can be performed.

Corresponding assays are described in more detail below. Such assays can be performed as follows, and respective results are depicted in FIG. 4:

Reduction of Intracellular $Ca^{2+}$-Flux by CSPs:

Labelling of monocytes using Indol-AM at 4 μM was performed in X-VIVO-10 supplemented with 100 U/ml penicillin and 100 μg/mL streptomycin at 37° C. for 45 minutes. Subsequently, the cells were washed in ice-cold PBS supplemented with 0.5% HSA (FACS buffer) and all subsequent steps were carried out at 4° C. The cells were resuspended in ice-cold FACS buffer, aliquoted to cell culture tubes and co-incubated for 30 minutes with monomeric human IgG and distinct biotinylated CSPs (C4d, C4b, C3d, C3b and iC3b) or ILT4 mouse monoclonal antibody. Then, the monocytes were washed twice, resuspended and co-incubated for 20 minutes with biotinylated goat IgG-Fab fragments specific for human IgG and either biotinylated mouse monoclonal antibodies specific for the aforementioned CSPs or biotinylated goat IgG-F(ab')$_2$ anti-mouse IgG. After two final washing steps the cells were resuspended and $Ca^{2+}$-flux was measured on a LSR II flow cytometer from Becton-Dickinson after bringing the cells to 37° C. in a water bath. After measuring the baseline $Ca^{2+}$-flux cells were incubated with soluble Streptavidin resulting in co-crosslink of biotinylated molecules attached to the cell surface. $Ca^{2+}$-flux as expressed by the Indo blue/Indo violet ratio was evaluated applying the FlowJo software from TreeStar Inc.

Reduction of Pro-Inflammatory Cytokine Production by C4d:

Ninety-six-well flat bottom cell culture plates were coated over night at 4° C. either with or without human IgG at 100 μg/mL in the presence or absence of 5 μg/mL Streptavidin or goat anti-mouse F(ab')$_2$ fragments. Coating volume was 100 μL per well. The following day, wells were washed five times using 200 μL DPBS per well. Subsequently, wells were blocked for two hours at 20° C. using 200 μL/well PBS supplemented with 2% HSA (human serum albumin). Then, the blocking buffer was removed and graded amounts of biotinylated C4d or anti-ILT4 mMAb diluted in blocking buffer was added. After two hours of incubation at 20° C., the wells were washed as described above and 50,000 freshly isolated monocytes resuspended in serum-free X-VIVO-10 supplemented with 100 U/ml penicillin and 100 μg/mL streptomycin were applied per well. The plates were incubated at 37° C. in the presence of 5% $CO_2$ and 100% air humidity. Production of TNF-α and IL-6 was assessed in cell free supernatants collected after 14 hours of stimulation via sandwich ELISA.

In the context of "an inflammatory condition"/"disorder associated with immune-mediated inflammation", as described herein the amount of intracellular $Ca^{2+}$-flux or the production of pro-inflammatory cytokines like TNF-α or IL-6 may be increased by 10%, 20%, 30%, 40% and by up to 50% as compared to a control (healthy) sample. A skilled person is aware of standard methods to be used in determining both intracellular $Ca^{2+}$-flux as well as the amount of inflammatory cytokines like TNF-α or IL-6 in a sample or may deduce corresponding methods from standard textbooks (e.g. Green and Sambrook: 'Molecular Cloning—A Laboratory Manual', Fourth Edition, 2012, Cold Spring Harbor Laboratory Press, ISBN 978-1-936113-41-5)) or online material (e.g. "Current Protocols", http://www.currentprotocols.com). For example, the amount of inflammatory cytokines like TNF-α or IL-6 in biological fluids or cell lysates can be determined by standard enzyme linked-immunosorbent assay (ELISA) or Luminex or similar fluorescence bead based multiplex assays. Alternatively, Western Blot analysis or immunohistochemical staining can be performed.

It has been found in the present invention that "C4d" as defined herein is capable of downregulating a pro-inflammatory response. This capacity is reflected in the herein provided C4d polypeptides to reduce the levels of inflammatory marker proteins, like TNF-α or IL-6, which are increased in inflammatory conditions. For example, "C4d" may decrease levels of inflammatory marker proteins, like TNF-α or IL-6 by at least about 10%, 15%, 20%, 25%, more preferably by at least about 30%, 35%, 40% or 45% and up to e.g. 50% when compared to a negative control (the negative control may be or be derived from an "inflammatory model system" which is not treated with "C4d"); see also the appended Example and FIG. 4. Exemplary model systems/models s are described herein above and below and can also be deduced e.g. from Perry D et al., J Biomed Biotechnol. 2011; 2011:271694), Blüml S, et al., Arthritis Rheum. 2010 June; 62(6):1608-19), and Reichenbach D K et al., Am J Transplant. 2013 March; 13(3):580-8, which are incorporated herein by reference.

Accordingly, "C4d" (i.e. the herein defined C4d polypeptides (as e.g. shown in SEQ ID NO: 2 or SEQ ID NO: 4 as well as fragments or derivatives thereof)) have the biological activity to decrease levels of inflammatory marker proteins (like TNF-α or IL-6) for example in an "inflammatory model system", by at least about 10%, 15%, 20%, 25%, more preferably by at least about 30%, 35%, 40% or 45% and up to e.g. 50% when compared to a negative control (the negative control being e.g. an "inflammatory model system" which is not treated with "C4d"). Suitable model systems (like NZB/W F1 models, MRL/lpr models, BXSB/Yaa models, pristane-induced Lupus models, induced Chronic Graft-versus-Host Disease models, C3H mice immunized with DBA/2 splenocytes, inbred and outbred mice, like the Tg197 mouse model are known in the art and are described herein.

Figure 3:
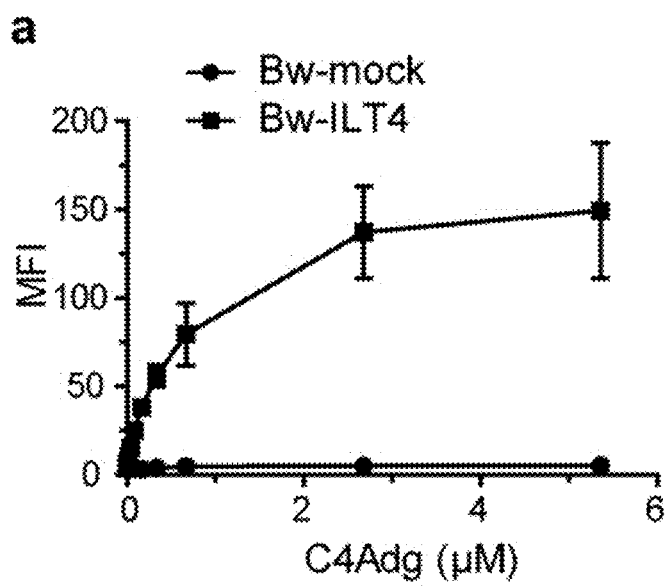
Figure 3:
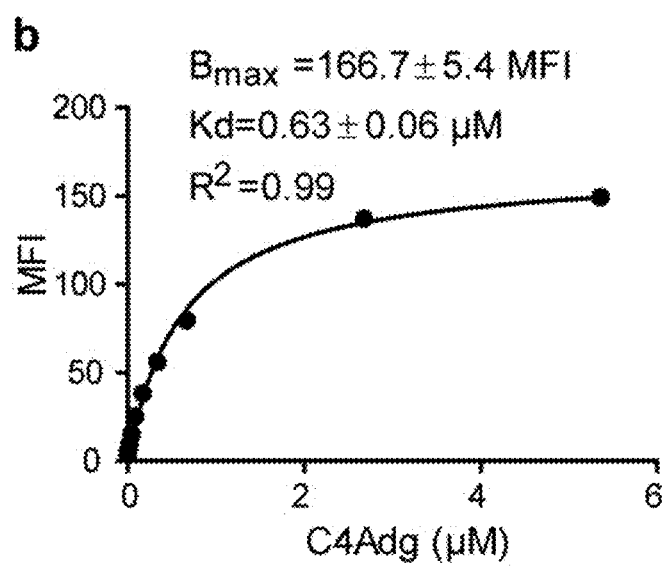
Figure 3:
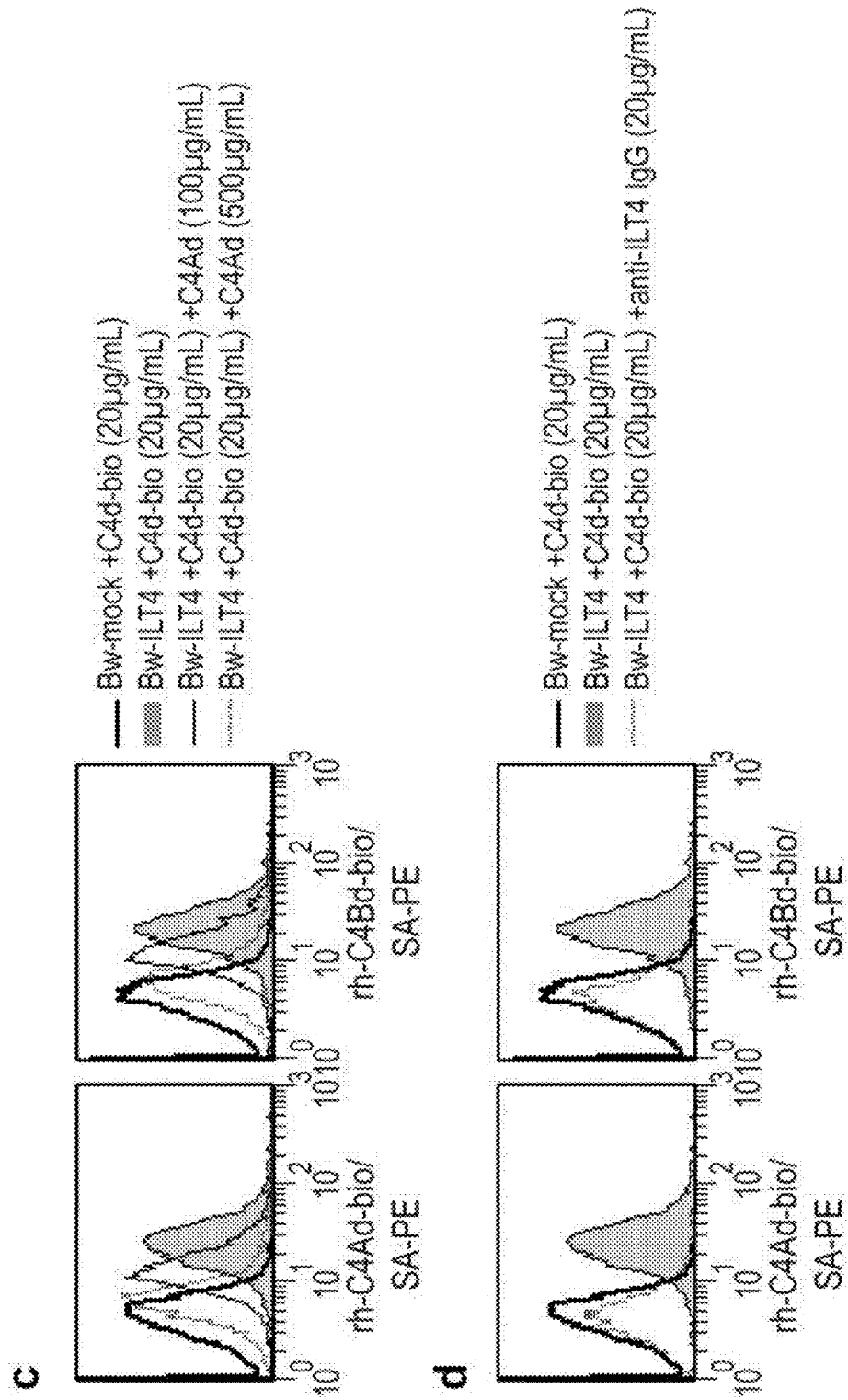

The interaction of C4d with ILT4 has the properties of a classical receptor-ligand interaction as it is saturable and binding of labelled C4d can be inhibited by excess of unlabelled C4d as well as by ILT4 antibodies as shown in FIG. 3.

The finding that human C4d also interacts with PIR-B, the murine ortholog of ILT4, will facilitate the evaluation of C4d-b (C4Bd) based therapeutic approaches for the treatment of immune disorders in pre-clinical in-vivo models, such as models of autoimmunity or models of allo-transplantation in rodents or other laboratory animals. This will allow for an assessment of the anti-inflammatory efficacy of C4d-preparations administered to respective animals.

Examples of diseases treatable by the application of C4d-preparations are described in detail elsewhere herein. An exemplary description of respective animal models is presented as follows:

There are a number of mouse models of systemic lupus erythematosus (reviewed in D. Perry et al. J Biomed Biotechnol. 2011; Epub 2011; PMID 21403825)), which allow for studying the impact of C4d-a (C4Ad) administration on both onset and severity of disease. One of these models is the NZB/W F1, the oldest classical model of lupus in which the F1 hybrid is generated between the NZB and NZW strains. While both NZB and NZW display limited autoimmunity, the NZB/W F1 hybrids develop severe lupus-like phenotypes comparable to that of lupus patients. These lupus-like phenotypes include lymphadenopathy, splenomegaly, elevated serum antinuclear autoantibodies (ANA) including anti-dsDNA IgG, a majority of which are IgG2a and IgG3, and immune complex-mediated glomerulonephritis (GN) that becomes apparent at 5-6 months of age, leading to kidney failure and death at 10-12 months of age.

There are other mouse models of spontaneous Lupus, such as the MRL/lpr and BXSB/Yaa models, which, in contrast to NZB/W F1 mice, do not lack autoantibodies against RNA-containing complexes.

Models of inducible Lupus comprise pristane-induced Lupus and induced Chronic Graft-versus-Host Disease. Unlike the models of spontaneous Lupus, in which genetic factors play the major role, induced mouse models develop lupus after exposure to environmental triggers.

Intraperitoneal injections of pristane (2, 6, 10, and 14 tetramethylpentadecane, TMPD), found at high concentration in mineral oil, into BALB/c mice induces autoantibodies characteristic of lupus, such as antiribonucleoprotein (RNP) antibodies (anti-Su, anti-Sm, and anti-U1RNP), anti-DNA, and anti-histone, to a level comparable to that found in MRL/lpr mice. Pristane-treated mice also have immune-complex deposition in the kidney leading to severe proteinuria and nephritis. Besides the BALB/c strain, almost all mouse strains are susceptible, to a variable extent, to the pristane-induced production of antibody and lupus manifestations. Like human SLE patients and NZB/W F1 model, pristine-induced lupus is more severe in females than in males, at least in SJL/J strain.

Various models of induced graft-versus-host disease (GVHD) have been used as models of lupus. These models require only a single injection of donor cells to induce a lupus-like syndrome. The disease process is reproducible, with severity correlating to the number of allografted cells. Because this method induces a rapid disease onset from a known starting point, the study of lupus induction is greatly facilitated as compared to the spontaneous models of lupus with autoantibodies being detectable as early as 10-14 days after induction, whereas it can be several weeks to months after birth for the same phenotype to develop in spontaneous lupus models. Since donor T cells undergo activation and expansion, they can be easily observed by flow cytometry, allowing the study of the effect of various modifications on the donor as well as the host cells.

There are a number of murine allo-transplant models which seem to be suitable to assess the anti-inflammatory (immunosuppressive) efficacy of C4d-preparations. The survival of allogenic skingrafts or cardiac allografts can be assessed in C3H mice immunized with DBA/2 splenocytes in their foodpads as described before (Larsen, 1996). The influence of C4d on the establishment of mixed chimerism through bone marrow transplantation in mouse models of tolerogenic cell therapy for application in solid organ transplantation can be assessed. A number of respective protocols have been published (reviewed in N. Pilat et al. Curr Opin Organ Transplant. 2012 February; 17(1):63-70. PMID: 22186093).).

All of these exemplary models are suitable to investigate the anti-inflammatory efficacy of the herein provided C4d, such as human C4d.

As mentioned above, particularly envisaged herein is the use of murine models of systemic lupus erythematosus as described in "Murine models of systemic lupus erythematosus".—Perry D et al., J Biomed Biotechnol. 2011; 2011: 271694), murine models of erosive arthritis and/or rheumatoid arthritis as described in "Antiinflammatory effects of tumor necrosis factor on hematopoietic cells in a murine model of erosive arthritis".—Blüml S, et al., Arthritis Rheum. 2010 June; 62(6):1608-19), and murine models of graft rejection and graft versus host disease as described in "Allograft outcomes in outbred mice".—Reichenbach D K et al., Am J Transplant. 2013 March; 13(3):580-8.

Further, the polypeptides to be used herein are, as shown in the appended example (FIG. 2b), capable of specifically binding to the receptor ILT-4. A corresponding assay for determining that a polypeptide specifically binds to ILT-4 can be performed as follows: Ninety-six-well ELISA plates (Corning Inc., Corning, N.Y.) can be coated over night at 4° C. applying unlabelled C4d at a concentration of e.g. 465 nM. The following day, the plates can be washed six times using PBS supplemented with 0.05% Tween20 (Biorad, Hercules, Calif.). Then, wells can be blocked for two hours at 20° C. applying PBS supplemented with 2% HSA. Subsequently, the blocking buffer can be removed and rh-ILT4-Fc fusion protein or control proteins like rh-ILT3-Fc fusion protein (each at 3 µg/ml) or sCD35 (5 µg/ml) diluted in blocking buffer can be added. All subsequent incubation steps can be carried out at 20° C. using blocking buffer as dilution medium. After two hours of incubation, the wells can be washed as described above and AP-labelled anti-human IgG-Fcγ-specific antibodies or anti-CD35 mMAb can be added to the fusion proteins or the sCD35 and incubated for one hour. After washing, the anti-CD35 mMAb can be incubated with HRP-labelled mouse-IgG-Fcγ-specific antibodies for one hour. The AP-signal can be assessed by determining the OD at λ=405 nm using a microplate reader (Thermomax, Molecular Devices, Sunnyvale, Calif.) after the addition of p-Nitrophenyl phosphate disodium hexahydrate (pNPP; Sigma-Aldrich) diluted in diethanolamine at 1 mg/ml. The HRP-signal can be measured at λ=405 nm after incubation with ABTS solution (Roche Applied Sciences, Penzberg, Germany).

Methods and assays for determining the capacity of "C4d" to downregulate a pro-inflammatory response or to specifically bind to the receptor ILT-4 are described herein above and in the appended examples. These capacities can be considered as exemplary (biological) activities of "C4d". Such exemplary capacities/activities exhibited by the exemplary polypeptides having an amino acid sequence as depicted in SEQ ID NO:2 (isoform C4d-A (C4Ad)) or SEQ ID NO: 4 (isoform C4d-B (C4Bd)) can be considered as "reference capacity/activity" of "C4d".

The term "C4d" may, preferably, refer to a human C4d polypeptide, such as a C4d polypeptide comprising the amino acid sequence shown in SEQ ID NO: 2 (isoform C4d-A (C4Ad)) or SEQ ID NO: 4 (isoform C4d-B (C4Bd)). The C4d polypeptide may be encoded by a nucleic acid sequence shown in SEQ ID NO: 1 (isoform C4d-A (C4Ad)) or SEQ ID NO: 3 (isoform C4d-B(C4Bd)). The sequences shown in SEQ ID NO: 1/SEQ ID NO: 3 (isoform C4d-A (C4Ad)) and SEQ ID NO: 2/SEQ ID NO: 4 (isoform C4d-B(C4Bd)) refer to the gene encoding the human C4d polypeptide (isoform C4d-A(C4Ad)) and the human C4d polypeptide (isoform C4d-A(C4Ad)) itself, respectively, and to the gene encoding the human C4d polypeptide (isoform C4d-B(C4Bd)) and the human C4d polypeptide (isoform C4d-B(C4Bd)) itself, respectively. However, the present invention is not limited to the use of human C4d (or a functional fragment or derivative thereof), but relates also to the medical use of orthologous or similar C4d (or a functional fragment or derivative thereof). The terms "orthologous"/"similar" are described herein below. For example, murine C4d may be used in context of the present invention in the place of human C4d. The respective sequences of orthologous C4d can be deduced from public databases.

Without deferring from the gist of the present invention also (functional) fragment or (functional) derivatives of the herein provided complement split products C4d can be used, for example, (functional) fragment or (functional) derivatives of human C4d polypeptide, such as a C4d polypeptide comprising the amino acid sequence shown in SEQ ID NO: 2 (isoform C4d-A (C4Ad)) or SEQ ID NO: 4 (isoform C4d-B (C4Bd)).

A fragment can consist of at least 100 contiguous amino acids of the amino acid sequence shown in SEQ ID NO: 2 (isoform C4d-A (C4Ad)) or SEQ ID NO: 4 (isoform C4d-B (C4Bd)). A fragment can consist of at least 110, 120, 130, 140, 150, 160, 170, 180, 190, 200, 210, 220, 230, 240, 250, 260, or at least 270 contiguous amino acids of the amino acid sequence shown in SEQ ID NO: 2 (isoform C4d-A (C4Ad)) or SEQ ID NO: 4 (isoform C4d-B (C4Bd)).

Preferably, a fragment can consist of at least 280 contiguous amino acids of the amino acid sequence shown in SEQ ID NO: 2 (isoform C4d-A (C4Ad)) or SEQ ID NO: 4 (isoform C4d-B (C4Bd)). A fragment can consist of at least 290, 300, 310, 320, 330, 340, 350, 360 or 370 contiguous amino acids of the amino acid sequence shown in SEQ ID NO: 2 (isoform C4d-A (C4Ad)) or SEQ ID NO: 4 (isoform C4d-B (C4Bd)). An exemplary fragment of a C4d polypeptide to be used in accordance with the present invention may, for example, have 39 amino acids deleted at the N-terminus of SEQ ID NO: 2 and/or have 15 amino acids deleted at the C-terminus of SEQ ID NO: 2.

The fragment or derivative preferably has the biological activity (down-regulation of a pro-inflammatory response/triggering/inducing/stimulating an anti-inflammatory response) as defined above. For example, the fragment or derivative can have the same (or essentially the same) biological activity as the full length polypeptide having the amino acid sequence shown in SEQ ID NO: 2 (isoform C4Ad) or SEQ ID NO: 4 (isoform C4Bd). In this sense, the fragment or derivative is a "functional" fragment or derivative to be used herein.

In context of the present invention, human C4d (or a functional fragment or derivative thereof derived from human C4d) may be used in the treatment of humans suffering from an inflammatory condition. Correspondingly, murine C4d (a functional fragment or derivative thereof derived from murine C4d) can be used in the treatment of mice suffering from an inflammatory condition. Accordingly, the C4d (or functional fragment or derivative thereof) to be used in the treatment of a specific organism (e.g. human, mouse, pig and the like) may be isolated or derived from a sample from said specific organism (e.g. human, mouse or pig, respectively). The C4d isolated/derived from a specific organism as described above may also be used in the treatment of closely related organisms; for example, human C4d (or functional fragment or derivative thereof) may be used in the treatment of a chimpanzee, and vice versa.

It is also envisaged that the specific C4d isolated/derived from a specific organism may also be used in the treatment of distantly related organisms; for example, human (or functional fragment or derivative thereof) may be used in the treatment of a mouse. Indeed, the examples show that human C4d may be used in mice and may be used in corresponding animal tests as described herein above. Closely related organisms may, in particular, be organisms which form a subgroup of a species, e.g. different races of a species. Also organisms which belong to a different species but can be subgrouped under a common genus can be considered as closely related. Less closely related organisms belong to different genera subgrouped under one family. Distantly related organisms belong to different families. The taxonomic terms "race", "species", "genus", "family" and the like are well known in the art and can easily be derived from standard textbooks. Based on the teaching provided in the present invention a skilled person is therefore easily in the position to identify "closely related" or "distantly related" organisms. A person skilled in the art is capable of identifying and/or isolating C4d as defined herein and in particular as defined in sections (a) to (f) of the above-mentioned aspect of the present invention or a nucleic acid molecule encoding said C4d from a specific organism (e.g. human, mouse, pig, guinea pig, rat, and the like) using standard techniques.

As used herein the terms "human C4d"/"C4d of human origin" refer in particular to (a) protein(s) as found in the human body which can accordingly be isolated from a sample obtained from a human. The term "C4d (or a functional fragment or derivative thereof) derived from human C4d" refers in particular to "human C4d"/"C4d of human origin" which is modified as described herein below (e.g. by way of substitution, deletion, addition and/or insertion of (an) amino acid(s)). Said modified polypeptide may also form part of a fusion protein or may form multimeric proteins. The explanations given herein above in respect of "human C4d"/"C4d of human origin" apply, mutatis mutandis, to "murine C4d"/"C4d of murine origin" and C4d isolated from other organisms, such as pigs, guinea pigs, rats, and the like.

The use of C4d (or a functional fragment or derivative thereof) as described and defined herein in the treatment of economically, agronomically or scientifically important organisms is envisaged herein. Scientifically or experimentally important organisms include, but are not limited to, mice, rats, rabbits, guinea pigs and pigs. Yet, the treatment of (a) human(s) with C4d (in particular C4d of human origin or derived from human C4d) or a functional fragment or derivative thereof is preferred in context of the present invention.

The complement split product C4d to be used in accordance with the present invention, inter alia, in the treatment of an inflammatory condition, may be a C4d polypeptide selected from the group consisting of
(a) a polypeptide comprising or consisting of an amino acid sequence encoded by a nucleic acid molecule having the nucleic acid sequence as depicted in SEQ ID NO: 1 (isoform C4d-A (C4Ad)) or SEQ ID NO: 3 (isoform C4d-B(C4Bd));
(b) a polypeptide having or consisting of an amino acid sequence as depicted in SEQ ID NO:2 (isoform C4d-A (C4Ad)) or SEQ ID NO: 4 (isoform C4d-B(C4Bd));
(c) a polypeptide as defined in (a) or (b) wherein one or more amino acids are deleted, inserted, added or substituted, and whereby said polypeptide has C4d biological activity;
(d) a polypeptide encoded by a nucleic acid molecule encoding a peptide having or consisting of an amino acid sequence as depicted in SEQ ID NO:2 (isoform C4d-A (C4Ad)) or SEQ ID NO: 4 (isoform C4d-B(C4Bd));
(e) a polypeptide comprising or consisting of an amino acid sequence encoded by a nucleic acid molecule hybridizing under stringent conditions to the complementary strand of nucleic acid molecules as defined in (a) or (d) and whereby said polypeptide has C4d biological activity;
(f) a polypeptide having at least 60% similarity to the polypeptide of any one of (a) to (e), and whereby said polypeptide has C4d biological activity; and
(g) a polypeptide comprising or consisting of an amino acid sequence encoded by a nucleic acid molecule being degenerate as a result of the genetic code to the nucleotide sequence of a nucleic acid molecule as defined in (a), (d) and (e).

The term "C4d polypeptide" to be used in context of the present invention may refer to a polypeptide having at least 60% similarity to a polypeptide as defined in section (a) to (e) of the above-described specific aspect of the present invention. The "C4d polypeptide" has preferably essentially the same biological activity as a polypeptide having 100% similarity to a polypeptide as indicated in section (a), (b) or (d), i.e. a polypeptide being essentially identical to a polypeptide having an amino acid sequence as depicted in SEQ ID NO:2 (isoform C4d-A(C4Ad)) or SEQ ID NO: 4 (isoform C4d-B(C4Bd)). Methods for determining the activity of (a) polypeptide(s) are described above.

It is of note that C4d or a functional fragment or derivative thereof as described and defined herein may further comprise a heterologous polypeptide, for example, (an) amino acid sequence(s) for identification and/or purification of the recombinant protein (e.g. amino acid sequence from C-MYC, GST protein, FLAG peptide, HIS peptide and the like), an amino acid sequence used as reporter (e.g. green fluorescent protein, yellow fluorescent protein, red fluorescent protein, luciferase, and the like), or antibodies/antibody fragments (like scFv). A person skilled in the art knows that for determination of similarity as described herein only a part of the C4d polypeptides is to be used, whereby said part is C4d (or a functional fragment or derivative thereof). Also further compounds (e.g. toxins or antibodies or fragments thereof) may be attached to C4d (or a functional fragment or derivative thereof) by standard techniques. These compounds may, in particular, be useful in a medical setting as described herein, wherein C4d (or a functional fragment or derivative thereof) is used. A skilled person is aware of compounds to be used/attached in this context.

It is also envisaged herein that C4d (or a functional fragment or derivative thereof) as defined herein, though being of, for example, human, murine or porcine origin (e.g. C4d isolated from human, mouse or pig as described above), may be modified in order to change certain properties of the polypeptide. For example, such a modified C4d (or a functional fragment or derivative thereof) may exhibit increased biological activity as defined herein or increased stability when compared to the "original" C4d (i.e. the C4d as produced in a healthy, non-transgenic organism, e.g. human C4d as defined above). For example, the polypeptide having the amino acid sequence as shown in SEQ ID NO: 2 or SEQ ID NO: 4 can be considered as "original" human C4d. A "modified" C4d (or a functional fragment thereof) may have (an) insertion(s), (a) deletion(s), additions(s) and/or (an) substitution(s) of one or more amino acids as described below in more detail.

As the first medical use of C4d is provided herein, the present invention relates, inter alia, to the complement split product C4d as defined herein for use in medicine.

The complement split product C4d for use in medicine, may be a C4d polypeptide selected from the group consisting of
(a) a polypeptide comprising or consisting of an amino acid sequence encoded by a nucleic acid molecule having the nucleic acid sequence as depicted in SEQ ID NO: 1 (isoform C4d-A(C4Ad)) or SEQ ID NO: 3 (isoform C4d-B(C4Bd));
(b) a polypeptide having or consisting of an amino acid sequence as depicted in SEQ ID NO:2 (isoform C4d-A (C4Ad)) or SEQ ID NO: 4 (isoform C4d-B(C4Bd));
(c) a polypeptide as defined in (a) or (b) wherein one or more amino acids are deleted, inserted, added or substituted, and whereby said polypeptide has C4d biological activity;
(d) a polypeptide encoded by a nucleic acid molecule encoding a peptide having or consisting of an amino acid sequence as depicted in SEQ ID NO:2 (isoform C4d-A (C4Ad)) or SEQ ID NO: 4 (isoform C4d-B(C4Bd));

(e) a polypeptide comprising or consisting of an amino acid sequence encoded by a nucleic acid molecule hybridizing under stringent conditions to the complementary strand of nucleic acid molecules as defined in (a) or (d) and whereby said polypeptide has C4d biological activity;
(f) a polypeptide having at least 60% similarity to the polypeptide of any one of (a) to (e), and whereby said polypeptide has C4d biological activity; and
(g) a polypeptide comprising or consisting of an amino acid sequence encoded by a nucleic acid molecule being degenerate as a result of the genetic code to the nucleotide sequence of a nucleic acid molecule as defined in (a), (d) and (e).

The "C4d" to be used herein is preferably a C4d multimer, like a C4d polypeptide multimer. As mentioned, it has surprisingly been found in the present invention that "C4d" is capable of triggering an anti-inflammatory response (or likewise "C4d" is capable of down-regulating a pro-inflammatory response). Without being bound by theory, it is believed that the specific binding of "C4d" to its receptor ILT-4 induces or is associated with downregulation of a pro-inflammatory response.

In the human body, the C4d polypeptides remain, after cleavage of the precursor molecules, on the cell-surface. It is believed that these cell-surface bound C4d polypeptides interact with ILT-4. Further, it is believed that the cell-surface bound C4d polypeptides are present at a relatively high density at the cell-surface and that this may contribute, by interaction with ILT-4, to the downregulation of a pro-inflammatory response. It is, therefore, desirable that the herein provided use of C4d polypeptides for the treatment of an inflammatory condition reflects closely the conditions that are found in the human body. For that purpose, it is believed that it is beneficial to use C4d multimers reflecting the relatively high density of the cell-surface bound C4d polypeptides at the cell-surface in the human body. In the Example, biotinylated C4d polypeptides were used as exemplary functional multimers. These multimers strongly down-regulated a pro-inflammatory response as reflected in decreased levels of inflammatory markers TNF-α and IL-6 as well as a marked decrease in intracellular $Ca^{2+}$-flux.

While the present invention provides the first medical use of these novel compounds (i.e. C4d multimers) it also relates to the C4d multimers as such.

The present invention provides a complement split product C4d polypeptide multimer, said multimer comprising two or more complement split product C4d polypeptides selected from the group consisting of
(a) a polypeptide comprising or consisting of an amino acid sequence encoded by a nucleic acid molecule having the nucleic acid sequence as depicted in SEQ ID NO: 1 (isoform C4d-A(C4Ad)) or SEQ ID NO: 3 (isoform C4d-B(C4Bd));
(b) a polypeptide having or consisting of an amino acid sequence as depicted in SEQ ID NO:2 (isoform C4d-A (C4Ad)) or SEQ ID NO: 4 (isoform C4d-B(C4Bd));
(c) a polypeptide as defined in (a) or (b) wherein one or more amino acids are deleted, inserted, added or substituted, and whereby said polypeptide has C4d biological activity;
(d) a polypeptide encoded by a nucleic acid molecule encoding a peptide having or consisting of an amino acid sequence as depicted in SEQ ID NO:2 (isoform C4d-A (C4Ad)) or SEQ ID NO: 4 (isoform C4d-B(C4Bd));
(e) a polypeptide comprising or consisting of an amino acid sequence encoded by a nucleic acid molecule hybridizing under stringent conditions to the complementary strand of nucleic acid molecules as defined in (a) or (d) and whereby said polypeptide has C4d biological activity;
(f) a polypeptide having at least 60% similarity to the polypeptide of any one of (a) to (e), and whereby said polypeptide has C4d biological activity; and
(g) a polypeptide comprising or consisting of an amino acid sequence encoded by a nucleic acid molecule being degenerate as a result of the genetic code to the nucleotide sequence of a nucleic acid molecule as defined in (a), (d) and (e).

Therefore, the present invention relates to (a) C4d multimer(s) and the use of the C4d multimer(s) in medicine, like in the treatment of an inflammatory condition.

The present invention relates to a complement split product C4d polypeptide multimer for use in medicine, said multimer comprising two or more complement split product C4d polypeptides selected from the group consisting of
(a) a polypeptide comprising or consisting of an amino acid sequence encoded by a nucleic acid molecule having the nucleic acid sequence as depicted in SEQ ID NO: 1 (isoform C4d-A(C4Ad)) or SEQ ID NO: 3 (isoform C4d-B(C4Bd));
(b) a polypeptide having or consisting of an amino acid sequence as depicted in SEQ ID NO:2 (isoform C4d-A (C4Ad)) or SEQ ID NO: 4 (isoform C4d-B(C4Bd));
(c) a polypeptide as defined in (a) or (b) wherein one or more amino acids are deleted, inserted, added or substituted, and whereby said polypeptide has C4d biological activity;
(d) a polypeptide encoded by a nucleic acid molecule encoding a peptide having or consisting of an amino acid sequence as depicted in SEQ ID NO:2 (isoform C4d-A (C4Ad)) or SEQ ID NO: 4 (isoform C4d-B(C4Bd));
(e) a polypeptide comprising or consisting of an amino acid sequence encoded by a nucleic acid molecule hybridizing under stringent conditions to the complementary strand of nucleic acid molecules as defined in (a) or (d) and whereby said polypeptide has C4d biological activity;
(f) a polypeptide having at least 60% similarity to the polypeptide of any one of (a) to (e), and whereby said polypeptide has C4d biological activity; and
(g) a polypeptide comprising or consisting of an amino acid sequence encoded by a nucleic acid molecule being degenerate as a result of the genetic code to the nucleotide sequence of a nucleic acid molecule as defined in (a), (d) and (e).

The present invention relates to a complement split product C4d polypeptide multimer for use in treating an inflammatory condition, said multimer comprising two or more complement split product C4d polypeptides selected from the group consisting of
(a) a polypeptide comprising or consisting of an amino acid sequence encoded by a nucleic acid molecule having the nucleic acid sequence as depicted in SEQ ID NO: 1 (isoform C4d-A(C4Ad)) or SEQ ID NO: 3 (isoform C4d-B(C4Bd));
(b) a polypeptide having or consisting of an amino acid sequence as depicted in SEQ ID NO:2 (isoform C4d-A (C4Ad)) or SEQ ID NO: 4 (isoform C4d-B(C4Bd));
(c) a polypeptide as defined in (a) or (b) wherein one or more amino acids are deleted, inserted, added or substituted, and whereby said polypeptide has C4d biological activity;
(d) a polypeptide encoded by a nucleic acid molecule encoding a peptide having or consisting of an amino acid sequence as depicted in SEQ ID NO:2 (isoform C4d-A (C4Ad)) or SEQ ID NO: 4 (isoform C4d-B(C4Bd));
(e) a polypeptide comprising or consisting of an amino acid sequence encoded by a nucleic acid molecule hybridizing under stringent conditions to the complementary strand of nucleic acid molecules as defined in (a) or (d) and whereby said polypeptide has C4d biological activity;

(f) a polypeptide having at least 60% similarity to the polypeptide of any one of (a) to (e), and whereby said polypeptide has C4d biological activity; and (g) a polypeptide comprising or consisting of an amino acid sequence encoded by a nucleic acid molecule being degenerate as a result of the genetic code to the nucleotide sequence of a nucleic acid molecule as defined in (a), (d) and (e).

The C4d multimer may comprise or consist of one, preferably of two or more C4d polypeptides as defined herein above. Accordingly, a C4d multimer may be a dimer, trimer and the like and may comprise of from 2, 3, 4, 5 to 10 and up to 20 C4d polypeptides (and/or (a) functional fragment(s) or (a) functional derivative(s) thereof). Preferably, the C4d multimer is a C4d dimer or C4d trimer. Particularly preferred is a C4d dimer. In other words, the C4d multimer provided and to be used herein comprises preferably 2 C4d polypeptides as defined herein or 3 C4d polypeptides as defined herein. Particularly preferred is a C4d multimer provided and to be used herein which comprises preferably 2 C4d polypeptides as defined herein.

The complement split product C4d polypeptide multimer provided herein and to be used in accordance with the present invention comprises two or more complement split product C4d polypeptides selected from the group consisting of (a) a polypeptide comprising or consisting of an amino acid sequence encoded by a nucleic acid molecule having the nucleic acid sequence as depicted in SEQ ID NO: 1 (isoform C4d-A(C4Ad)) or SEQ ID NO: 3 (isoform C4d-B(C4Bd));

(b) a polypeptide having or consisting of an amino acid sequence as depicted in SEQ ID NO:2 (isoform C4d-A (C4Ad)) or SEQ ID NO: 4 (isoform C4d-B(C4Bd)).

The complement split product C4d polypeptide multimer provided herein and to be used in accordance with the present invention can comprise two complement split product C4d polypeptides selected from the group consisting of (a) a polypeptide comprising or consisting of an amino acid sequence encoded by a nucleic acid molecule having the nucleic acid sequence as depicted in SEQ ID NO: 1 (isoform C4d-A(C4Ad)) or SEQ ID NO: 3 (isoform C4d-B(C4Bd));

(b) a polypeptide having or consisting of an amino acid sequence as depicted in SEQ ID NO:2 (isoform C4d-A (C4Ad)) or SEQ ID NO: 4 (isoform C4d-B(C4Bd)).

The complement split product C4d polypeptide multimer provided herein and to be used in accordance with the present invention can comprise three complement split product C4d polypeptides selected from the group consisting of (a) a polypeptide comprising or consisting of an amino acid sequence encoded by a nucleic acid molecule having the nucleic acid sequence as depicted in SEQ ID NO: 1 (isoform C4d-A(C4Ad)) or SEQ ID NO: 3 (isoform C4d-B(C4Bd));

(b) a polypeptide having or consisting of an amino acid sequence as depicted in SEQ ID NO:2 (isoform C4d-A (C4Ad)) or SEQ ID NO: 4 (isoform C4d-B(C4Bd)).

The complement split product C4d polypeptide multimer provided herein and to be used in accordance with the present invention can comprise two complement split product C4d polypeptides having or consisting of an amino acid sequence as depicted in SEQ ID NO:2 (isoform C4d-A (C4Ad)) or SEQ ID NO: 4 (isoform C4d-B(C4Bd)).

The complement split product C4d polypeptide multimer provided herein and to be used in accordance with the present invention comprises three complement split product C4d polypeptides selected from the group consisting of (a) a polypeptide comprising or consisting of an amino acid sequence encoded by a nucleic acid molecule having the nucleic acid sequence as depicted in SEQ ID NO: 1 (isoform (C4Ad)) or SEQ ID NO: 3 (isoform (C4Bd));

(b) a polypeptide having or consisting of an amino acid sequence as depicted in SEQ ID NO:2 (isoform (C4Ad)) or SEQ ID NO: 4 (isoform (C4Bd)).

The complement split product C4d polypeptide multimer provided herein and to be used in accordance with the present invention can comprise three complement split product C4d polypeptides having or consisting of an amino acid sequence as depicted in SEQ ID NO:2 (isoform (C4Ad)) or SEQ ID NO: 4 (isoform (C4Bd)).

It is envisaged that the C4d (polypeptide) multimers can comprise different C4d polypeptides)(i.e. C4d polypeptides or fragments or derivatives thereof) which are not identical, because they have, for example, a different amino acid sequence). Yet, it is preferred herein that the C4d (polypeptide) multimers comprise identical C4d (polypeptides) (i.e. C4d polypeptides or fragments or derivatives thereof) with an identical amino acid sequence. Thus, C4d (polypeptide) homo-multimers are preferred.

For example, the C4d (polypeptide) multimer can comprise two or more of (a) a polypeptide comprising or consisting of an amino acid sequence encoded by a nucleic acid molecule having the nucleic acid sequence as depicted in SEQ ID NO: 1 (isoform C4d-A(C4Ad)); or (b) a polypeptide having or consisting of an amino acid sequence as depicted in SEQ ID NO:2 (isoform C4d-A(C4Ad)). For example, the C4d (polypeptide) multimer can comprise two or more of a (a) polypeptide comprising or consisting of an amino acid sequence encoded by a nucleic acid molecule having the nucleic acid sequence as depicted in SEQ ID NO: 3 (isoform C4d-B(C4Bd)); or (b) a polypeptide having or consisting of an amino acid sequence as depicted in SEQ ID NO: 3 (isoform C4d-B(C4Bd)).

For example, the C4d polypeptide as comprised in a C4d (polypeptide) multimer may be a C4d polypeptide selected from the group consisting of (a) a polypeptide comprising or consisting of an amino acid sequence encoded by a nucleic acid molecule having the nucleic acid sequence as depicted in SEQ ID NO: 1 (isoform C4d-A(C4Ad)) or SEQ ID NO: 3 (isoform C4d-B(C4Bd));

(b) a polypeptide having or consisting of an amino acid sequence as depicted in SEQ ID NO:2 (isoform C4d-A (C4Ad)) or SEQ ID NO: 4 (isoform C4d-B(C4Bd));

(c) a polypeptide as defined in (a) or (b) wherein one or more amino acids are deleted, inserted, added or substituted, and whereby said polypeptide has C4d biological activity;

(d) a polypeptide encoded by a nucleic acid molecule encoding a peptide having or consisting of an amino acid sequence as depicted in SEQ ID NO:2 (isoform C4d-A (C4Ad)) or SEQ ID NO: 4 (isoform C4d-B(C4Bd));

(e) a polypeptide comprising or consisting of an amino acid sequence encoded by a nucleic acid molecule hybridizing under stringent conditions to the complementary strand of nucleic acid molecules as defined in (a) or (d) and whereby said polypeptide has C4d biological activity;

(f) a polypeptide having at least 60% similarity to the polypeptide of any one of (a) to (e), and whereby said polypeptide has C4d biological activity; and (g) a polypeptide comprising or consisting of an amino acid sequence encoded by a nucleic acid molecule being degenerate as a result of the genetic code to the nucleotide sequence of a nucleic acid molecule as defined in (a), (d) and (e).

For example, the C4d (polypeptide) (homo-)multimer can comprise two or more C4d polypeptides selected from the group consisting of
(a) a polypeptide comprising or consisting of an amino acid sequence encoded by a nucleic acid molecule having the nucleic acid sequence as depicted in SEQ ID NO: 1 (isoform C4d-A(C4Ad));
(b) a polypeptide having or consisting of an amino acid sequence as depicted in SEQ ID NO:2 (isoform C4d-A (C4Ad));
(c) a polypeptide as defined in (a) or (b) wherein one or more amino acids are deleted, inserted, added or substituted, and whereby said polypeptide has C4d biological activity;
(d) a polypeptide encoded by a nucleic acid molecule encoding a peptide having or consisting of an amino acid sequence as depicted in SEQ ID NO:2 (isoform C4d-A (C4Ad));
(e) a polypeptide comprising or consisting of an amino acid sequence encoded by a nucleic acid molecule hybridizing under stringent conditions to the complementary strand of nucleic acid molecules as defined in (a) or (d) and whereby said polypeptide has C4d biological activity;
(f) a polypeptide having at least 60% similarity to the polypeptide of any one of (a) to (e), and whereby said polypeptide has C4d biological activity; and
(g) a polypeptide comprising or consisting of an amino acid sequence encoded by a nucleic acid molecule being degenerate as a result of the genetic code to the nucleotide sequence of a nucleic acid molecule as defined in (a), (d) and (e).

For example, the C4d (polypeptide) (homo-)multimer can comprise two or more C4d polypeptides selected from the group consisting of
(a) a polypeptide comprising or consisting of an amino acid sequence encoded by a nucleic acid molecule having the nucleic acid sequence as depicted in SEQ ID NO: 3 (isoform C4d-B(C4Bd));
(b) a polypeptide having or consisting of an amino acid sequence as depicted in SEQ ID NO: 4 (isoform C4d-B (C4Bd));
(c) a polypeptide as defined in (a) or (b) wherein one or more amino acids are deleted, inserted, added or substituted, and whereby said polypeptide has C4d biological activity;
(d) a polypeptide encoded by a nucleic acid molecule encoding a peptide having or consisting of an amino acid sequence as depicted in SEQ ID NO: 4 (isoform C4d-B (C4Bd));
(e) a polypeptide comprising or consisting of an amino acid sequence encoded by a nucleic acid molecule hybridizing under stringent conditions to the complementary strand of nucleic acid molecules as defined in (a) or (d) and whereby said polypeptide has C4d biological activity;
(f) a polypeptide having at least 60% similarity to the polypeptide of any one of (a) to (e), and whereby said polypeptide has C4d biological activity; and
(g) a polypeptide comprising or consisting of an amino acid sequence encoded by a nucleic acid molecule being degenerate as a result of the genetic code to the nucleotide sequence of a nucleic acid molecule as defined in (a), (d) and (e).

The complement split product C4d polypeptide (homo-)multimer provided herein and to be used in accordance with the present invention comprises two or more complement split product C4d polypeptides selected from the group consisting of
(a) a polypeptide comprising or consisting of an amino acid sequence encoded by a nucleic acid molecule having the nucleic acid sequence as depicted in SEQ ID NO: 1 (isoform C4d-A(C4Ad));
(b) a polypeptide having or consisting of an amino acid sequence as depicted in SEQ ID NO:2 (isoform C4d-A (C4Ad)).

The complement split product C4d polypeptide (homo-)multimer provided herein and to be used in accordance with the present invention can comprise two complement split product C4d polypeptides having or consisting of an amino acid sequence as depicted in SEQ ID NO:2 (isoform C4d-A(C4Ad)).

The complement split product C4d polypeptide (homo-)multimer provided herein and to be used in accordance with the present invention comprises two or more complement split product C4d polypeptides selected from the group consisting of
(a) a polypeptide comprising or consisting of an amino acid sequence encoded by a nucleic acid molecule having the nucleic acid sequence as depicted in SEQ ID NO: 3 (isoform C4d-B(C4Bd));
(b) a polypeptide having or consisting of an amino acid sequence as depicted in SEQ ID NO: 4 (isoform C4d-B (C4Bd)).

The complement split product C4d polypeptide multimer provided herein and to be used in accordance with the present invention can comprise two complement split product C4d polypeptides having or consisting of an amino acid sequence as depicted in SEQ ID NO: 4 (isoform C4d-B (C4Bd)).

The herein provided and described complement split product C4d polypeptide multimer is for use in medicine, particularly for use in treating an inflammatory condition. Specific inflammatory conditions to be treated in accordance with the present invention are defined and disclosed herein.

The present invention relates to a pharmaceutical composition for use in treating an inflammatory condition, said pharmaceutical composition comprising a complement split product C4d multimer, said multimer comprising two or more complement split product C4d polypeptides, wherein said complement split product C4d polypeptide is selected from the group consisting of
(a) a polypeptide comprising an amino acid sequence encoded by a nucleic acid molecule having the nucleic acid sequence as depicted in SEQ ID NO: 1 (isoform complement split product C4d-A(C4Ad)) or SEQ ID NO: 3 (isoform complement split product C4d-B(C4Bd));
(b) a polypeptide having an amino acid sequence as depicted in SEQ ID NO:2 (isoform complement split product C4d-A(C4Ad)) or SEQ ID NO: 4 (isoform complement split product C4d-B(C4Bd)).

The present invention relates to a pharmaceutical composition for use in treating an inflammatory condition, said pharmaceutical composition comprising a complement split product C4d multimer, said multimer comprising two or more complement split product C4d polypeptides, wherein said complement split product C4d polypeptide is a polypeptide having an amino acid sequence as depicted in SEQ ID NO:2 (isoform complement split product C4d-A(C4Ad)).

The present invention relates to a pharmaceutical composition for use in treating an inflammatory condition, said pharmaceutical composition comprising a complement split product C4d multimer, said multimer comprising two or more complement split product C4d polypeptides, wherein said complement split product C4d polypeptide is a polypeptide having an amino acid sequence as depicted in SEQ ID NO: 4 (isoform complement split product C4d-B (C4Bd)).

Without deferring from the gist of the present invention, (functional) fragments or (functional) derivatives of complement split product C4d polypeptide(s) as defined above can be used herein, also in context of the herein provided complement split product C4d polypeptide multimers. The definitions of (functional) fragments or (functional) derivatives of complement split product C4d polypeptide(s) provided herein apply mutatis mutandis in this context.

Such C4d (polypeptide) multimers may be produced e.g. by recombinant (biotechnological) techniques and/or by chemical techniques.

For example, the C4d multimers can be recombinantly produced by taking advantage of nucleic acid molecules encoding such multimers. A nucleic acid encoding a C4d dimer may, for example, comprise
(i) a nucleic acid sequence encoding a translated amino acid and/or a leader sequence;
(ii) a nucleic acid sequence encoding a first C4d polypeptide (or a functional fragment or derivative thereof);
(iii) optionally a nucleic acid sequence encoding a linker peptide;
(iv) a nucleic acid sequence encoding a second C4d polypeptide (or a functional fragment or derivative thereof); and
(v) a nucleic acid sequence that represents or is a translational stop codon.

The above mentioned "translated amino acid and/or a leader sequence" under (i) may for example be the starting "M", i.e. a methionine derived from a corresponding starting codon, it may also comprise non-translated sequences of an mRNA like the 5' sequence up to a start codon which comprises for example a ribosome binding site. Such a sequence may however also comprise classical leader and/or signal sequences for example for secretion of an expressed protein into the periplasm or in a culture medium. Prokaryotic signal peptides are for example OmpA, MalE, PhoA, DsbA, pelB, Afa, npr, STII. Eukaryotic signal peptides are for example Honeybee melittin signal sequence, acidic glycoprotein gp67 signal sequence, mouse IgM signal sequence, hGH signal sequence. It is to be understood that nucleic acids encoding the herein provided C4d multimers are in frame (i.e. the reading frame is maintained allowing generation of bona fide C4d multimers, wherein the C4d polypeptide retain their biological activity. Translational stop codons to be employed in the nucleic acid molecule provided herein are well known in the art and are, e.g. codons UAA, UAG or UGA.

In accordance with the present invention, the nucleic acid molecule encoding the C4d multimers may comprise more than two nucleic acid sequences encoding a C4d polypeptide. Accordingly, such a nucleic acid molecule may encode 3, 4, 5, 6 and up to 10 or 20 C4d polypeptides.

For example, a nucleic acid encoding a C4d trimer may comprise
(i) a nucleic acid sequence encoding a translated amino acid and/or a leader sequence;
(ii) a nucleic acid sequence encoding a first C4d polypeptide (or a functional fragment or derivative thereof);
(iii) optionally a nucleic acid sequence encoding a linker peptide;
(iv) a nucleic acid sequence encoding a second C4d polypeptide (or a functional fragment or derivative thereof);
(v) optionally a nucleic acid sequence encoding a linker peptide;
(vi) a nucleic acid sequence encoding a third C4d polypeptide (or a functional fragment or derivative thereof); and
(vii) a nucleic acid sequence that represents or is a translational stop codon.

Corresponding nucleic acid molecules encoding 4, 5, 6 and up to 10 or 20 C4d polypeptides are also subject of the present invention.

In accordance with the above, the herein provided C4d (polypeptide) multimer(s) (e.g. C4d dimers, trimers etc.) may, for example, comprise
(i) a translated amino acid and/or a leader sequence (this translated amino acid and/or leader sequence may also be absent, for example, due to (enzymatic) cleavage of the leader sequence etc);
(ii) a first C4d polypeptide (or a functional fragment or derivative thereof);
(iii) optionally a linker peptide;
(iv) a second C4d polypeptide (or a functional fragment or derivative thereof).

An exemplary C4d trimer may, accordingly, comprise
(i) a translated amino acid and/or a leader sequence (this translated amino acid and/or leader sequence may also be absent, for example, due to (enzymatic) cleavage of the leader sequence etc);
(ii) a first C4d polypeptide (or a functional fragment or derivative thereof);
(iii) optionally a linker peptide;
(iv) a second C4d polypeptide (or a functional fragment or derivative thereof).
(v) optionally a linker peptide;
(vi) a third C4d polypeptide (or a functional fragment or derivative thereof).

The C4d polypeptides of C4d polypeptide multimers (or a functional fragment or derivative thereof) may be identical or different C4d polypeptides (or a functional fragment or derivative thereof) as defined herein. For example, a C4d polypeptide dimer may comprise two identical C4d polypeptides (e.g. two polypeptides having or consisting of the sequence as depicted in SEQ ID NO:2 (isoform C4d-A (C4Ad)) or two polypeptides having or consisting of the sequence as depicted in SEQ ID NO: 4 (isoform C4d-B (C4Bd)). Alternatively, a C4d polypeptide dimer may comprise two different C4d polypeptides (e.g. a first polypeptide having or consisting of the sequence as depicted in SEQ ID NO:2 (isoform C4d-A(C4Ad)) and a second polypeptide having or consisting of the sequence as depicted in SEQ ID NO: 4 (isoform C4d-B(C4Bd)) or e.g a first polypeptide having or consisting of the sequence as depicted in SEQ ID NO:4 (isoform C4d-B(C4Bd)) and a second polypeptide having or consisting of the sequence as depicted in SEQ ID NO: 2 (isoform C4d-A(C4Ad))).

Further combinations of C4d polypeptides (or a functional fragment or derivative thereof) as defined herein in any order in C4d (polypeptide) multimers can easily be imagined and are within the scope of the present invention. Accordingly, and in the context of the invention, the order of the herein defined "first" and "second" (or "third" etc.) C4d polypeptide (or functional fragment or derivative thereof) may be arranged in an order. For example, said "first polypeptide" may be located at the amino (N-) terminus and said "second polypeptide" may be located at the carboxy (C-) terminus of the C4d multimer. However, this order may also be reversed, e.g. said "first polypeptide" is located at the carboxy (C-) terminus and said "second polypeptide" is located at the amino (N-) terminus of the of the C4d multimer. If the C4d multimer comprises/consists only of one first C4d polypeptide and one second C4d polypeptide, the domain order may, accordingly, be (from N-terminus to C-terminus): first C4d polypeptide—second C4d polypeptide. Vice versa, the domain order may be (from N-terminus to C-terminus): second C4d polypeptide—first C4d polypeptide.

The C4d multimers may be produced by recombinant expression of only one C4d polypeptides (or a functional fragment or derivative thereof) (e.g. by taking advantage of a nucleic acid molecules encoding a C4d polypeptide monomer (or a functional fragment or derivative thereof)). Such recombinant C4d polypeptide monomers may then be conjugated or linked to form C4d multimers, e.g. via biotinylation as exemplified in the appended example. Various methods for protein multimerization have been described and are known in the art. Pentamerization of C4d can be accomplished by fusing coiled-coil domains (Terskikh et al, PNAS, 1997, 94; 1663) or the secretory tailpiece of human IgM (Sorensen et al, J. Immunol. 1996; 156; 2858) to C4d molecules. Dimerization is achieved f.i. by generating immunoglobulin fusion proteins whereby a C4d is fused to the hinge region and $C_H2$ and $C_H3$ domains of human IgG1. Another possibility is to link several C4d molecules via a dextran-backbone (Batard et al., J. Immunol. Meth. 2006; 310; 136).

Preferably, the nucleic acid molecule of the invention is comprised in a recombinant vector in which a nucleic acid molecule encoding the herein described C4d polypeptide(s) (or a functional fragment or derivative thereof)/C4d multimers comprising one or more C4d polypeptides (or a functional fragment or derivative thereof) is operatively linked to expression control sequences allowing expression in prokaryotic or eukaryotic cells. Expression of said nucleic acid molecule comprises transcription of the nucleic acid molecule into a translatable mRNA. Regulatory elements permitting expression in prokaryotic host cells comprise, e.g., the lambda PL, lac, trp, tac, ara, phoA, tet or T7 promoters in E. coli. Possible regulatory elements ensuring expression in eukaryotic cells, preferably mammalian cells or yeast, are well known in the art. They usually comprise regulatory sequences ensuring initiation of transcription and optionally poly-A signals effecting termination of transcription and stabilization of the transcript. Additional regulatory elements may include transcriptional as well as translational enhancers, and/or naturally associated or heterologous promoter regions. Examples for regulatory elements permitting expression in eukaryotic host cells are the AOX1 or GAL1 promoters in yeast or the CMV, SV40, RSV (Rous sarcoma virus) promoters, CMV enhancer, SV40 enhancer or a globin intron in mammalian and other animal cells. Apart from elements which are responsible for the initiation of transcription such regulatory elements may also comprise transcription termination signals, such as the SV40-poly-A site or the tk-poly-A site, downstream of the coding region.

Methods which are well known to those skilled in the art can be used to construct recombinant vectors (see, for example, the techniques described in Sambrook (1989), Molecular Cloning: A Laboratory Manual, Cold Spring Harbor Laboratory NY and Ausubel (1989), Current Protocols in Molecular Biology, Green Publishing Associates and Wiley Interscience, NY). In this context, suitable expression vectors are known in the art such as Okayama-Berg cDNA expression vector pcDV1 (Pharmacia), pCDM8, pRc/CMV, pcDNA1, pcDNA3, pPICZalpha A (Invitrogen), or pSPORT1 (GIBCO BRL). Furthermore, depending on the expression system that is used, leader sequences capable of directing the polypeptide to a cellular compartment or secreting it into the culture medium may be added to the coding sequence of the nucleic acid molecule of the invention.

The present invention also relates to vectors, particularly plasmids, cosmids, viruses, and bacteriophages that are conventionally employed in genetic engineering, comprising a nucleic acid molecule encoding the C4d polypeptide(s) (or a functional fragment or derivative thereof)/C4d multimers comprising one or more C4d polypeptides (or a functional fragment or derivative thereof) of the invention. Preferably, said vector is an expression vector and/or a gene transfer or targeting vector. Expression vectors derived from viruses such as retroviruses, vaccinia virus, adeno-associated virus, herpes viruses or bovine papilloma virus may be used for delivery of the polynucleotides or vector of the invention into targeted cell populations.

The vectors containing the nucleic acid molecules of the invention can be transfected into the host cell by well known methods, which vary depending on the type of cell. Accordingly, the invention further relates to a cell comprising said nucleic acid molecule or said vector. Such methods, for example, include the techniques described in Sambrook (1989), loc. cit. and Ausubel (1989), loc. cit. Accordingly, calcium chloride transfection or electroporation is commonly utilized for prokaryotic cells, whereas calcium phosphate treatment or electroporation may be used for other cellular hosts (Sambrook (1989), loc. cit.). As a further alternative, the nucleic acid molecules and vectors of the invention can be reconstituted into liposomes for delivery to target cells. The nucleic acid molecule or vector of the invention which is present in the host cell may either be integrated into the genome of the host cell or it may be maintained extra-chromosomally. Accordingly, the present invention also relates to a host cell comprising the nucleic acid molecule and/or the vector of this invention. Host cells for the expression of polypeptides are well known in the art and comprise prokaryotic cells as well as eukaryotic cells, e.g. E. coli cells, yeast cells, invertebrate cells, CHO cells, CHO-K1 cells, HEK 293 cells, Hela cells, COS-1 monkey cells, melanoma cells such as Bowes cells, mouse L-929 cells, 3T3 cell lines derived from Swiss, Balb-c or NIH mice, BHK or HaK hamster cell lines and the like. Production in cells of mammalian origin is preferred, if glycosylation of the polypeptide is desired.

In a further aspect, the present invention comprises methods for the preparation of the C4d polypeptide(s) (or a functional fragment or derivative thereof)/C4d multimers comprising one or more C4d polypeptides (or a functional fragment or derivative thereof) comprising culturing the (host) cell of this invention and isolating said C4d polypeptide(s) (or a functional fragment or derivative thereof)/C4d multimers comprising one or more C4d polypeptides (or a functional fragment or derivative thereof) from the culture as described herein. In general, the C4d polypeptide(s) (or a functional fragment or derivative thereof)/C4d multimers comprising one or more C4d polypeptides (or a functional fragment or derivative thereof) may be produced by recombinant DNA technology, e.g. by cultivating a cell comprising the described nucleic acid molecule or vectors which encode the inventive C4d polypeptide(s) (or a functional fragment or derivative thereof)/C4d multimers comprising one or more C4d polypeptides (or a functional fragment or derivative thereof) and isolating said C4d polypeptide(s) (or a functional fragment or derivative thereof)/C4d multimers comprising one or more C4d polypeptides (or a functional fragment or derivative thereof) from the culture. The inventive C4d polypeptide(s) (or a functional fragment or derivative thereof)/C4d multimers comprising one or more C4d polypeptides (or a functional fragment or derivative thereof) may be produced in any suitable cell culture system including prokaryotic cells, e.g. *E. coli* BL21, KS272 or JM83, or eukaryotic cells, e.g. *Pichia pastoris*, yeast strain X-33 or CHO cells. Further suitable cell lines known in the art are obtainable from cell line depositories like the American Type Culture Collection (ATCC).

The term "prokaryotic" is meant to include bacterial cells while the term "eukaryotic" is meant to include yeast, higher plant, insect and mammalian cells. The transformed hosts can be grown in fermentors and cultured according to techniques known in the art to achieve optimal cell growth. In a further embodiment, the present invention relates to a process for the preparation of a C4d polypeptide(s) (or a functional fragment or derivative thereof)/C4d multimers comprising one or more C4d polypeptides (or a functional fragment or derivative thereof) described above comprising cultivating a cell of the invention under conditions suitable for expression of the C4d polypeptide(s) (or a functional fragment or derivative thereof)/C4d multimers comprising one or more C4d polypeptides (or a functional fragment or derivative thereof) and isolating said protein/polypeptide from the cell or the culture medium.

The C4d polypeptide(s) (or a functional fragment or derivative thereof)/C4d multimers comprising one or more C4d polypeptides (or a functional fragment or derivative thereof) as provided herein may comprise a chemically reactive group, for example when said C4d polypeptide is part of a "fusion protein"/"fusion construct". As also described above, the C4d polypeptide can be prepared by recombinant expression in a transformed cell in several ways according to methods well known to the person skilled in the art, for example: (i) direct expression in the cytoplasm with the help of an N-terminal Met residue/start codon; (ii) secretion via an N-terminal signal peptide, for example OmpA, PhoA (Monteilhet (1993) Gene. 1993 125:223-228), mellitin (Tessier (1991) Gene 98: 177-183), interleukin 2 (Zhang (2005) J Gene Med 7: 354-365), hGH (Pecceu (1991) Gene 97(2):253-258) and the like, followed by intracellular cleavage resulting in the mature N-terminus, such as Ala or Pro; (iii) expression as a fusion protein with another soluble protein, e.g., maltose-binding protein at the N-terminus and with a protease cleavage site interspersed (Kapust and Waugh (2000) Protein Expr. Purif. 19:312-318), followed by specific protease cleavage in vitro or in vivo, thus releasing the amino acid polymer/polypeptide with its mature N-terminus such. Another suitable fusion partner is the SUMO protein, which can be cleaved by SUMO protease. Further fusion partners include, without limitation, glutathion-S-transferase, thioredoxin, a cellulose-binding domain, an albumin-binding domain, a fluorescent protein (such as GFP), protein A, protein G, an intein and the like (Malhotra (2009) Methods Enzymol. 463:239-258).

With the means and methods provided herein it is now possible to manufacture and provide for the herein disclosed (i) C4d polypeptide(s) (or a functional fragment or derivative thereof)/C4d multimers comprising one or more C4d polypeptides (or a functional fragment or derivative thereof) and (ii) peptides/proteins comprising said C4d polypeptide(s) and/or C4d (polypeptide) multimers which comprise (a) further molecule(s) of interest, like a useful protein, a protein segment or a small molecule. Accordingly, the present invention also provides for a method for the preparation and/or manufacture of a C4d polypeptide(s) (or a functional fragment or derivative thereof)/C4d multimers comprising one or more C4d polypeptides (or a functional fragment or derivative thereof) as comprised in conjugates, like drug conjugates.

These methods, comprise (as one step) the cultuvation of the (host) cell as provided herein above and (as a further step) the isolation of said C4d polypeptide(s) (or a functional fragment or derivative thereof)/C4d multimers comprising one or more C4d polypeptides (or a functional fragment or derivative thereof) and/or polypeptide conjugate from the culture or from said cell. This isolated C4d polypeptide(s) (or a functional fragment or derivative thereof)/C4d multimers comprising one or more C4d polypeptides (or a functional fragment or derivative thereof) as well as the isolated conjugate may than be further processed. For example, said C4d polypeptide(s) (or a functional fragment or derivative thereof)/C4d multimers comprising one or more C4d polypeptides (or a functional fragment or derivative thereof) or conjugate may be chemically linked or coupled to a molecule of interest. Furthermore and as an alternative, the molecule of interest may be enzymatically conjugated e.g. via transglutaminase (Besheer (2009) J Pharm Sci. 98:4420-8) or other enzymes (Subul (2009) Org. Biomol. Chem. 7:3361-3371) to said C4d polypeptide(s) (or a functional fragment or derivative thereof)/C4d multimers comprising one or more C4d polypeptides (or a functional fragment or derivative thereof) or conjugate.

The C4d polypeptide(s) (or a functional fragment or derivative thereof)/C4d multimers comprising one or more C4d polypeptides (or a functional fragment or derivative thereof) or conjugate comprising same can be isolated (inter alia) from the growth medium, cellular lysates, periplasm or cellular membrane fractions. The isolation and purification of the expressed polypeptides of the invention may be performed by any conventional means (Scopes (1982) "Protein Purification", Springer, New York, N.Y.), including ammonium sulphate precipitation, affinity purification, column chromatography, gel electrophoresis and the like and may involve the use of monoclonal or polyclonal antibodies directed, e.g., against a tag fused with the C4d polypeptide/C4d multimer(s) of the invention. For example, the protein can be purified via the Strep-tag II using streptavidin affinity chromatography. Substantially pure polypeptides of at least about 90 to 95% homogeneity (on the protein level) are preferred, and 98 to 99% or more homogeneity are most preferred, in particular for pharmaceutical use/applications. Depending upon the host cell/organism employed in the production procedure, the polypeptides of the present invention may be glycosylated or may be non-glycosylated.

As mentioned above, the C4d polypeptide(s) (or a functional fragment or derivative thereof)/C4d multimers comprising one or more C4d polypeptides (or a functional fragment or derivative thereof) may comprise additional amino acid stretches which may, as such, not contribute to the biological activity (like attenuation of a pro-inflammatory response) of the herein provided polypeptides. The further amino acid sequences/amino acid residues may, for example, be useful as linkers. As explained above, inter alia, dimers, trimers, i.e. in general multimers of the C4d polypeptide(s) (or a functional fragment or derivative thereof) are envisaged in context of the present invention and such multimers may be linked by amino acid sequences/residues. Such peptide linkers would preferentially be composed of flexible residues like glycine or serine and could have different length preferentially between 5 and 15 amino acids. A peptide with the amino acid sequence GGGSGGGSGGGS would be an example for a flexible linker that could be used.

Furthermore, a drug conjugate is provided which comprises the herein described and defined C4d polypeptide(s) (or a functional fragment or derivative thereof)/C4d multimers comprising one or more C4d polypeptides (or a functional fragment or derivative thereof) and a small molecule drug that is conjugated to said C4d polypeptide(s) (or a functional fragment or derivative thereof)/C4d multimers comprising one or more C4d polypeptides (or a functional fragment or derivative thereof).

A site-specific conjugation of the N-terminus of the C4d polypeptide(s) (or a functional fragment or derivative thereof)/C4d multimers comprising one or more C4d polypeptides (or a functional fragment or derivative thereof) with an activated drug derivative, e.g. as N-hydroxysuccinimide (NHS) ester derivative (Hermanson (1996) Bioconjugate Techniques, Academic Press, San Diego, Calif.), is possible. Generally, the N-terminal amino group can be chemically coupled with a wide variety of functional groups such as aldehydes and ketones (to form Schiff bases, which may be reduced to amines using sodium borohydride or sodium cyanoborohydride, for example) or to activated carbonic acid derivatives (anhydrides, chlorides, esters and the like, to form amides) or to other reactive chemicals such as isocyanates, isothiocyanates, sulfonly chlorides etc. Also, the N-terminus of the polypeptide can first be modified with a suitable protective group, for example an acetyl group, a BOC group or an FMOC group (Jakubke (1996) Peptide. Spektrum Akdemischer Verlag, Heidelberg, Germany). Furthermore, the amino terminus may be protected by a pyroglutamyl group, which can form from an encoded Gln amino acid residue. After activation of the C-terminal carboxylate group, e.g. using the common reagents EDC (N-(3-dimethylaminopropyl)-N'-ethylcarbodiimide) and NHS, site-specific coupling to the C-terminus of the protected C4d polypeptide(s) (or a functional fragment or derivative thereof)/C4d multimers comprising one or more C4d polypeptides (or a functional fragment or derivative thereof) can be achieved if the drug carries a free amino group, for example.

Alternatively, the N-terminus or the C-terminus of the C4d polypeptide(s) (or a functional fragment or derivative thereof)/C4d multimers comprising one or more C4d polypeptides (or a functional fragment or derivative thereof) can be modified with a commercially available linker reagent providing a maleimide group, thus allowing chemical coupling to a thiol group as part of the drug molecule. In this manner uniform drug conjugates can be easily obtained. Similar techniques, which are well known in the art (Hermanson (1996) loc. cit.), can be used to couple C4d polypeptide(s) (or a functional fragment or derivative thereof)/C4d multimers comprising one or more C4d polypeptides (or a functional fragment or derivative thereof) to a peptide or even to a protein drug. Such peptides or proteins can easily be prepared carrying a Lys or Cys side chain, which allows their in vitro coupling to the C4d polypeptide(s) (or a functional fragment or derivative thereof)/C4d multimers comprising one or more C4d polypeptides (or a functional fragment or derivative thereof) via NHS ester or maleimide active groups. Generally, similar drug conjugates can be prepared with fusion proteins comprising C4d polypeptide(s) (or a functional fragment or derivative thereof)/C4d multimers comprising one or more C4d polypeptides (or a functional fragment or derivative thereof).

As an alternative to a single site-specific conjugation, the C4d polypeptide(s) (or a functional fragment or derivative thereof)/C4d multimers comprising one or more C4d polypeptides (or a functional fragment or derivative thereof) may be equipped with additional side chains, at the N- or C-terminus or internally, suitable for chemical modification such as lysine residues with their ε-amino groups, cysteine residues with their thiol groups, or even non-natural amino acids, allowing the conjugation of multiple small molecules using, for example, NHS ester or maleimide active groups.

Apart from stable conjugation, a prodrug may be linked transiently to the C4d polypeptide(s) (or a functional fragment or derivative thereof)/C4d multimers comprising one or more C4d polypeptides (or a functional fragment or derivative thereof). The linkage can be designed to be cleaved in vivo, in a predictable fashion, either via an enzymatic mechanism or by slow hydrolysis initiated at physiological pH. Furthermore, the small molecule may be coupled to a fusion protein comprising the C4d polypeptide(s) (or a functional fragment or derivative thereof)/C4d multimers comprising one or more C4d polypeptides (or a functional fragment or derivative thereof) genetically fused to a targeting domain, e.g. an antibody fragment, thus resulting in a specific delivery of the small molecule drug.

The following relates to exemplary protocols for the generation of complement split product C4d multimers to be used in accordance with the present invention, for example in the treatment of graft rejection, graft versus host disease, rheumatoid arthritis and (systemic) lupus erythematosus.

Method 1.: Generation of Divalent Recombinant Human C4d-IgG1-Fc-Fusion Proteins ("C4Ad-IgG1-Fc"-Fusion Protein and "C4B d-IgG1-Fc"-Fusion Protein) Including C4d-IgG1-Fc-Fusion Proteins Optimized for Fc-Mediated Effector Functions, e.g. Fc Sequence Engineering for Silenced/Immunosuppressive Effector Functionality as Described in Strohl W R. (Optimization of Fc-Mediated Effector Functions of Monoclonal Antibodies. Curr Opin Biotechnol 2009; 20 (6): 685), which is Incorporated Herein by Reference.

Exemplary Sequence of C4Ad-Immunoglobulin G1 Fusion Protein (C4Ad-IgG1-Fc):

HumanCD5 Signalsequence (aa 1-25)-humanC4Ad (aa26-405)-Glycinlinker-humanIgG1 from hinge region:

MPMGSLQPLATLYLLGMLVASCLGTLEIPGNSDPNMIPDGDFNSYVRVTA

SDPLDTLGSEGALSPGGVASLLRLPRGCGEQTMIYLAPTLAASRYLDKTE

QWSTLPPETKDHAVDLIQKGYMRIQQFRKADGSYAAWLSRDSSTWLTAFV

LKVLSLAQEQVGGSPEKLQETSNWLLSQQQADGSFQDPCPVLDRSMQGGL

VGNDETVALTAFVTIALHHGLAVFQDEGAEPLKQRVEASISKANSFLGEK

ASAGLLGAHAAAITAYALTLTKAPVDLLGVAHNNLMAMAQETGDNLYWGS

VTGSQSNAVSPTPAPRNPSDPMPQAPALWIETTAYALLHLLLHEGKAEMA

DQAAAWLTRQGSFQGGFRSTQDTVIALDALSAYWIASHTTEERGLNVTLS

STGR<u>GGGDPEGDPKSCDKTHTCPPCPAPELLGGPSVFLFPPKPKDTLMIS</u>

<u>RTPEVTCVVVDVSHEDPEVKFNWYVDGVEVHNAKTKPREEQYNSTYRVVS</u>

<u>VLTVLHQDWLNGKEYKCKVSNKALPAPIEKTISKAKGQPREPQVYTLPPS</u>

<u>RDELTKNQVSLTCLVKGFYPSDIAVEWESNGQPENNYKTTPPVLDSDGSF</u>

<u>FLYSKLTVDKSRWQQGNVFSCSVMHEALHNHYTQKSLSLSPGK</u>

Exemplary Sequence of C4Bd-Immunoglobulin G1 Fusion Protein (C4Bd-IgG1-Fc):

HumanCD5 Signalsequence (aa 1-25)-humanC4Bd (aa26-405)-Glycinlinker-humanIgG1 from hinge region:

MPMGSLQPLATLYLLGMLVASCLGTLEIPGNSDPNMIPDGDFNSYVRVTA

SDPLDTLGSEGALSPGGVASLLRLPRGCGEQTMIYLAPTLAASRYLDKTE

QWSTLPPETKDHAVDLIQKGYMRIQQFRKADGSYAAWLSRDSSTWLTAFV

LKVLSLAQEQVGGSPEKLQETSNWLLSQQQADGSFQDLSPVIHRSMQGGL

VGNDETVALTAFVTIALHHGLAVFQDEGAEPLKQRVEASISKANSFLGEK

ASAGLLGAHAAAITAYALTLTKAPVDLLGVAHNNLMAMAQETGDNLYWGS

VTGSQSNAVSPTPAPRNPSDPMPQAPALWIETTAYALLHLLLHEGKAEMA

DQAAAWLTRQGSFQGGFRSTQDTVIALDALSAYWIASHTTEERGLNVTLS

STGRGGGDPEGDPKSCDKTHTCPPCPAPELLGGPSVFLFPPKPKDTLMIS

RTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSF

FLYSKLTVDKSRWQQGNVFSCSVMHEALHNHYTQKSLSLSPGK

This method provides for C4d dimers. To this end, fusion proteins of C4d polypeptides as provided and defined herein with IgG1-Fc are generated (an exemplary IgG1-Fc sequence to be used herein is underlined in the above fusion proteins). C4d dimers are generated by dimerization of the individual C4d-IgG1-Fc-fusion proteins via the IgG1-Fc-part (which forms disulfide bonds). Because also C4d polypeptides inherently are prone to form disulfide bonds via cysteine residues, large complexes of C4d-IgG1-Fc-fusion proteins might be generated. Because such large complexes of many C4d-IgG1-Fc-fusion proteins are believed to be undesirable for therapeutic purposes, the cysteines of the C4d polypeptides are inactivated, thereby reducing or eliminating the probability of formation of disulfide bonds. This is explained in more detail below.

Human C4d contains one cysteine located in the thioester region, which in recombinant C4d is a free cysteine. This is true for recombinant C4d of both C4d isoforms (C4Ad and C4Bd) as defined herein. However, besides the thioester cysteine in C4Ad and C4Bd, C4d of the C4A isotype has got one additional free cysteine located in the isotypic sequence (PCPVLD), which increases the odds for disulfide-linked dimer formation between single C4d molecules, this C4d-C4d dimer-formation might occur between the two C4d-molecules of a C4d-IgG1-Fc fusion dimer protein as well as between C4d-molecules of distinct C4d-IgG1-Fc fusion dimer proteins, the latter potentially resulting in large complexes of C4d-IgG1-Fc fusion proteins. Both types of dimer- (or multimer) formation might interfere with the ability of the recombinant C4d molecules to interact with their cellular receptors, thus, potentially compromising the conferral of the desired therapeutic (immunomodulatory) effects. Therefore, the formation of disulphide-linked C4d-dimers ought to be precluded.

There are two distinct methods allowing for the preclusion of C4d-C4d disulfide bridge-formation:

a) The first method represents the irreversible functional inactivation of the cysteine(s) by chemical reduction followed by alkylation. Mild reduction of cysteines can be achieved by adding DTT (e.g. 5 mM final concentration, pH 8) to a solution of C4d (e.g. in PBS, pH 8) in the absence of any denaturing agents and incubating the reaction for one hour at 20° C. This will lead to the selective reduction of the disulfide bonds of the IgG1 hinge-region as well as any potential C4d-C4d disulfide bridges, without affecting the intrachain disulfide bonds of the CH2 and CH3 domains of the IgG1-Fc region, as in the absence of any denaturing agent the intrachain disulfide bonds will not be accessible to reduction in aqueous buffers. After one hour of incubation at 20° C., the reduced thiol-groups can be alkylated by applying a slight excess of iodoacetamide (e.g. 15 mM) and incubating the reaction for 20 minutes at 20° C. Alkylation of the cysteins prevents any re-oxidation and, thus, any C4d-C4d-disulfide bridge formation. The low molecular weight reagents can be removed either by dialysis or other methods of buffer exchange, e.g. desalting procedures.

b) As a second method the exchange of the cystein(s) contained in the C4Ad (thioestersequence and isotypic sequence) or C4Bd (thioestersequence, e.g. for alanine(s)) molecules through genetic engineering, will primarily preclude C4d-C4d-disulfide bridge formation.

Method 2.: Monomeric Recombinant Human C4d Multimerized by Covalent Attachment to Multivalent Crosslinkers The recombinant human C4Ad and C4Bd molecules used in this approach have already been described herein and also in detail in (2), (3). The sequences of these C4d molecules correspond to the sequences of C4d generated during physiologic cleavage of C4b via factor I (referred to as "C4Adg" or "C4Bdg" in (2), (3)) with intact cysteine(s).

2. Clemenza L, Isenman D E. The C4A and C4B isotypic forms of human complement fragment C4b have the same intrinsic affinity for complement receptor 1 (CR1/CD35). J Immunol 2004; 172 (3): 1670.

3. van den Elsen J M, Martin A, Wong V, Clemenza L, Rose D R, Isenman D E. X-ray crystal structure of the C4d fragment of human complement component C4. J Mol Biol 2002; 322 (5): 1103.

Two exemplary methods to covalently attach monomeric recombinant human C4d to commercially available multivalent crosslinkers can be used in accordance with the present invention.

The first method takes advantage of sulfhydryl-specific crosslinking.

Sulfhydryl-specific crosslinking based on crosslinkers containing either two or three maleimide reactive groups for selective covalent interaction with protein thiols (reduced cysteines) to form stable thioesther bonds. These crosslinkers allow for the single C4d molecules to be exposed in their physiologic conformation (via thioester).

Two suitable sulfhydryl-specific crosslinkers are offered by PIERCE, Thermo Fisher Scientific, Rockford, Ill., USA:

1) BM(PEG)3 (1,11-Bismaleimido-triethyleneglycol) (Cat. No. 22337) of PIERCE, Thermo Fisher Scientific, Rockford, Ill., USA:

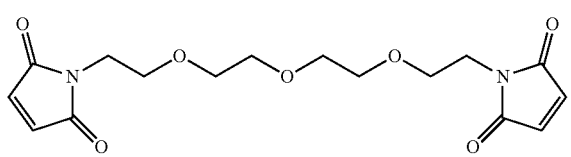

BM(PEG)3
1,11-Bismaleimidotriethyleneglycol
MW 352.34
Spacer Arm 17.8 Å

Covalent attachment of C4d to the divalent PEGylated crosslinker "BM(PEG)3" can be performed as exemplified in the manufacturer's instructions described in detail as follows (adapted from http://www.piercenet.com/instructions/2160786.pdf):

Materials

Conjugation Buffer: Phosphate buffered saline (PBS, pH 7.2) or other sulfhydryl-free buffer at pH 6.5-7.5. Include 5-10 mM EDTA to help prevent the reoxidation of disulfides by trace divalent metals.

Crosslinker Stock Solution: Immediately before use, weigh a small quantity of crosslinker and dissolve it in dimethylformamide (DMF) or dimethylsulfoxide (DMSO) at a 5-20 mM concentration (e.g., make a 20 mM solution of BM(PEG)3 by dissolving 3.5 mg reagent in 0.5 mL DMF or DMSO). Alternatively, the reagent can be dissolved at <10 mg/mL in warm (37° C.) water in about 10 minutes. Warming the crosslinker will not affect the integrity of the maleimide groups.

Sulfhydryl-containing protein: C4Ad or C4Bd-molecules to be reacted with maleimide compounds must have free (reduced) sulfhydryls. Peptide disulfide bonds can be reduced with Thermo Scientific Immobilized TCEP Disulfide Reducing Gel (Product No. 77712). Extraneous sulfhydryl-containing components in the reaction buffers during conjugation should be avoided (e.g., DTT), as they react with the maleimide portion of the reagent, inhibiting and reducing conjugation efficiency of the intended target. The maleimide group reacts predominantly with free sulfhydryls at pH 6.5-7.5, forming stable thioester bonds. At pH values >7.5, reactivity toward primary amines and hydrolysis of the maleimide groups can occur. At pH 7, the maleimide group is ~1000 times more reactive toward a free sulfhydryl than to an amine.

Avoid sulfhydryl-containing components during conjugation, as these will react with the maleimide portion of the reagent, thereby inhibiting and reducing conjugation efficiency of the intended molecule.

Desalting column (e.g., Zeba™ Spin Desalting Columns) or dialysis unit to separate crosslinked proteins from excess nonreacted crosslinker.

Example for C4d Crosslinking Procedure

1. C4Ad or C4Bd is incubated in Conjugation Buffer at about 0.1 mM.
2. Crosslinker is added to the dissolved protein(s) at about 0.05 mM final concentration
   i.e. about two-fold molar excess of C4d as compared to the divalent crosslinker
   to avoid possible damage to the protein, the amount of organic solvent should be limited to ≤10% in the final reaction mixture.
3. Reaction mixture can be incubated for 1 hour at room temperature or for 2 hours at 4° C.
4. Reaction can be stopped by the removal of excess nonreacted reagent by desalting or dialysis.

2.) TMEA (Tris(2-maleimidoethyl)amine) (Cat. No. 33043) of PIERCE, Thermo Fisher Scientific, Rockford, Ill., USA:

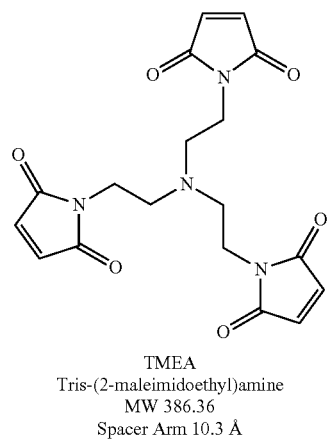 [SMILES: O=C1C=CC(=O)N1CCN(CCN1C(=O)C=CC1=O)CCN1C(=O)C=CC1=O]

TMEA
Tris-(2-maleimidoethyl)amine
MW 386.36
Spacer Arm 10.3 Å

Covalent attachment of C4d to the trivalent crosslinker "TMEA" can be performed as exemplified in the manufacturer's instructions described in detail as follows (adapted from http://www.piercenet.com/instructions/2160800.pdf)

Materials

Conjugation Buffer: Phosphate buffered saline (PBS, pH 7.2) or other sulfhydryl-free buffer at pH 6.5-7.5. Include 5-10 mM EDTA to help prevent the reoxidation of disulfides by trace divalent metals.

Crosslinker Stock Solution: TMEA dissolves in DMF or DMSO up to 10 mg/100 μL (i.e., 100 mg/mL). A working stock solution at 1-100 mg/mL can be diluted in additional organic solvent. To avoid possible damage to the protein, limit the amount of organic solvent to ≤10% in the final reaction mixture.

Sulfhydryl-containing protein: Maleimides react with SH groups at a pH of 6.5-7.5, forming stable thioester linkages. The reaction is complete in 2 hours at room temperature or ~4 hours at 4° C.

Sulfhydryl-containing protein: C4Ad or C4Bd-molecules to be reacted with maleimide compounds must have free (reduced) sulfhydryls. Peptide disulfide bonds can be reduced with Thermo Scientific Immobilized TCEP Disulfide Reducing Gel (Product No. 77712). Extraneous sulfhydryl-containing components in the reaction buffers during conjugation should be avoided (e.g., DTT), as they react with the maleimide portion of the reagent, inhibiting and reducing conjugation efficiency of the intended target. The maleimide group reacts predominantly with free sulfhydryls at pH 6.5-7.5, forming stable thioester bonds. At pH values >7.5, reactivity toward primary amines and hydrolysis of the maleimide groups can occur. At pH 7, the maleimide group is ~1000 times more reactive toward a free sulfhydryl than to an amine.

Avoid sulfhydryl-containing components during conjugation, as these will react with the maleimide portion of the reagent, thereby inhibiting and reducing conjugation efficiency of the intended molecule.

Desalting column (e.g., Zeba™ Spin Desalting Columns) or dialysis unit to separate crosslinked proteins from excess nonreacted crosslinker.

Example for C4d Crosslinking procedure
1. C4Ad or C4Bd is incubated in Conjugation Buffer at about 0.1 mM.
2. Crosslinker is added to the dissolved protein(s) at about 0.03 mM final concentration
   i.e. about three-fold molar excess of C4d as compared to the trivalent crosslinker
   to avoid possible damage to the protein, the amount of organic solvent should be limited to <10% in the final reaction mixture.
3. Reaction mixture can be incubated for 1 hour at room temperature or for 2 hours at 4° C.
4. Reaction can be stopped by the removal of excess nonreacted reagent by desalting or dialysis.

The second method takes advantage of amine-specific crosslinking

Amine-specific crosslinking based on crosslinkers containing either two or three reactive N-hydroxysuccinimide ester (NHS ester) for selective covalent interaction with primary amines to form stable complexes. These crosslinkers bind C4d molecules in a random fashion, thus, allowing for a variety of different conformations.

1.) BS(PEG)5 (Bis(succinimidyl) penta(ethylene glycol) (Cat. No. 21581) of PIERCE, Thermo Fisher Scientific, Rockford, Ill., USA:

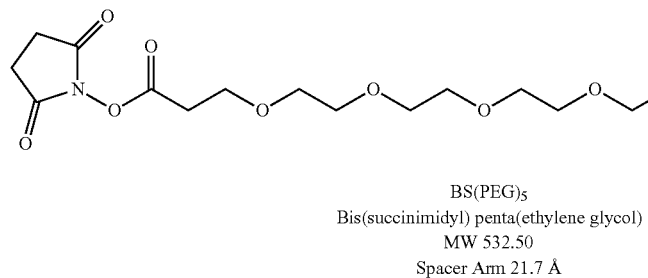

BS(PEG)₅
Bis(succinimidyl) penta(ethylene glycol)
MW 532.50
Spacer Arm 21.7 Å

Covalent attachment of C4d to the divalent PEGylated crosslinker "BS(PEG)5" can be performed as exemplified in the manufacturer's instructions described in detail as follows (adapted from http://www.piercenet.com/instructions/2161765.pdf)

Materials

Conjugation Buffer: Conjugation Buffer: Phosphate-buffered saline (PBS, pH 7.2) or other amine-free buffer (e.g. carbonate/bicarbonate, HEPES and borate buffers) at pH 7-8.

Crosslinker Stock Solution: BS(PEG)5 reagent is a viscous pale liquid that is difficult to weigh and dispense. To facilitate handling, a stock solution should be made immediately before first use by dissolving the crosslinker in dry (anhydrous, molecular sieve-treated) organic solvent, such as dimethylsulfoxide (DMSO). Reagent exposure to moisture should be minimized because the NHS-ester reactive group is susceptible to hydrolysis. Unused stock solution should be stored in a moisture-free condition (e.g., capped under an inert gas such as argon or nitrogen) at −20° C., and reagent vial should be equilibrated to room temperature before opening to avoid moisture condensation inside the container. Exposure to air should be minimized.

A 250 mM Crosslinker Stock Solution can be prepared by dissolving 100 mg of BS(PEG)5 (i.e. entire contents of vial, ~100 μL) in following ~650 μL of dry DMSO to make 7500 μL total.

Buffers containing primary amines (e.g., Tris or glycine) during conjugation should be avoided because they will compete with the intended reaction.

Desalting column (e.g., Zeba™ Spin Desalting Columns) or dialysis unit to separate crosslinked proteins from excess nonreacted crosslinker.

Example for C4d Crosslinking Procedure
1. C4Ad or C4Bd is incubated in Conjugation Buffer at about 0.1 mM.
2. Crosslinker is added to the dissolved protein at about 0.05 mM final concentration
   i.e. two-fold molar excess of C4d as compared to the divalent crosslinker to generate small C4Bd S(PEG)5 complexes, or
Crosslinker is added to the dissolved protein(s) in excess (e.g. at up to 1 mM final concentration)
   i.e. up to ten-fold molar excess of crosslinker to generate larger complexes
   to avoid possible damage to the protein, the amount of organic solvent should be limited to ≤10% in the final reaction mixture.
3. Reaction mixture can be incubated for 1 hour at room temperature or for 2 hours at 4° C.
4. Reaction can be stopped by the removal of excess non-reacted reagent by desalting or dialysis.

2.) TSAT (Tris-succinimidyl aminotriacetate) (Cat. No. 33063) of PIERCE, Thermo Fisher Scientific, Rockford, Ill., USA:

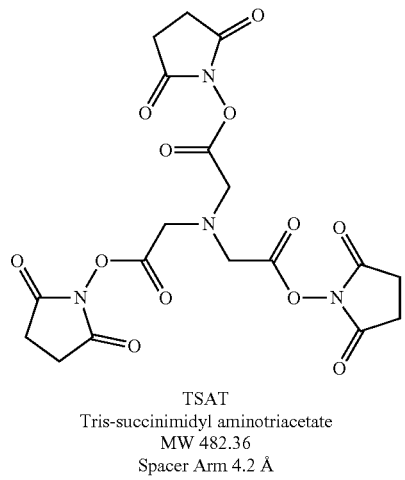 [SMILES: O=C(CN(CC(=O)ON1C(=O)CCC1=O)CC(=O)ON1C(=O)CCC1=O)ON1C(=O)CCC1=O]

TSAT
Tris-succinimidyl aminotriacetate
MW 482.36
Spacer Arm 4.2 Å

Covalent attachment of C4d to the trivalent crosslinker "TSAT" can be performed as exemplified in the manufacturer's instructions described in detail as follows (adapted from http://www.piercenet.com/instructions/2160860.pdf)

Materials

Conjugation Buffer: Phosphate-buffered saline (PBS, pH 7.2) or other amine-free buffer (e.g. carbonate/bicarbonate, HEPES and borate buffers) at pH 7-8.

Crosslinker Stock Solution: TSAT reagent is moisture-sensitive; the NHS ester moiety readily hydrolyzes and becomes non-reactive. Therefore, stock solutions cannot be prepared for storage. To avoid moisture condensation onto the product, vial must be equilibrated to room temperature before opening. Prepare TSAT immediately before use. TSAT is water-insoluble and must first be dissolved in DMSO or DMF and then added to an aqueous reaction medium.

Buffers containing primary amines (e.g., Tris or glycine) during conjugation should be avoided because they will compete with the intended reaction.

Desalting column (e.g., Zeba™ Spin Desalting Columns) or dialysis unit to separate crosslinked proteins from excess nonreacted crosslinker.

Example for C4d Crosslinking procedure

1. C4Ad or C4Bd is incubated in Conjugation Buffer at about 0.1 mM.
2. Crosslinker is added to the dissolved protein at about 0.03 mM final concentration
    i.e. three-fold molar excess of C4d as compared to the trivalent crosslinker to generate small C4Bd S(PEG)5 complexes, or
   Crosslinker is added to the dissolved protein(s) in excess (e.g. at up to 1 mM final concentration)
    i.e. up to ten-fold molar excess of crosslinker to generate larger complexes
   to avoid possible damage to the protein, the amount of organic solvent should be limited to ≤10% in the final reaction mixture.
3. Reaction mixture can be incubated for 1 hour at room temperature or for 2 hours at 4° C.
4. Reaction can be stopped by the removal of excess non-reacted reagent by desalting or dialysis.

The following relates to C4d polypeptide(s) (or a functional fragment or derivative thereof) to be used in accordance with the present invention.

The term "C4d" and "C4d polypeptide" has been described herein above in detail. The terms "complement split product C4d" and "C4d" and the like can be used interchangeably herein.

The meaning of the term "polypeptide" and "nucleic acid sequence(s)/molecule(s)" are well known in the art and are used accordingly in context of the present invention. For example, "nucleic acid sequence(s)/molecule(s)" as used herein refer(s) to all forms of naturally occurring or recombinantly generated types of nucleic acids and/or nucleic acid sequences/molecules as well as to chemically synthesized nucleic acid sequences/molecules. This term also encompasses nucleic acid analogs and nucleic acid derivatives such as e.g. locked DNA, PNA, oligonucleotide thiophosphates and substituted ribo-oligonucleotides. Furthermore, the term "nucleic acid sequence(s)/molecules(s)" also refers to any molecule that comprises nucleotides or nucleotide analogs.

Preferably, the term "nucleic acid sequence(s)/molecule(s)" refers to deoxyribonucleic acid (DNA) and ribonucleic acid (RNA). The "nucleic acid sequence(s)/molecule(s)" may be made by synthetic chemical methodology known to one of ordinary skill in the art, or by the use of recombinant technology, or may be isolated from natural sources, or by a combination thereof. The DNA and RNA may optionally comprise unnatural nucleotides and may be single or double stranded. "Nucleic acid sequence(s)/molecule(s)" also refers to sense and anti-sense DNA and RNA, that is, a nucleotide sequence which is complementary to a specific sequence of nucleotides in DNA and/or RNA.

Furthermore, the term "nucleic acid sequence(s)/molecule(s)" may refer to DNA or RNA or hybrids thereof or any modification thereof that is known in the state of the art (see, e.g., U.S. Pat. No. 5,525,711, U.S. Pat. No. 4,711,955, U.S. Pat. No. 5,792,608 or EP 302175 for examples of modifications). The nucleic acid molecule(s) may be single- or double-stranded, linear or circular, natural or synthetic, and without any size limitation. For instance, the nucleic acid molecule(s) may be genomic DNA, cDNA, mRNA, antisense RNA, ribozymal or a DNA encoding such RNAs or chimeroplasts (Colestrauss, Science (1996), 1386-1389). Said nucleic acid molecule(s) may be in the form of a plasmid or of viral DNA or RNA. "Nucleic acid sequence(s)/molecule(s)" may also refer to (an) oligonucleotide(s), wherein any of the state of the art modifications such as phosphothioates or peptide nucleic acids (PNA) are included.

The nucleic acid sequence of C4d polypeptides of other species than the herein provided human and sequences for C4d polypeptides can be identified by the skilled person using methods known in the art, e.g. by using hybridization assays or by using alignments, either manually or by using computer programs such as those mentioned herein below in connection with the definition of the term "hybridization" and degrees of similarity. The nucleic acid sequence encoding for orthologs of human C4d may be at least 60% similar to the nucleic acid sequence as shown in SEQ ID NO. 1 and SEQ ID NO: 3, respectively. More preferably, the nucleic acid sequence encoding for orthologs of human C4d is at least 65%, 70%, 75%, 80%, 85%, 90%, 91%, 92%, 93%, 94%, 95%, 96%, 97% or 98% similar to the nucleic acid sequence as shown in SEQ ID NO. 1 and SEQ ID NO: 3 respectively, wherein the higher values are preferred. Most preferably, the nucleic acid sequence encoding for orthologs of human C4d is at least 99% similar to the nucleic acid sequence as shown in SEQ ID NO. 1 and SEQ ID NO: 3, respectively. The term "orthologous protein" or "orthologous gene" as used herein refers to proteins and genes, respectively, in different species that are similar to each other because they originated from a common ancestor. As mentioned above, the use of such "orthologous protein(s)" or "orthologous gene(s)/nucleic acid molecules" is envisaged in context of the present invention.

Hybridization assays for the characterization of orthologues of known nucleic acid sequences are well known in the art; see e.g. Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989). The term "hybridization" or "hybridizes" as used herein may relate to hybridizations under stringent or non-stringent conditions. If not further specified, the conditions are preferably non-stringent. Said hybridization conditions may be established according to conventional protocols described, e.g., in Sambrook (2001) loc. cit.; Ausubel (1989) loc. cit., or Higgins and Hames (Eds.) "Nucleic acid hybridization, a practical approach" IRL Press Oxford, Washington D.C., (1985). The setting of conditions is well within the skill of the artisan and can be determined according to protocols described in the art. Thus, the detection of only specifically hybridizing sequences will usually require stringent hybridization and washing conditions such as, for example, the highly stringent hybridization conditions of 0.1×SSC, 0.1% SDS at 65° C. or 2×SSC, 60° C., 0.1% SDS. Low stringent hybridization conditions for the detection of homologous or not exactly complementary sequences may, for example, be set at 6×SSC, 1% SDS at 65° C. As is well known, the length of the probe and the composition of the nucleic acid to be determined constitute further parameters of the hybridization conditions.

In accordance with the present invention, the terms "similarity" or "percent similarity" or "identical" or "percent identity" or "percentage identity" or "sequence identity" ("similar" and "identity" can be used interchangeably herein) in the context of two or more nucleic acid sequences refers to two or more sequences or subsequences that are the same, or that have a specified percentage of nucleotides that are the same (preferably at least 60% identity, more preferably at least 65%, 70%, 75%, 80%, 85%, 90%, 91%, 92%, 93%, 94%, 95%, 96%, 97% or 98% identity, most preferably at least 99% identity), when compared and aligned for maximum correspondence over a window of comparison, or over a designated region as measured using a sequence comparison algorithm as known in the art, or by manual alignment and visual inspection. Sequences having, for example, 75% to 90% or greater sequence identity may be considered to be substantially identical. Such a definition also applies to the complement of a test sequence. Preferably the described identity exists over a region that is at least about 15 to 25 nucleotides in length, more preferably, over a region that is at least about 50 to 100 nucleotides in length and most preferably, over a region that is at least about 800 to 1400 nucleotides in length, or the full length of a sequence as shown in SEQ ID NO: 1 or SEQ ID NO: 3. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art.

Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul, (1997) Nucl. Acids Res. 25:3389-3402; Altschul (1993) J. Mol. Evol. 36:290-300; Altschul (1990) J. Mol. Biol. 215:403-410). The BLASTN program for nucleic acid sequences uses as defaults a word length (W) of 11, an expectation (E) of 10, M=5, N=4, and a comparison of both strands. The BLOSUM62 scoring matrix (Henikoff (1989) PNAS 89:10915) uses alignments (B) of 50, expectation (E) of 10, M=5, N=4, and a comparison of both strands.

In order to determine whether a nucleotide residue in a nucleic acid sequence corresponds to a certain position in the nucleotide sequence of e.g. SEQ ID NO: 1 and SEQ ID NO: 3, respectively, the skilled person can use means and methods well-known in the art, e.g., alignments, either manually or by using computer programs such as those mentioned herein. For example, BLAST 2.0, which stands for Basic Local Alignment Search Tool BLAST (Altschul (1997), loc. cit.; Altschul (1993), loc. cit.; Altschul (1990), loc. cit.), can be used to search for local sequence alignments. BLAST, as discussed above, produces alignments of nucleotide sequences to determine sequence similarity. Because of the local nature of the alignments, BLAST is especially useful in determining exact matches or in identifying similar sequences. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cut-off score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

Analogous computer techniques using BLAST (Altschul (1997), loc. cit.; Altschul (1993), loc. cit.; Altschul (1990), loc. cit.) are used to search for identical or related molecules in nucleotide databases such as GenBank or EMBL. This analysis is much faster than multiple membrane-based hybridizations. In addition, the sensitivity of the computer search can be modified to determine whether any particular match is categorized as exact or similar. The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1-2% error; and at 70, the match will be exact. Similar molecules are usually identified by selecting those which show product scores between 15 and 40, although lower scores may identify related molecules. Another example for a program capable of generating sequence alignments is the CLUSTALW computer program (Thompson (1994) Nucl. Acids Res. 2:4673-4680) or FASTDB (Brutlag (1990) Comp. App. Biosci. 6:237-245), as known in the art.

The explanations and definitions given herein above in respect of "similarity of nucleic acid sequences" apply, mutatis mutandis, to "amino acid sequences", in particular an amino acid sequence as depicted in SEQ ID NO. 2 and SEQ ID NO: 4, respectively. The polypeptide to be used in accordance with the present invention may have at least 60% homology/similarity/identity to the polypeptide having the amino acid sequence as depicted in SEQ ID NO. 2 and SEQ ID NO: 4, respectively. More preferably, the polypeptide has at least 65%, 70%, 75%, 80%, 85%, 90%, 91%, 92%, 93%, 94%, 95%, 96%, 97% or 98% similarity/identity to the polypeptide having the amino acid sequence as depicted in SEQ ID NO. 2 and SEQ ID NO: 4, wherein the higher values are preferred. Most preferably, the polypeptide has at least 99% similarity/identity to the polypeptide having the amino acid sequence as depicted in SEQ ID NO. 2 and SEQ ID NO: 4, respectively.

The C4d polypeptide (as shown, for example, in SEQ ID NO: 2 or SEQ ID NO: 4) may have one or more (e.g. up to 280 amino acids, preferably up to 100 amino acids) amino acids deleted, inserted, added and/or substituted provided that the C4d polypeptide maintains essentially the biological activity (e.g. the capacity to bind ILT4 and/or the capacity to induce/trigger/stimulate an anti-inflammatory response (or likewise the capacity to bind ILT4 and/or the capacity to down-regulate a pro-inflammatory response)) which is characteristic of the C4d polypeptides to be used in context of the present invention. The C4d polypeptide (as shown, for example, in SEQ ID NO: 2 or SEQ ID NO: 4) to be used in accordance with the present invention may, for example, have up to 280, 270, 260, 250, 240, 230, 220, 210, 200, 190, 180, 170, 160, 150, 140, 130, 120 or 110 amino acids deleted, inserted, added and/or substituted provided that the C4d polypeptide maintains essentially the biological activity (e.g. the capacity to bind ILT4 and/or the capacity to induce/trigger/stimulate an anti-inflammatory response (or likewise the capacity to bind ILT4 and/or the capacity to down-regulate a pro-inflammatory response)) which is characteristic of the C4d polypeptides to be used in context of the present invention. Preferably, the C4d polypeptide (as shown, for example, in SEQ ID NO: 2 or SEQ ID NO: 4) to be used in accordance with the present invention may, for example, have up to 100, 90, 80, 70, 60, 50, 40, 30, 20 or up to 10 amino acids deleted, inserted, added and/or substituted provided that the C4d polypeptide maintains essentially the biological activity (e.g. the capacity to bind ILT4 and/or the capacity to induce/trigger/stimulate an anti-inflammatory response (or likewise the capacity to bind ILT4 and/or the capacity to down-regulate a pro-inflammatory response)) which is characteristic of the C4d polypeptides to be used in context of the present invention. An exemplary C4d polypeptide to be used in accordance with the present invention may, for example, have 39 amino acids deleted at the N-terminus of SEQ ID NO: 2 and/or have 15 amino acids deleted at the C-terminus of SEQ ID NO: 2.

Preferably, any such deletions, insertions, additions and/or substitutions (in this context particularly substitutions) are conservative, i.e. amino acids are substituted by amino acids having the same or similar characteristics. For example, a hydrophobic amino acid will preferably be substituted by another hydrophobic amino acid and so on.

Further, amino acids may be added to the herein above described C4d polypeptides. For example, at least 1, 2, 3, 4, 5, 10, 20, 30, 40, 50, 60, 70, 80, 90, 100, 120, 140, 160, 180, 200, 220, 240, 260 and up to 280 amino acids (or even more amino acids) may be added to the N-terminus of the polypeptides In addition, or in the alternative, at least 1, 2, 3, 4, 5, 10, 20, 30, 40, 50, 60, 70, 80, 90, 100 and up to 110 amino acids (or even more amino acids) may be added to the C-terminus of the polypeptides without deferring from the gist of the present invention.

One exemplary C4d peptide to be used herein may comprise or consist of the amino acid sequence shown in SEQ ID NO.6 or it may comprise or consist of the amino acid sequence shown in SEQ ID NO: 8. The C4d peptide may comprise or consist of fragments of these exemplary amino acid sequences, provided C4d polypeptide maintains essentially the biological activity (e.g. the capacity to bind ILT4 and/or the capacity to induce/trigger/stimulate an anti-inflammatory response (or likewise the capacity to bind ILT4 and/or the capacity to down-regulate a pro-inflammatory response)) which is characteristic of the C4d polypeptides to be used in context of the present invention. The exemplary C4d peptide may also comprise or consist of an amino acid sequence encoded by a nucleic acid molecule having the nucleic acid sequence as depicted in SEQ ID NO: 5 or SEQ ID NO. 7.

Accordingly, the exemplary C4d peptide may a C4d polypeptide selected from the group consisting of (a) a polypeptide comprising or consisting of an amino acid sequence encoded by a nucleic acid molecule having the nucleic acid sequence as depicted in SEQ ID NO: 5 or SEQ ID NO: 7;
(b) a polypeptide having or consisting of an amino acid sequence as depicted in SEQ ID NO:6 or SEQ ID NO: 8;
(c) a polypeptide as defined in (a) or (b) wherein one or more amino acids are deleted, inserted, added or substituted, and whereby said polypeptide has C4d biological activity;
(d) a polypeptide encoded by a nucleic acid molecule encoding a peptide having or consisting of an amino acid sequence as depicted in SEQ ID NO:6 or SEQ ID NO: 8;
(e) a polypeptide comprising or consisting of an amino acid sequence encoded by a nucleic acid molecule hybridizing under stringent conditions to the complementary strand of nucleic acid molecules as defined in (a) or (d) and whereby said polypeptide has C4d biological activity;
(f) a polypeptide having at least 60% similarity to the polypeptide of any one of (a) to (e), and whereby said polypeptide has C4d biological activity; and
(g) a polypeptide comprising or consisting of an amino acid sequence encoded by a nucleic acid molecule being degenerate as a result of the genetic code to the nucleotide sequence of a nucleic acid molecule as defined in (a), (d) and (e).

As explained above, it was surprisingly found herein that C4d can be used in the treatment of inflammatory conditions. As explained herein above "inflammatory conditions" are pathological conditions which are associated with increased levels of inflammatory markers/marker proteins like TNFα, IL-6 and the like. Accordingly, the present invention relates to a method for treating an inflammatory condition comprising the administration of an effective amount of complement split product C4d to a subject in need of such a treatment. The present invention also relates to the use of C4d for the preparation of a pharmaceutical composition for the treatment of an inflammatory condition. Further, the present invention relates to a method for suppressing or ameliorating an excessive immune response in a subject comprising the administration of an effective amount of complement split product C4d. Also a method for preventing, reducing or delaying graft rejection in a subject comprising the administration of an effective amount of complement split product C4d is subject of the present invention. Preferably, the subject is a human. The definitions and explanations in respect of "C4d" and "inflammatory conditions" and the like given herein above, apply, mutatis mutandis, in this context.

Exemplary inflammatory conditions to be treated in accordance with the present invention are inflammatory diseases or inflammatory disorders. For example, the following inflammatory conditions may be treated: graft rejection, graft versus host disease, an autoimmune disease, or atopy. Preferably, the inflammatory conditions is graft rejection or graft versus host disease.

Autoimmune diseases to be treated with the herein provided and defined C4d may be autoimmune dermatose, collagen disease, dermatomyositis, rheumatoid arthritis, alopecia areata, ankylosing spondylitis, antiphospholipid syndrome, autoimmune Addison's disease, autoimmune haemolytic anemia, autoimmune hepatitis, autoimmune inner ear disease, autoimmune lymphoproliferative syndrome (ALPS), autoimmune thrombocytopenic purpura (ATP), Behcet's disease, bullous immune disease, bullous pemphigoid, cardiomyopathy, celiac disease, chronic fatigue syndrome, chronic inflammatory demyelinating polyneuropathy, cicatricial pemphigoid, cold agglutinin disease, Crest syndrome, Crohn's disease, Dego's disease, discoid lupus, (systemic) lupus erythematosus, erosive arthritis, essential mixed cryoglobulinemia, fibromyalgia, fibromyositis, grave's disease, guallain-barre, hashimoto's thyroiditis, idiopathic pulmonary fibrosis, idiopathic thrombocytopenia purpura (ITP), IgA nephropathy, insuline dependent diabetes (Type I), juvenile arthritis, Menier's disease, mixed connective tissue disease, multiple sclerosis, myastenia gravis, pemphigus vulgaris, pernicious anemia, polychondritis, polyglandular syndromes, polymyalgia rheumatica, polymyositis, primary biliary cirrhosis, psoriasis, Raynaud's phenomenon, Reiter's syndrome, rheumatic fever, sarcoidosis, scleroderma, Sjogren's syndrome, stiff-man syndrome, ulcerative colitis, vasculitis, or vitiligo.

Preferably, rheumatoid arthritis or lupus erythematosus (particularly preferably systemic lupus erythematosus) is to be treated in accordance with the present invention.

The vasculitis may be polyarteritis nodosa, Takayasu arteritis, temporal arteritis/gian cell arteritis, uveitis, or Wegener's granulomatosis. The atopy may be cutaneous, mucosal or ungualor cutaneous atopy, such as eczema, respiratory atopy or gingival hypertrophy. The dermatomyositis may be dermatomyositis juvenile.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a subject and includes: (a) preventing a disease occurring in a subject which may be predisposed to the disease; (b) inhibiting the disease, i.e. arresting its development; or (c) relieving the disease, i.e. causing regression of the disease.

A "patient" or "subject" for the purposes of the present invention includes both humans and other animals, particularly mammals, and other organisms. Thus, the methods are applicable to both human therapy and veterinary applications. Preferably, the patient is a mammal, and most preferably the patient is a human.

In the following, pharmaceutical compositions comprising C4d as defined herein (e.g. C4d polypeptide(s) (or a functional fragment or derivative thereof)/C4d multimers comprising one or more C4d polypeptides (or a functional fragment or derivative thereof)) to be prepared and used in accordance with the present invention are described.

The pharmaceutical composition will be formulated and dosed in a fashion consistent with good medical practice, taking into account the clinical condition of the individual subject/patient, the site of delivery of the pharmaceutical composition, the method of administration, the scheduling of administration, and other factors known to practitioners. The "effective amount" of the pharmaceutical composition for purposes herein is thus determined by such considerations. The term "effective amount" as used herein refers in particular to a tolerable dose of C4d/C4d multimer as defined herein which is high enough to cause, for example, the downregulation of a pro-inflammatory response without or essentially without major toxic effects. Such effective and non-toxic doses may be determined e.g. by dose escalation studies described in the art and should be below the dose inducing severe adverse side events (dose limiting toxicity, DLT).

The skilled person knows that the effective amount of pharmaceutical composition administered to an individual will, inter alia, depend on the nature of the compound. For example, if said compound is a (poly)peptide or protein the total pharmaceutically effective amount of pharmaceutical composition administered parenterally per dose will be in the range of about 1 µg protein/kg/day to 10 mg protein/kg/day of patient body weight, although, as noted above, this will be subject to therapeutic discretion. More preferably, this dose is at least 0.01 mg protein/kg/day, and most preferably for humans between about 0.01 and 1 mg protein/kg/day. If given continuously, the pharmaceutical composition is typically administered at a dose rate of about 1 µg/kg/hour to about 50 µg/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect. The particular amounts may be determined by conventional tests which are well known to the person skilled in the art.

Pharmaceutical compositions of the invention may be administered parenterally (e.g in form of an injection solution). Also oral, rectal, intracisternal, intravaginal, intraperitoneal, topical (as by powders, ointments, drops or transdermal patch), bucal, intravitreal (e.g. injected into the vitreous body), intracameral (e.g. injected into the anterior chamber) administration or administration as an oral or nasal spray is envisaged.

Pharmaceutical compositions of the invention preferably comprise a pharmaceutically acceptable carrier. By "pharmaceutically acceptable carrier" is meant a non-toxic solid, semisolid or liquid filler, diluent, encapsulating material or formulation auxiliary of any type.

The term "parenteral" as used herein refers to modes of administration which include intravenous, intramuscular, intraperitoneal, intrasternal, subcutaneous and intraarticular injection and infusion. Preferably, the pharmaceutical compositions provided herein are to be administered intravenously, subcutaneously or intramuscularly. Preferably, the complement split product C4d (like the complement split product C4d multimer as defined herein) is to be administered intravenously, subcutaneously or intramuscularly.

The methods of treating an inflammatory condition, suppressing or ameliorating an excessive immune response, or preventing, reducing or delaying graft rejection, provided herein can comprise intravenous subcutaneous or intramuscular administration of an effective amount of complement split product C4d (like a multimer thereof) as defined herein.

The pharmaceutical composition is also suitably administered by sustained release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547-556 (1983)), poly (2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133,988). Sustained release pharmaceutical composition also include liposomally entrapped compound. Liposomes containing the pharmaceutical composition are prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545;

and EP 102,324. Ordinarily, the liposomes are of the small (about 200-800 Angstroms) unilamellar type in which the lipid content is greater than about 30 mol. percent cholesterol, the selected proportion being adjusted for the optimal therapy.

For parenteral administration, the pharmaceutical composition is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

Generally, the formulations are prepared by contacting the components of the pharmaceutical composition uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non aqueous vehicles such as fixed oils and ethyl oleate are also useful herein, as well as liposomes. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The components of the pharmaceutical composition to be used for therapeutic administration must be sterile. Sterility is readily accomplished by filtration through sterile filtration membranes (e.g., 0.2 micron membranes). Therapeutic components of the pharmaceutical composition generally are placed into a container having a sterile access port, for example, an intravenous solution bag or vial having a stopper pierceable by a hypodermic injection needle. The components of the pharmaceutical composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic Water-for-Injection.

C4d polypeptide(s) (or a functional fragment or derivative thereof)/C4d multimers comprising one or more C4d polypeptides (or a functional fragment or derivative thereof) to be used in accordance with the present invention may be prepared by standard (biotechnological) methods which are well known in the art and have been described in detail herein above.

C4d as defined above (e.g C4d polypeptide(s) (or a functional fragment or derivative thereof)/C4d multimers comprising one or more C4d polypeptides (or a functional fragment or derivative thereof) may also be used in gene therapy. For example, nucleic acids comprising sequences encoding C4d as defined may be administered to treat an inflammatory condition. Gene therapy refers to therapy performed by the administration to a subject of an expressed or expressible nucleic acid. In this aspect of the invention, the nucleic acids produce their encoded protein that mediates a therapeutic effect.

Any of the methods for gene therapy available in the art can be used according to the present invention. Exemplary methods are described below. For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 1 1(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In this aspect, a composition of the invention comprises nucleic acids encoding C4d/C4d multimer(s) as defined herein, said nucleic acids being part of an expression vector that expresses a gene encoding C4d in a suitable host. Such nucleic acids have promoters, e.g. heterologous promoters, operably linked to the coding region, said promoter being inducible or constitutive, and, optionally, tissue-specific. Nucleic acid molecules may be used in which the C4d coding sequences and, optionally, any other desired sequences are flanked by regions that promote homologous recombination at a desired site in the genome, thus providing for intrachromosomal expression of the C4d encoding nucleic acids (Koller and Smithies, Proc. Natl. Acad. Sci. USA 86:8932-8935 (1989); Zijlstra et al., Nature 342:435-438 (1989). Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

The nucleic acid sequences may be directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc.

Alternatively, nucleic acid-ligand complexes can be formed in which the ligand comprises a fusogenic viral peptide to disrupt endosomes, allowing the nucleic acid to avoid lysosomal degradation. In a further alternative, the nucleic acid can be targeted in vivo for cell specific uptake and expression, by targeting a specific receptor (see, e.g., PCT Publications WO 92/06 180; WO 92/22715; WO92/203 16; WO93/14188, WO 93/20221). Alternatively, the nucleic acid can be introduced intracellularly and incorporated within host cell DNA for expression by homologous recombination (Koller and Smithies, Proc. Natl. Acad. Sci. USA 86:8932-8935 (1989); Zijlstra et al., Nature 342:435-438 (1989)).

Also viral vectors that contain nucleic acid sequences encoding C4d/C4d multimers may be used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding C4d to be used in gene therapy are cloned into one or more vectors, which facilitates delivery of the gene into a patient. More detail about retroviral vectors can be found in Boesen et al., Biotherapy 6:29 1-302 (1994), which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Klein et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995).

Adeno-associated virus (AAV) has also been proposed for use in gene therapy (Walsh et al., Proc. Soc. Exp. Biol. Med. 204:289-300 (1993); U.S. Pat. No. 5,436,146). Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this aspect of the invention, the nucleic acid may be introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcellmediated gene transfer, spheroplast fusion, etc. Numerous techniques are known in the art for the introduction of foreign genes into cells (see, e.g., Loeffler and Behr, Meth. Enzymol. 217:599-718 (1993); Cohen et al., Meth. Enzymol. 217:718-644 (1993); Clin. Pharma. Ther. 29:69-92m (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny. The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc. Preferably, the cell used for gene therapy is autologous to the patient.

If recombinant cells are used in gene therapy, nucleic acid sequences encoding C4d/C4d multimers are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g., PCT Publication WO 94/08598; Stemple and Anderson, Cell 7 1:973-985 (1992); Rheinwald, Meth. Cell Bio. 21A:229 (1980); and Pittelkow and Scott, Mayo Clinic Proc. 71:771 (1986)). The nucleic acid to be introduced for purposes of gene therapy may comprise an inducible promoter operably linked to the coding region, such that expression of the nucleic acid is controllable by controlling the presence or absence of the appropriate inducer of transcription.

As mentioned above, in context of the present invention the first receptor, to which C4d specifically binds, has been identified to be ILT4. Accordingly, the present invention relates to a protein complex comprising a first protein interacting with a second protein, wherein (i) the first protein is complement split product C4d, wherein said C4d is a C4d polypeptide selected from the group consisting of (a) a polypeptide comprising or consisting of an amino acid sequence encoded by a nucleic acid molecule having the nucleic acid sequence as depicted in SEQ ID NO: 1 (isoform C4d-A(C4Ad)) or SEQ ID NO: 3 (isoform C4d-B(C4Bd));

(b) a polypeptide having or consisting of an amino acid sequence as depicted in SEQ ID NO:2 (isoform C4d-A (C4Ad)) or SEQ ID NO: 4 (isoform C4d-B(C4Bd));

(c) a polypeptide as defined in (a) or (b) wherein one or more amino acids are deleted, inserted, added or substituted, and whereby said polypeptide has C4d biological activity;

(d) a polypeptide encoded by a nucleic acid molecule encoding a peptide having or consisting of an amino acid sequence as depicted in SEQ ID NO:2 (isoform C4d-A (C4Ad)) or SEQ ID NO: 4 (isoform C4d-B(C4Bd));

(e) a polypeptide comprising or consisting of an amino acid sequence encoded by a nucleic acid molecule hybridizing under stringent conditions to the complementary strand of nucleic acid molecules as defined in (a) or (d) and whereby said polypeptide has C4d biological activity;

(f) a polypeptide having at least 60% similarity to the polypeptide of any one of (a) to (e), and whereby said polypeptide has C4d biological activity; and
(g) a polypeptide comprising or consisting of an amino acid sequence encoded by a nucleic acid molecule being degenerate as a result of the genetic code to the nucleotide sequence of a nucleic acid molecule as defined in (a), (d) and (e).
and
(ii) the second protein is ILT4, wherein said ILT4 is
a) a polypeptide comprising an amino acid sequence encoded by a nucleic acid molecule having the nucleic acid sequence as depicted in SEQ ID NO: 9;
(b) a polypeptide having an amino acid sequence as depicted in SEQ ID NO:10;
(c) a polypeptide as defined in (a) or (b) wherein one or more amino acids are deleted, inserted, added or substituted, wherein said polypeptide is capable of interacting with C4d;
(d) a polypeptide encoded by a nucleic acid molecule encoding a peptide having an amino acid sequence as depicted in SEQ ID NO:10;
(e) a polypeptide comprising an amino acid sequence encoded by a nucleic acid molecule hybridizing under stringent conditions to the complementary strand of nucleic acid molecules as defined in (a) or (d) and encoding ILT4 or a functional fragment or functional derivative thereof, wherein said polypeptide is capable of interacting with C4d;
(f) a polypeptide having at least 60% homology to the polypeptide of any one of (a) to (e), whereby said polypeptide is ILT4 or a functional fragment or functional derivative thereof, wherein said polypeptide is capable of interacting with C4d;
(g) a polypeptide comprising an amino acid sequence encoded by a nucleic acid molecule being degenerate as a result of the genetic code to the nucleotide sequence of a nucleic acid molecule as defined in (a), (d) and (e); or
(h) a fusion protein containing any of (a) to (g).

"C4d" has been described herein above in detail. In particular definitions for determining "similar" polypeptides with reference to "human C4d" (e.g. as shown in SEQ ID NO:2 (isoform C4d-A(C4Ad)) or SEQ ID NO: 4 (isoform C4d-B(C4Bd))) have been described. These definitions apply, mutatis mutandis, in this context. Furthermore, these methods can, mutatis mutandis, be used to determine "similar" polypeptides with reference to "ILT4" (e.g. human "ILT4" as, for example, shown in SEQ ID NO: 10 or encoded by a nucleic acid molecule having a sequence as depicted in SEQ ID NO: 9). All the explanations and definitions given above in context of "C4d" polypeptides apply, therefore, mutatis mutandis to "ILT4" as comprised in the above protein complex, i.e. the term "C4d" and related sequences could simply be replaced by "ILT4" and related sequences such as the amino acid sequence shown in SEQ ID NO: 10 and the nucleic acid sequence shown in SEQ ID NO: 9.

Accordingly, the present invention relates to a method for making the protein complex described herein above, comprising the steps of:
(a) providing said first protein and said second protein; and
(b) contacting said first protein with said second protein.

Further, the present invention relates to a method for selecting modulators of the protein complex, said method comprising:
(a) contacting said first protein with said second protein in the presence of one or more test compounds; and
(b) detecting an interaction between said first protein and said second protein.

The contacting step may be conducted in vitro, for example, within a host cell. Accordingly, a host cell is provided which expresses a second protein as defined herein above, and comprises a first chimeric expression cassette having a first heterologous promoter operably linked to a first nucleic acid encoding a first protein as defined above. Further, said second protein may be expressed in the host cell from a second chimeric expression cassette having a second heterologous promoter operably linked to a second nucleic acid encoding said second protein.

Further, the present invention relates to a method for selecting modulators of the protein complex, comprising:
(a) contacting a test compound with the protein complex; and
(b) detecting interaction between said first protein and said second protein.

The methods for selecting modulators may be particularly valuable in drug screening assays in order to identify potential drugs targeting the herein above described protein complex. Preferably, the modulators are capable of stabilizing the protein complex and/or enhancing the biological activity of the protein complex. Accordingly, modulators may be selected, if the detected interaction between said first protein and said second protein indicates a more stable protein complex and/or enhanced biological activity compared with a control (a control may be a sample comprising the protein complex but not a test compound). Such modulators may be useful for the treatment of inflammatory conditions as defined herein. Also transgenic animals may be used in corresponding methods; see below.

The present invention relates to the use of a (transgenic) cell or a (transgenic) non-human animal comprising C4d or a fragment or derivative thereof (e.g. a cell or animal carrying a gene encoding for C4d) for screening and/or validation of a medicament for the treatment of an anti-inflammatory condition. The term "cell" as used in this context may also comprise a plurality of cells as well as cells comprised in a tissue. The cell(s) to be used in the screening or validation method may be obtained from samples from a (transgenic) non-human animal suffering from an inflammatory condition. Accordingly, the cell may be a human cell. Again, such a cell to be used in the present screening or validation methods may be comprised in a tissue or tissue sample, like in a sample biopsy.

The used non-human animal or cell may be transgenic or non transgenic. "Transgenic" in this context may mean that a heterologous "C4d" (i.e. a "C4d" not naturally occurring in said animal or cell) as defined herein is overexpressed. Accordingly, the term "transgenic non-human animal" or "transgenic cell" as used herein refers to an non-human animal or cell, not being a human, that comprises genetic material different from the genetic material of a corresponding wild-type animal/cell. "Genetic material" in this context may be any kind of a nucleic acid molecule, or analogues thereof, for example a nucleic acid molecule, or analogues thereof as defined herein. "Different" in this context means additional or fewer genetic material with respect to the genome of the wild-type animal/cell and/or rearranged genetic material, i.e. genetic material present at a different locus of the genome with respect to the genome of the wild-type animal/cell. An overview of examples of different expression systems to be used for generating transgenic cell/animal is, for instance, contained in Methods in Enzymology 153 (1987), 385-516, in Bitter et al. (Methods in Enzymology 153 (1987), 516-544) and in Sawers et al.

(Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). The (transgenic) non-human animal or (transgenic) cell may be or may be derived from a mammal. Non-limiting examples of the (transgenic) non-human animal or derived (transgenic) cell are selected from the group consisting of a mouse, a rat, a rabbit or a guinea pig. In accordance with the above, the present invention relates to a transgenic animal (e.g. a mouse) comprising such a heterologous "C4d" as defined herein (e.g. a human C4d or a fragment/derivative thereof).

Moreover, the present invention provides an antibody specifically binding to or specifically recognizing the herein above provided protein complex or the C4d multimer(s).

The antibody may be a polyclonal antibody, a monoclonal antibody, a full antibody (immunoglobulin), a F(ab)-fragment, a F(ab)$_2$-fragment, a single-chain antibody, a chimeric antibody, a CDR-grafted antibody, a bivalent antibody-construct, a bispecific single chain antibody, a synthetic antibody or a cross-cloned antibody and the like. Polyclonal or monoclonal antibodies or other antibodies (derived therefrom) can be routinely prepared using, inter alia, standard immunization protocols; see Ed Harlow, David Lane, (December 1988), Antibodies: A Laboratory Manual, Cold Spring Harbor Laboratory; or Ed Harlow, David Lane, (December 1998), Portable Protocols (Using Antibodies): A Laboratory Manual 2$^{nd}$ edition, Cold Spring Harbor Laboratory.

For example, immunization may involve the intraperitoneal or subcutaneous administration of the protein/protein complex/multimer (and/or fragments or derivatives thereof and so on) as defined herein to a mammal (e.g. rodents such as mice, rats, hamsters and the like). A protein/polypeptide specific for the protein complex or multimer may be used. Preferably, fragments of the protein/polypeptide/multimer are used.

The present invention is additionally described by way of the following illustrative non-limiting examples that provide a better understanding of the present invention and of its many advantages.

Unless otherwise indicated, established methods of recombinant gene technology were used as described, for example, in Sambrook, Russell "Molecular Cloning, A Laboratory Manual", Cold Spring Harbor Laboratory, N.Y. (2001) which is incorporated herein by reference in its entirety.

The Figures show:

FIG. 1. Identification of ILT4 as cellular receptor for C4d. a Flow cytometric analyses showing the interaction of biotinylated recombinant human C4d (20 m/mL) of both isoforms, rh-C4Ad and rh-C4Bd, with monocytes and monocyte-derived dendritic cells (moDC; grey histograms). Open histograms represent the reactivity of the secondary reagent with these cells. SA-PE: streptavidin-R-PE. b C4d-reactive cells were enriched from a Bw cell pool expressing a cDNA library derived from human moDC by multiple rounds of FACS. Data obtained for rh-C4Bd are representative for those obtained using rh-C4Ad (data not shown). Sorting gates are shown. c Single cell clones derived from the C4d reactive Bw cell pool were probed with rh-C4Ad- and rh-C4Bd. MFI: mean fluorescence intensity. d PCR-amplification of the retroviral inserts of the C4d-b(C4Bd) binding clones 1.5 and 3.7. e Bw cells expressing a 2 kb retroviral insert encoding immunoglobulin-like transcript 4 (ILT4) were probed with biotinylated rh-C4Ad, rh-C4Bd and C4d isolated from human plasma (ih-C4d) each at 20 m/mL or ILT4-specific mMAb (grey histograms). Open histograms represent reactivity of C4d molecules and ILT4 mMAb with control Bw-cells. f Monocytes and moDC were analyzed for ILT4 expression (grey histograms, ILT4-mMAb; open histograms, isotype control).

Figure 2:
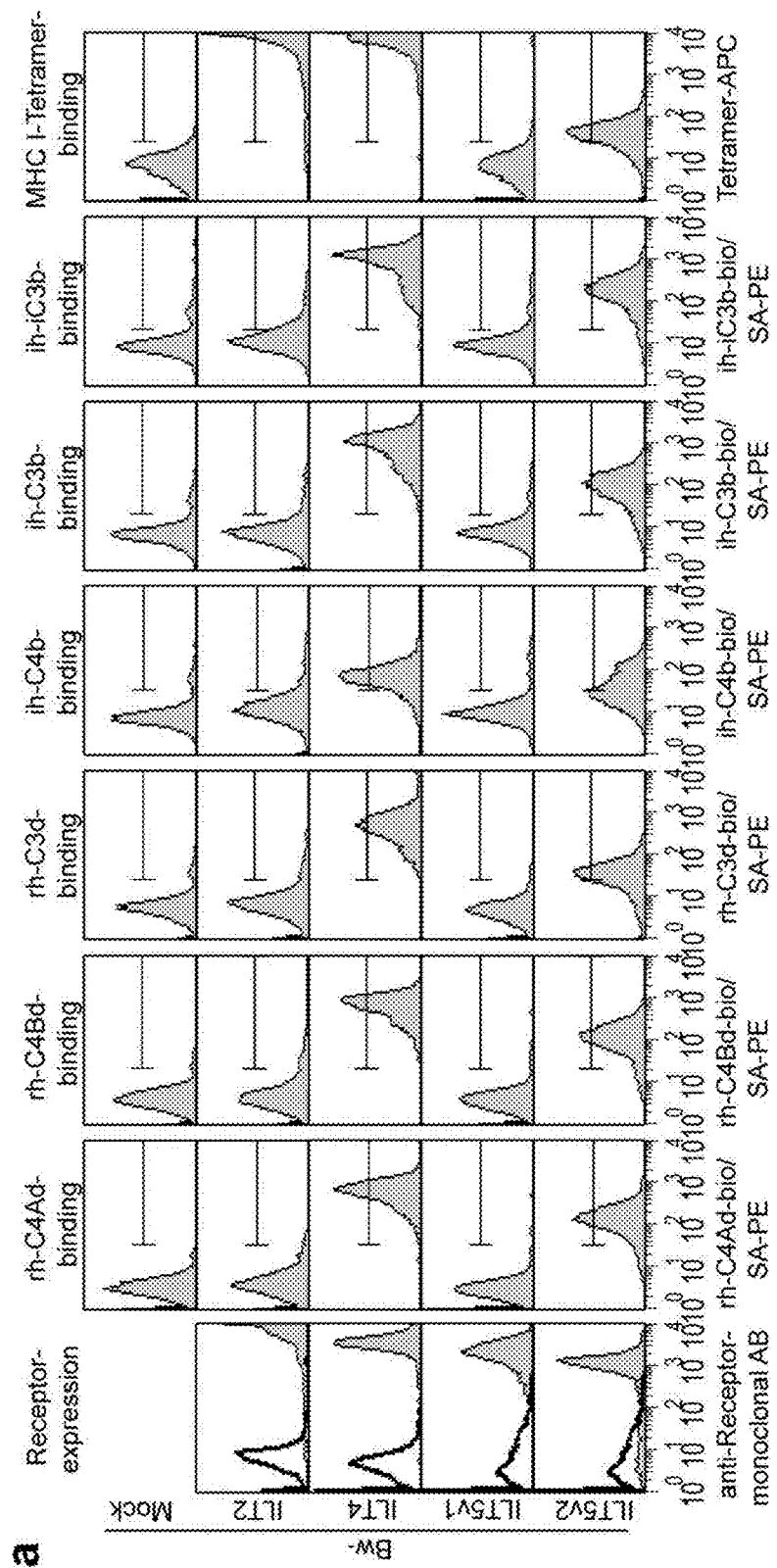
Figure 2:
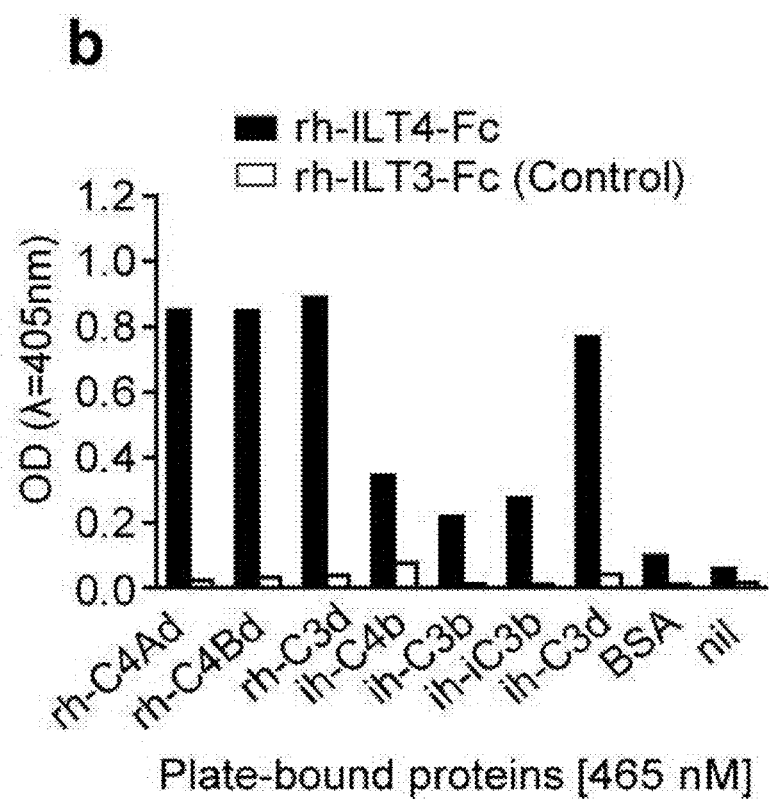
Figure 2:
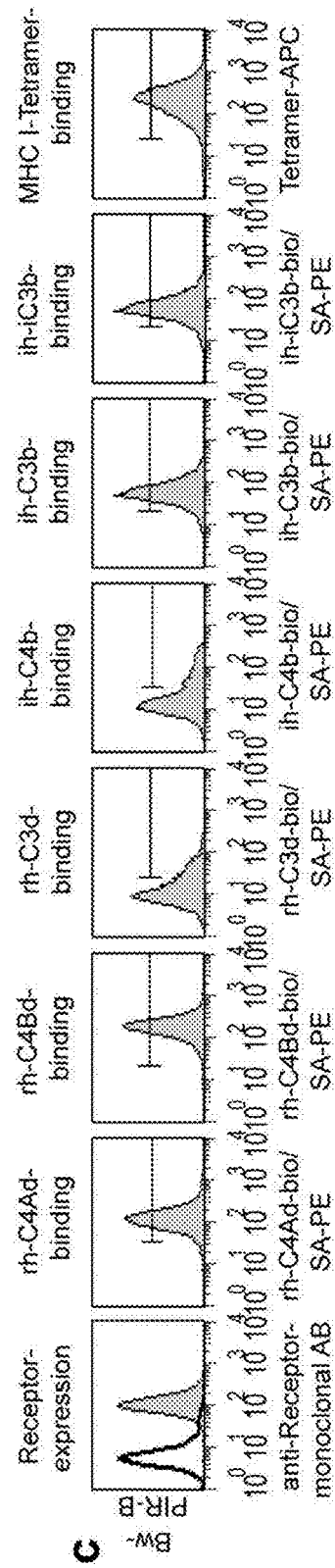

FIG. 2. Interaction of ILT4 and ILT5v2 with C4d, C4b, C3d, C3b and iC3b. a Flow cytometric analysis of Bw cells transduced to express ILT2, ILT4 and ILT5-antigenic variants 1 and 2 (ILT5v1 and ILT5v2). Expression of ILT-receptors was verified with specific monoclonal antibodies (left panels, grey histograms; open histograms represent reactivity of ILT MAbs with mock treated Bw cells). Interaction of Bw cells expressing ILT-molecules and mock-treated Bw cells with the indicated CSPs (20 μg/mL each) and with MHC-class I tetramers (further panels, grey histograms). b Interaction of plate-bound CSPs with recombinant human ILT4-Fc fusion protein (rh-ILT4-Fc) or control Fc-fusion protein (rh-ILT3-Fc) was analyzed in an ELISA. c Bw cells transduced to express PIR-B, the murine ortholog of ILT4, were probed with a PIR-B-specific monoclonal antibody or with human CSPs and human MHC-class I tetramers.

FIG. 3. Classical receptor-ligand interaction between C4d and ILT4. a Bw-ILT4 cells or control Bw cells (Bw-mock) were incubated with different concentrations of C4Ad and cell-bound C4Ad was measured by flow cytometry using C4d-mMAb for detection. Data obtained for C4Ad are representative for those using C4Bd, data not shown. Mean and standard deviation of triplicate measurements are shown. b Dissociation constant (Kd) of the C4d-ILT4 interaction assessed via Langmuir binding isotherm equation for single class 1:1 binding equilibrium based on data shown in FIG. 3a. Data sets of triplicate measurements exhibited strong correlation ($R^2$=0.99). c Binding of biotinylated C4Ad or C4Bd (20 ug/ml) to Bw control cells or to Bw-ILT4 in absence or presence of unlabelled C4Ad. d Binding of biotinylated C4Ad or C4Bd (20 ug/ml) to Bw control cells or to Bw-ILT4 in presence or absence of ILT4-specific antibodies.

FIG. 4. Attenuation of intracellular $Ca^{2+}$-flux and reduction of pro-inflammatory cytokine secretion by linked, functionally multimerised, complement split products. a $Ca^{2+}$-flux elicited in monocytes via FcγR-crosslink with or without simultaneous triggering of ILT4 through crosslink of receptor-bound CSPs or ILT4-mMAb (each at 10 μg/ml) as assessed via flow cytometry. $Ca^{2+}$-flux induced by triggering of FcγR-crosslink alone (red lines, positive control) as compared to $Ca^{2+}$-flux modified by co-crosslink of ILT4 through the respective ILT4-ligands (blue lines). Data shown are representative for at least three independent experiments. b Cytokine production of monocytes stimulated by FcγR-crosslink through solid phase bound human IgG with or without simultaneous triggering of ILT4 via distinct amounts of C4d isolated from serum of a healthy human adult.

c Cytokine production of monocytes stimulated by solid phase bound human IgG in absence or presence of distinct amounts of immobilized ILT4 mMAb. b and c: mean percentage of cytokine production of 5 independent experiments is shown, *p<0.05, p<0.01, *p<0.005; error bars indicate the SEM.

Figure 5:
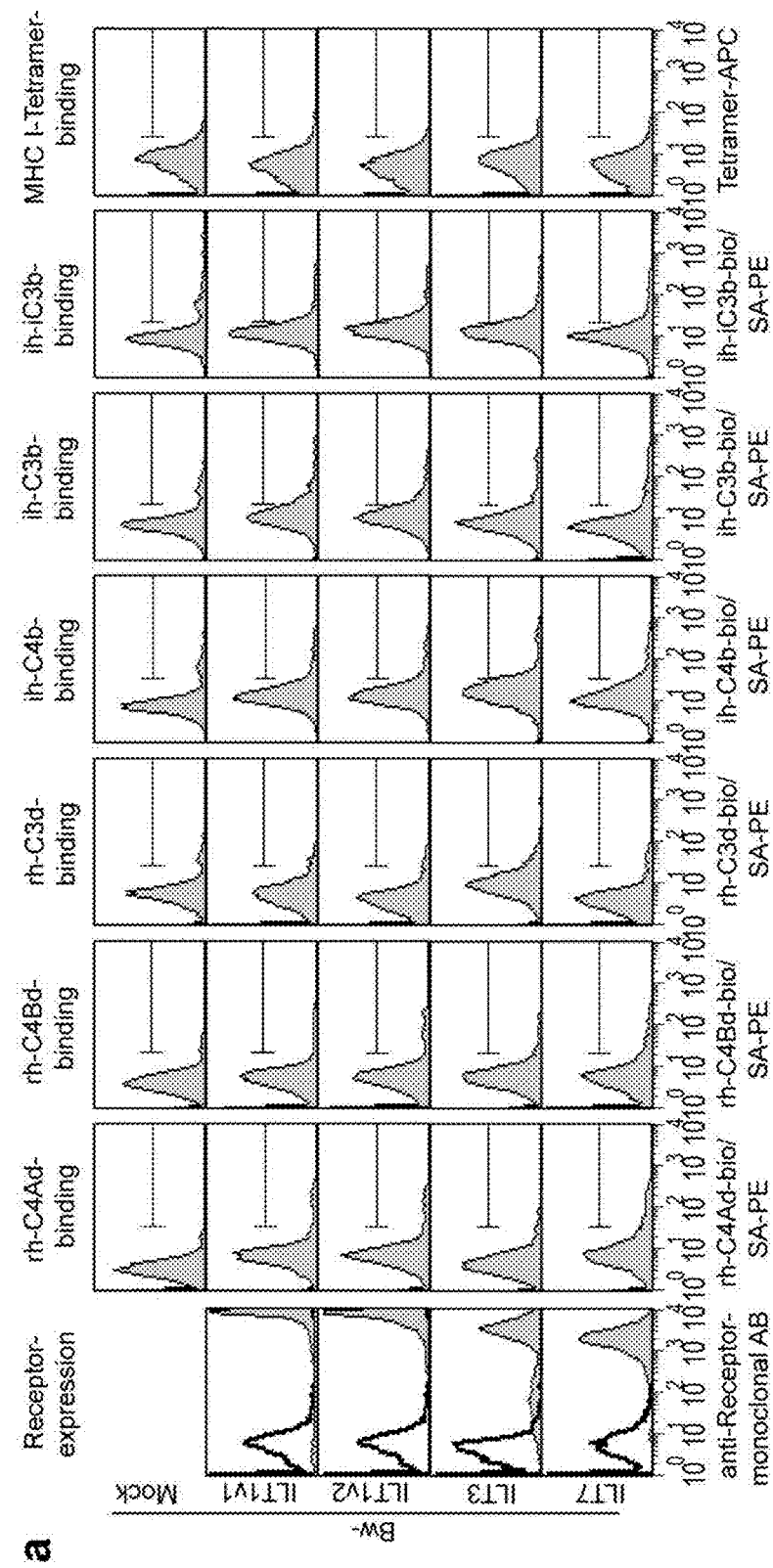
Figure 5:
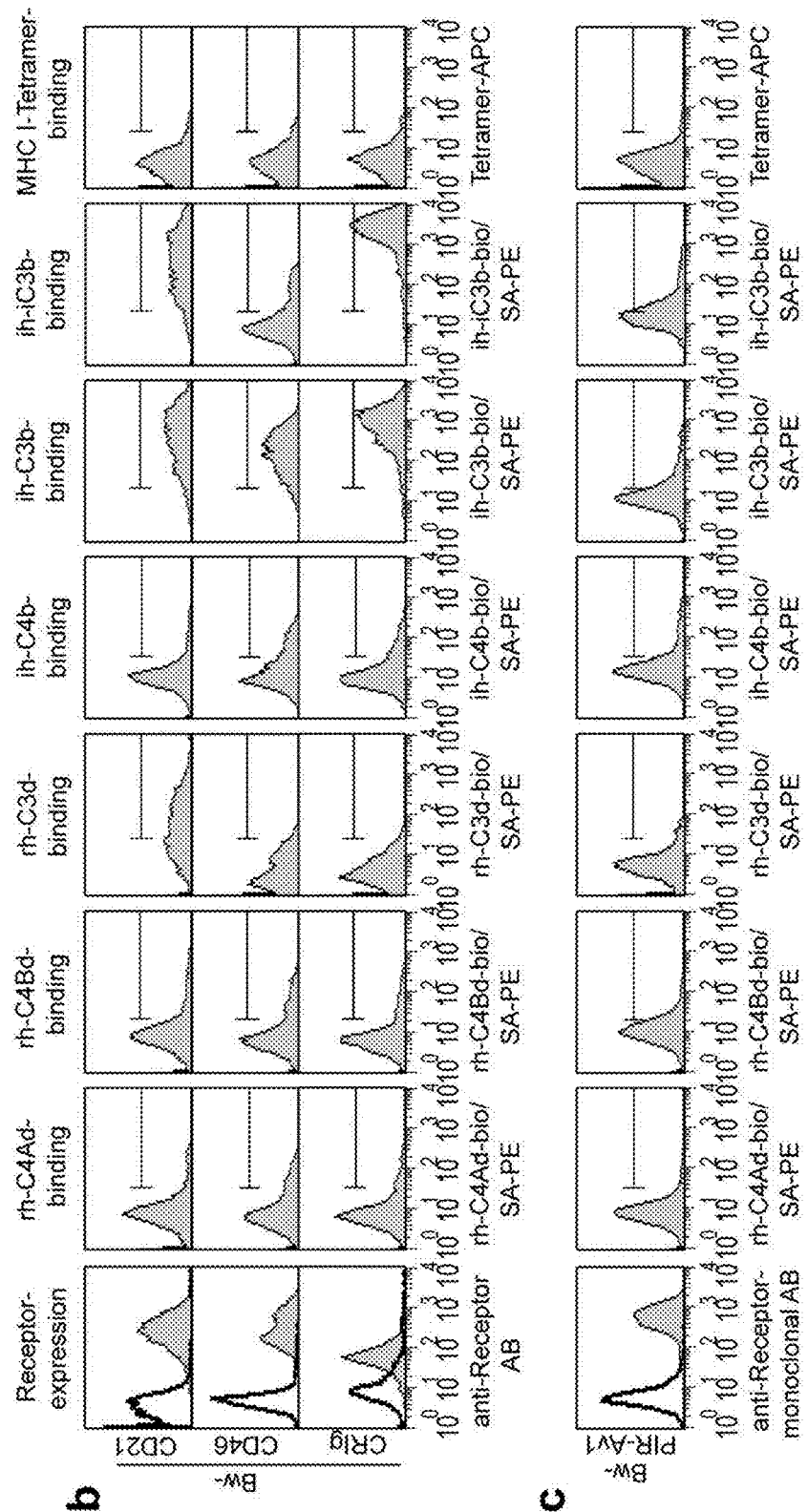
Figure 5:
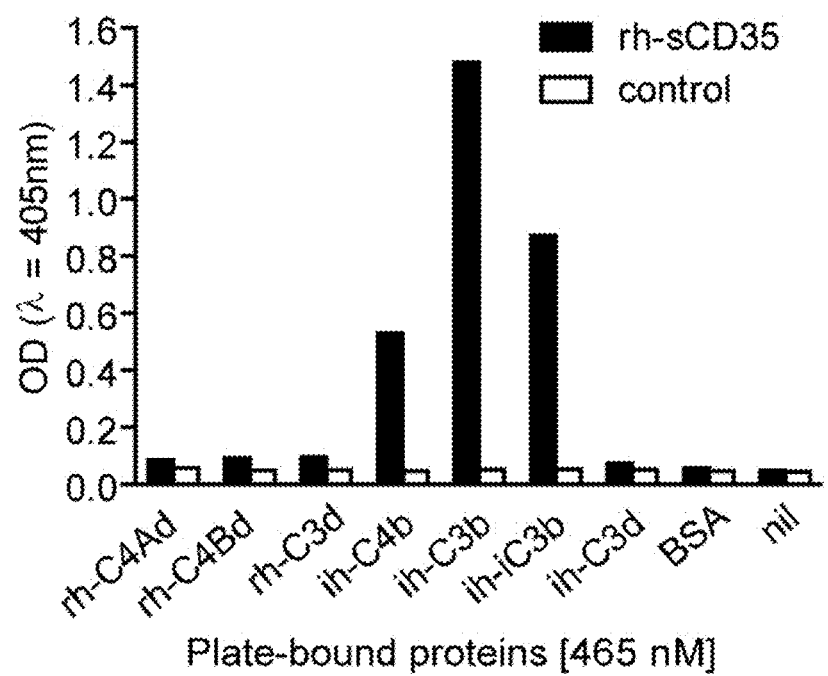

FIG. 5. Flow cytometric analysis of the interaction of C4d, C3d, C4b, C3b and iC3b and human MHC class I tetramers with Bw cells transduced to express a ILT1 transcript variants 1 and 2 (ILT1v1 and ILT1v2), ILT3 and ILT7, b previously established complement receptors CD21, CD46 and CRIg, and c PIR-A transcript variant 1 (PIR-Av1), murine ortholog of ILT1. a-c left panels: Expression of transduced receptors was assessed using specific antibodies (grey histograms); open histograms represent reactivity of these antibodies with control Bw cells. d Plate-bound CSP were probed with a recombinant protein representing the human CD35 extracellular domain (rh-sCD35) via ELISA. BSA was used as a plate-bound ligand control; white control bars represent no rh-sCD35 added to the assay.

The Example illustrates the invention.

EXAMPLE 1

C4d in the Treatment of Disorders Associated with Immune-Mediated Inflammation

Methods

Biotinylation of Human Complement Split Products.

Recombinant human C4d of both isoforms (rh-C4Ad and rh-C4Bd), rh-C3d, ih-C4b, ih-C3b and ih-iC3b were tagged via biotinylation of amino groups using Biotin-X-NHS (Calbiochem, San Diego, Calif.) according the manufacturers protocol. When indicated, rh-C4Ad or rh-C4Bd were biotin-tagged using Iodoacetyl-LC-biotin (Pierce, Rockford, Ill.) specifically targeting the thioester cystein (C1010, pre-pro numbering), thereby resulting in a rh-C4d:biotin ratio of 1:1, according to the following procedure. After dialyzing rh-C4Ad or rh-C4Bd against NaCl/Tris-HCl (0.2M, pH 8.0), DTT (Sigma-Aldrich, Deisenhofen, Germany) was added to a final concentration of 0.1 mM. The mixture was incubated for 30 minutes at 37° C. to reduce the oxidized SH-group of monomeric rh-C4d molecules, to separate disulfide-linked rh-C4d-dimers and to inhibit dimerisation as described elsewhere[48]. Subsequently, Iodoacetyl-LC-biotin was added to a final concentration of 0.4 mM and then the solution was incubated at room temperature for 30 minutes under gentle magnetic stirring. Then, the proteins were dialyzed against PBS+0.05% $NaN_3$ at 4° C. and stored at −80° C.

Purification and Thioester-Specific Biotinylation of ih-C4d.

The generation of C4d from human plasma specifically biotinylated at the site of its internal thioester, termed isolated human C4d (ih-C4d), was performed as follows with all steps being carried out on ice or in the cold lab unless stated otherwise. Freshly donated, citrated human plasma was brought to 0.25 mg/ml PMFS (Roth, Karlsruhe, Germany). The ionic strength was adjusted to the level of the incubation buffer (20 mM sodium phosphate buffer containing 0.02% sodium azide, and 160 mM sodium chloride, pH 7.0). After incubation on a Q-Sepharose column (GE Healthcare, Uppsala, Sweden) for 90 minutes and washing, C4 was eluted by a sodium chloride gradient based on the incubation buffer with 300 mM as the final concentration. C4 containing fractions were pooled and concentrated using "Centricon" centrifugal filters with 100 kDa cut-off Millipore (Bedford, Mass.). Then C4 was biotinylated via a thioester-specific nucleophilic attack through incubation with 3.7 mM Biotin-PEO2-Amine reagent (Pierce, Rockford, Ill.) at 37° C. for 4 h. Then, C4d was generated by adding 33 µg of Factor I and 20 µg of C4-binding protein to 1 ml of Biotin-labeled C4 (2 mg/ml). Following a 2 h incubation step at 37° C., biotinylated C4d was isolated by sodium chloride gradient-elution using Q-Sepharose. C4d containing fractions were concentrated using centrifugal filters (Millipore). Purity and biotinylation-state of the ih-C4d proteins were assessed by SDS-PAGE.

Identification of Retroviral Inserts in C4d Reactive Cells.

Genomic DNA was prepared from C4d reactive single cell clones using Gentra Puregene Cell Kit (Qiagen, Hilden, Germany) according to the manufacturer's instructions followed by the PCR amplification of the integrated retroviral cDNA inserts as described[16]. The resulting PCR products were gel-purified, cloned into the retroviral expression plasmid pCJK2 and expressed in Bw cells applying a published protocol[50]. Sequence analyses of plasmid DNA from selected clones were performed via commercial DNA sequencing (MWG Biotech AG, Ebersberg, Germany).

CSP-ELISA.

Ninety-six-well ELISA plates (Corning Inc., Corning, N.Y.) were coated over night at 4° C. applying unlabelled CSPs at a concentration of 465 nM. The following day, the plates were washed six times using PBS supplemented with 0.05% Tween20 (Biorad, Hercules, Calif.). Then, wells were blocked for two hours at 20° C. applying PBS+2% HSA. Subsequently, the blocking buffer was removed and rh-ILT4-Fc or rh-ILT3-Fc fusion proteins (each at 3 µg/ml) or sCD35 (5 µg/ml) diluted in blocking buffer were added. All subsequent incubation steps were carried out at 20° C. using blocking buffer as dilution medium. After two hours of incubation, the wells were washed as described above and AP-labelled anti-human IgG-Fcγ-specific antibodies or anti-CD35 mMAb were added to the fusion proteins or the sCD35 and incubated for one hour. After washing, the anti-CD35 mMAb was incubated with HRP-labelled mouse-IgG-Fcγ-specific antibodies for one hour. The AP-signal was assessed by determining the OD at $\lambda=405$ nm using a microplate reader (Thermomax, Molecular Devices, Sunnyvale, Calif.) after the addition of p-Nitrophenyl phosphate disodium hexahydrate (pNPP; Sigma-Aldrich) diluted in diethanolamine at 1 mg/ml. The HRP-signal was measured at $\lambda=405$ nm after incubation with ABTS solution (Roche Applied Sciences, Penzberg, Germany).

$Ca^{2+}$-Flux Measurement.

Labelling of monocytes using Indol-AM (Sigma-Aldrich) at 404 was performed in X-VIVO-10 supplemented with 100 U/ml penicillin and 100 m/mL streptomycin at 37° C. for 45 minutes. Subsequently, the cells were washed in ice-cold FACS buffer and all subsequent steps were carried out at 4° C. The cells were resuspended in ice-cold FACS buffer, aliquoted to cell culture tubes and co-incubated for 30 minutes with monomeric human IgG and distinct CSPs or ILT4 mMAb. Then, the monocytes were washed twice, resuspended and co-incubated for 20 minutes with biotinylated goat IgG-Fab fragments specific for human IgG and either biotinylated CSP-specific mMAbs or biotinylated goat IgG-F(ab')₂ anti-mouse IgG. After two final washing steps the cells were resuspended and $Ca^{2+}$-flux was measured on a LSR II flow cytometer from Becton-Dickinson after bringing the cells to 37° C. in a water bath. After measuring the baseline $Ca^{2+}$-flux cells were incubated with soluble SA (Sigma-Aldrich) resulting in co-crosslink of biotinylated molecules attached to the cell surface. $Ca^{2+}$-flux as expressed by the Indo blue/Indo violet ratio was evaluated applying FlowJo software (TreeStar Inc., Ashland, Oreg.).

Ex-Vivo Model of Antibody-Mediated Rejection.

Ninety-six-well flat bottom cell culture plates (Corning Inc., Corning, N.Y.) were coated over night at 4° C. either with or without human IgG (Beriglobin P) at 100 m/mL in the presence or absence of 5 µg/mL SA (Sigma-Aldrich) or goat anti-mouse F(ab')₂ fragments. Coating volume was 100 µL per well. The following day, wells were washed five times using 200 µL DPBS (PAA, Pasching, Austria) per well. Subsequently, wells were blocked for two hours at 20°

C. using 200 μL/well DPBS+2% HSA. Then, the blocking buffer was removed and graded amounts of biotinylated ih-C4d or anti-ILT4 mMAb diluted in blocking buffer was added. After two hours of incubation at 20° C., the wells were washed as described above and 50,000 freshly isolated monocytes resuspended in serum-free X-VIVO-10 supplemented with 100 U/ml penicillin and 100 m/mL streptomycin were applied per well. The plates were incubated at 37° C. in the presence of 5% $CO_2$ and 100% air humidity. Production of TNF-α and IL-6 was assessed in cell free supernatants collected after 14 hours of stimulation via sandwich ELISA.

Statistics.

Statistical differences for mean absolute values of produced cytokines were assessed using the paired, two-tailed Student's t test. In order to achieve a normal distribution the log of absolute values was used in the t test. Differences were considered statistically significant for $p < 0.05$.

Ethics.

Blood-sampling from healthy individuals to generate ih-C4d was approved by the ethics committee of the Vienna General Hospital and the Medical University of Vienna. Prior to blood-sampling informed consent was obtained from blood donors.

Antibodies and Reagents.

All primary antibodies react with human molecules unless stated differently. Mouse monoclonal antibodies (mMAb) specific for ILT1 (clone 24) and ILT7 (clone 17G10.2) were obtained from BioLegend (San Diego, Calif.), mMAbs specific for ILT3 (clone 293623), ILT4 (clone 287219), ILT5 (clone 222821) and goat polyclonal ILT4 specific antibody as well as rh-ILT4-Fc fusion protein were purchased from R&D Systems (Minneapolis, Minn.). Rh-ILT3-Fc fusion protein was produced using previously described methods[51]. ILT2 specific mMAb (clone 6-228) was generated and kindly provided by Dr. Otto Majdic (Institute of Immunology, Medical University of Vienna, Austria). Rat monoclonal antibodies (rMAbs) specific for murine PIR-B (clone 326414) or murine PIR-A/B (clone 404127) were from R&D Systems. mMAbs specific for CD35 (CR1; clone J3D3), CD21 (CR2; clone B-ly4) or CD46 (MCP; clone 169-1-E4.3) were from Beckman Coulter (Fullerton, Calif.), BD Pharmingen (San Diego, Calif.) and Ancell (Bayport, Minn.), respectively. Rabbit polyclonal antibody specific for CRIg (VSIg4, Z39Ig) was obtained from Abcam (Cambridge, UK). Biotinylated and unlabelled C4d-specific mMAb were purchased from Quidel (San Diego, Calif.) while C3d specific mMAb (clone 7C10) was from Abcam. Recombinant human MHC Class I Tetramer-SA-APC (#T01054) was obtained from Beckman Coulter. Soluble recombinant human CD35 extracellular domain (sCD35) was a gift from Avant Immunotherapeutics (Needham, Mass.). Streptavidin-R-PE (SA-PE), SA-APC, R-PE-F(ab')$_2$ fragment goat anti-mouse-IgG-Fcγ, APC-F(ab)$_2$ fragment goat anti-mouse IgG-Fcγ, biotin-F(ab')$_2$ fragment goat anti-mouse-IgG(H+L), biotin-Fab fragment goat anti-human-IgG(H+L), AP-F(ab')$_2$ fragment goat anti-human IgG-Fcγ, HRP-F(ab)$_2$ fragment goat anti-mouse IgG-Fcγ and unlabeled F(ab')$_2$ fragment goat anti-mouse IgG(H+L) were from Jackson ImmunoResearch (West Grove, Pa.).

Cell Culture.

Bw cells were grown in RPMI 1640 supplemented with 10% fetal bovine serum (FBS, standard quality), 2 mM L-Glutamin and 100 U/mL Penicillin/100 μg/mL streptomycin (all from PAA, Pasching, Austria), 0.5 μg/mL amphotericin B (Sigma-Aldrich, Deisenhofen, Germany) and 2 μg/mL plasmocin (Invivogen, San Diego, Calif.). Peripheral blood mononuclear cells (PBMC) of healthy individuals were isolated from buffy coats purchased from the Austrian Red Cross via density centrifugation using Lymphoprep (Axis-Shield, Oslo, Norway). Subsequent isolation of monocytes from the PBMC-pool was performed by magnetic activated cell sorting (MACS) using reagents from Mitenyi Biotech (Bergisch Gladbach, Germany). Positively selected (CD14 microbeads) monocytes were differentiated into monocyte-derived dendritic cells (moDC) through culturing in RPMI 1640 supplemented with 10% fetal bovine serum, 2 mM L-Glutamin and 100 U/mL Penicillin/100 μg/mL streptomycin and 10 ng/mL rh-IL-4 and 50 ng/mL rh-GM-CSF, both from PeproTech (Rocky Hill, N.J.). Monocytes used for functional assays were negatively selected using Monocyte isolation Kit II and either resuspended in serum-free culture medium X-VIVO-10 from Lonza (Basel, Switzerland) supplemented with 100 U/ml penicillin and 100 μg/mL streptomycin or in FACS-buffer (DPBS with Ca & Mg (PAA, Pasching, Austria) supplemented with 0.5% human serum albumin (HSA; CSL Behring, Vienna, Austria) and immediately used in experiments.

Fluorescence Activated Cell Sorting and Flow Cytometric Analyses.

Flow cytometric analyses were performed via a FACSCalibur flow cytometrer (BD Biosciences, Franklin Lakes, N.J.) using 60,000 cells per sample resuspended in FACS-buffer. In experiments employing monocytes or moDCs, human IgG (Beriglobin P; CSL Behring, Vienna, Austria) was used at 20 mg/mL to block Fcγ receptors. For fluorescence-activated cell sorting (FACS), Bw cells expressing a retroviral cDNA expression library generated from moDC[16] were incubated with biotinylated rh-C4Ad or rh-C4Bd (20 m/mL each) in FACS-buffer for 30 minutes on ice followed by two washing steps and subsequent detection of bound biotinylated C4d molecules through incubation with SA-PE. FACS was performed using a FACSDiva (BD Biosciences).

Results

To assess a potential interaction between C4d and structures on monocytes or monocyte-derived dendritic cells (moDC), these cells were probed with recombinant human C4d of both isoforms (rh-C4Ad and rh-C4Bd). Both molecules specifically reacted with either cell-type (FIG. 1a). To identify cellular receptors mediating this interaction, a cDNA library derived from moDC (described in[16]) retrovirally expressed on the murine thymoma cell line Bw5147 (Bw cells) was screened for C4d receptors. Rh-C4Ad- and rh-C4Bd-reactive cells were enriched by multiple rounds of FACS (FIG. 1b). Single cell clones established from the reactive pools strongly bound both C4d isoforms (FIG. 1c). Re-expression of a PCR-retrieved 2 kb retroviral cDNA insert present in both clones (FIG. 1d) conferred reactivity for rh-C4Ad, rh-C4Bd as well as C4d isolated from human plasma (ih-C4d; FIG. 1e). Differences in the binding signal between recombinant C4d and ih-C4d derive from distinct biotinylation approaches (described in Methods). DNA sequence analysis of the inserts identified immunoglobulin-like transcript 4 (ILT4, also termed CD85d, LILRB2, LIR2 and MIR10) as cellular C4d-receptor. In line with earlier reports[4,17,18], it was found that ILT4 is expressed on monocytes and moDC (FIG. 1f). ILT4 has been shown to elicit a negative signal via cytoplasmic immunoreceptor tyrosine-based inhibitory motifs (ITIMs), thus, down-modulating pro-inflammatory immune responses[4,5,19]. It has been implicated in control of autoreactivity[20], maintenance of fetomaternal tolerance during pregnancy and induction of transplantation tolerance[21-25]. Receptors of the ILT family show considerable sequence similarity, and previously identified ILT4 ligands, like classical (HLA-A and -B) and non-classical (HLA-G1, -E, and -F) MHC class I molecules, also interact with ILT2[4,19,26-30]. Therefore, other ITIM containing ILTs, like ILT2, ILT3 and antigenic variants of the highly polymorphic ILT5 (ILT5v1 and ILT5v2) were expressed, and probed with C4d. Also ILTs were expressed which confer activating signals via co-localisation with immunoreceptor tyrosin-based activation motif (ITAM) bearing Fc-receptor common gamma chain like ILT1 transcript variants 1 and 2 (ILT1v1 and ILT1v2) and ILT7[31]. It was found that ILT5v2 also acted as receptor for C4d, whereas no binding was observed with ILT5v1 or any other ILT molecule tested (FIG. 2a and FIG. 5a). Importantly, it was found that in addition to C4d also rh-C3d, ih-C4b, ih-C3b and ih-iC3b acted as ligands for ILT4 and ILT5v2. By contrast, binding of these CSPs to other ILT molecules was not observed (FIG. 2a and FIG. 5a). A specific interaction between ILT4 and CSPs was confirmed through an independent ELISA approach employing solid phase-bound CSPs and soluble ILT4 represented by a rh-ILT4-Fc fusion protein (FIG. 2b). Cells engineered to express human complement receptors CD21 (CR2), CD46 (MCP) and CRIg (Z39Ig, VSIG4) interacted with their established ligands but failed to bind C4d (FIG. 5b). Moreover, CD35 (CR1) interacted with its known ligands C4b, C3b and iC3b, while failing to bind C4d or C3d (FIG. 5d). MHC class I tetramers strongly bound to ILT4 and ILT2, and to a weaker extent also to ILT5v2, while there was no interaction with other ILTs (FIG. 2a and FIG. 5a). These results demonstrate that although ILT4 and ILT5v2 share specificity for classical CSPs with established complement receptors, C4d-b(C4Bd) binding is restricted to ILT4 and ILT5v2.

Paired immunoglobulin receptor B (PIR-B) and PIR-A are the murine orthologs of ILT4 and ILT1, respectively. PIR-B deficiency in mice was shown to lead to autoimmune glomerulonephritis[32] and exacerbated graft versus host disease[33]. The herein provided binding studies revealed that PIR-B, like ILT4 served as receptor for human CSPs C4d, C3b and iC3b, whereas respective CSPs did not interact with PIR-A (FIG. 2c and FIG. 5c).

Binding affinity between C4d and ILT4 was assessed applying rh-C4d over a wide dilution range to ILT4 expressing cells using C4d-specific antibody for detection. This interaction proved to be saturable (FIG. 3a), and the dissociation (Kd) constant of the C4d-ILT4 interaction was determined to be 0.63 µM (FIG. 3b), representing a minimum estimate because of the non-equilibrium nature of the assay.

The interaction of ILT4 with rh-C4d biotinylated via the thioester cystein was inhibited by unlabelled C4d of either isoform in a dose dependent fashion (FIG. 3c) as well as by ILT4 antibodies (FIG. 3d). These data indicate a classical receptor-ligand interaction between C4d and ILT4.

Previous studies have demonstrated that ILT4 triggering inhibit FcγR-mediated intracellular $Ca^{2+}$-flux[4,19]. Herein, the capability of CSPs to modulate FcγR-mediated $Ca^{2+}$-flux in Indo-1 AM labelled monocytes was assessed, thereby mimicking the interaction of complement-loaded ICs with immune cells. Simultaneous co-crosslink of FcγR and CSPs resulted in a reduction of $Ca^{2+}$-flux as compared to FcγR crosslink alone (FIG. 4a). ILT4-specific antibodies inhibited $Ca^{2+}$-flux to a similar extent. This indicates that triggering of ILT4 by CSPs is responsible for the reduction of $Ca^{2+}$-flux observed in the experiments summarized in FIG. 4a. To explore a potential functional effect of C4d on monocytes in AMR, an ex-vivo AMR-model was developed using human IgG and graded amounts of biotinylated ih-C4d co-immobilized on cell culture plates. Production of proinflammatory cytokines by monocytes incubated in this experimental setting was assessed. In the presence of immobilized ih-C4d production of TNF-α and IL-6 upon FcγR crosslink was significantly reduced as compared to FcγR crosslink alone (FIG. 4b). Similar results were obtained when C4d was replaced by ILT4-specific antibodies, indicating that the observed reduction of cytokine secretion was mediated through C4d-ILT4 interaction (FIG. 4c).

To date, the mechanisms involved in maintaining an anti-inflammatory state and self-tolerance during the homeostatic elimination of ICs and apoptotic material have been poorly understood. However, complement is known to play a central role, since loss of self-tolerance and autoimmune syndromes are associated with complement deficiency states of the early components of the classical pathway. Complete deficiencies of C4 and C1q result in the most severe forms of SLE-like disease, while patients with defects in C2 or C3 typically present with milder symptoms[34,35]. Copy number variations or polymorphisms of the C4 gene are also associated with SLE-like disease, with low copy numbers being a risk factor while high copy numbers confer protection[36]. In addition, the spontaneous development of SLE-like autoimmunity in C4 deficient mice can occur independent of CD35/CD21[37]. Thus, the herein provided data indicate that additionally to defective clearance of ICs and apoptotic material[34,38-42] a compromised maintenance of non-reactivity towards the "self"/"non dangerous" through failure of adequate ILT4-triggering on phagocytes might significantly contribute to the development of autoimmune syndromes independent of classical complement receptors. The data also offer an explanation for the observation of graft accommodation in the presence of C4d deposition in ABO-incompatible renal transplantation[43]. These results might also add a facet to the comprehension of complement evasion strategies of pathogens via acquisition of complement regulator molecules such as C4b-binding protein (C4BP). C4BP binds C4b and C3b, thereby blocking the formation of or disrupting the C3 convertase of the classical or the lectin pathway of complement activation. In addition, C4BP has cofactor activity for factor I, resulting in cleavage of C4b or C3b into C4d or C3b, iC3b and C3d, respectively. It may be that in addition to defective formation of the terminal lytic complement complex on certain pathogen surfaces, the generation of these CSPs might induce pathogen-specific non-responsiveness of the host[44]. The interaction of ILT5v2 with CSPs and MHC class I molecules is the first description of any ligands for ILT5 molecules. It may be that this recently described[45] variant of ITIM-containing ILT5 might exert regulatory effects similar to those of ILT4, probably representing a form of regulatory redundancy.

The present invention refers to the following nucleotide and amino acid sequences:

The sequences provided herein are available in the NCBI database and can be retrieved from www at ncbi.nlm.nih- .gov/sites/entrez?db=gene; Theses sequences also relate to annotated and modified sequences. The present invention also provides techniques and methods wherein homologous sequences, and variants of the concise sequences provided herein are used. Preferably, such "variants" are genetic variants.

SEQ ID No. 1:

Nucleotide sequence encoding *homo sapiens* complement split product C4d (isoform C4d-A(C4Ad)). C4Ad: 1140 bases; Nucleotides 2920-4059 of C4A (NM_007293.2 GI:67190747)

```
ACCTTGGAAATACCTGGCAACTCTGATCCCAATATGATCCCTGATGGGGA
CTTTAACAGCTACGTCAGGGTTACAGCCTCAGATCCATTGGACACTTTAG
GCTCTGAGGGGGCCTTGTCACCAGGAGGCGTGGCCTCCCTCTTGAGGCTT
CCTCGAGGCTGTGGGGAGCAAACCATGATCTACTTGGCTCCGACACTGGC
TGCTTCCCGCTACCTGGACAAGACAGAGCAGTGGAGCACACTGCCTCCCG
AGACCAAGGACCACGCCGTGGATCTGATCCAGAAAGGCTACATGCGGATC
CAGCAGTTTCGGAAGGCGGATGGTTCCTATGCGGCTTGGTTGTCACGGGA
CAGCAGCACCTGGCTCACAGCCTTTGTGTTGAAGGTCCTGAGTTTGGCCC
AGGAGCAGGTAGGAGGCTCGCCTGAGAAACTGCAGGAGACATCTAACTGG
CTTCTGTCCCAGCAGCAGGCTGACGGCTCGTTCCAGGACCCTGTCCAGT
GTTAGACAGGAGCATGCAGGGGGGTTTGGTGGGCAATGATGAGACTGTGG
CACTCACAGCCTTTGTGACCATCGCCCTTCATCATGGGCTGGCCGTCTTC
CAGGATGAGGGTGCAGAGCCATTGAAGCAGAGAGTGGAAGCCTCCATCTC
AAAGGCAAACTCATTTTTGGGGGAGAAAGCAAGTGCTGGGCTCCTGGGTG
CCCACGCAGCTGCCATCACGGCCTATGCCCTGACACTGACCAAGGCGCCT
GTGGACCTGCTCGGTGTTGCCCACAACAACCTCATGGCAATGGCCCAGGA
GACTGGAGATAACCTGTACTGGGGCTCAGTCACTGGTTCTCAGAGCAATG
CCGTGTCGCCCACCCCGGCTCCTCGCAACCCATCCGACCCCATGCCCCAG
GCCCCAGCCCTGTGGATTGAAACCACAGCCTACGCCCTGCTGCACCTCCT
GCTTCACGAGGGCAAAGCAGAGATGGCAGACCAGGCTTCGGCCTGGCTCA
CCCGTCAGGGCAGCTTCCAAGGGGATTCCGCAGTACCCAAGACACGGTG
ATTGCCCTGGATGCCCTGTCTGCCTACTGGATTGCCTCCCACACCACTGA
GGAGAGGGGTCTCAATGTGACTCTCAGCTCCACAGGCCGG
```

SEQ ID No. 2:

Amino acid sequence of *homo sapiens* complement split product C4d (isoform C4d-A(C4Ad)). C4Ad amino acid sequence, 380 aa; translation of nucleotides 2920-4059 of C4A (NM_007293.2 GI:67190747) Amino acids 957-1336 of C4A

```
TLEIPGNSDPNMIPDGDFNSYVRVTASDPLDTLGSEGALSPGGVASLLRL
PRGCGEQTMIYLAPTLAASRYLDKTEQWSTLPPETKDHAVDLIQKGYMRI
QQFRKADGSYAAWLSRDSSTWLTAFVLKVLSLAQEQVGGSPEKLQETSNW
LLSQQQADGSFQDPCPVLDRSMQGGLVGNDETVALTAFVTIALHHGLAVF
QDEGAEPLKQRVEASISKANSFLGEKASAGLLGAHAAAITAYALTLTKAP
VDLLGVAHNNLMAMAQETGDNLYWGSVTGSQSNAVSPTPAPRNPSDPMPQ
APALWIETTAYALLHLLLHEGKAEMADQASAWLTRQGSFQGGFRSTQDTV
IALDALSAYWIASHTTEERGLNVTLSSTGR
```

SEQ ID No. 3:

Nucleotide sequence encoding *homo sapiens* complement split product C4d (isoform C4d-B(C4Bd)). C4Bd: 1140 bases, Nucleotides 2920-4059 of C4B (NM_001002029.3)

```
ACCTTGGAAATACCTGGCAACTCTGATCCCAATATGATCCCTGATGGGGA
CTTTAACAGCTACGTCAGGGTTACAGCCTCAGATCCATTGGACACTTTAG
GCTCTGAGGGGCCTTGTCACCAGGAGGCGTGGCCTCCCTCTTGAGGCTT
CCTCGAGGCTGTGGGGAGCAAACCATGATCTACTTGGCTCCGACACTGGC
TGCTTCCCGCTACCTGGACAAGACAGAGCAGTGGAGCACACTGCCTCCCG
AGACCAAGGACCACGCCGTGGATCTGATCCAGAAAGGCTACATGCGGATC
CAGCAGTTTCGGAAGGCGGATGGTTCCTATGCGGCTTGGTTGTCACGGGG
CAGCAGCACCTGGCTCACAGCCTTTGTGTTGAAGGTCCTGAGTTTGGCCC
AGGAGCAGGTAGGAGGCTCGCCTGAGAAACTGCAGGAGACATCTAACTGG
CTTCTGTCCCAGCAGCAGGCTGACGGCTCGTTCCAGGACCTCTCTCCAGT
GATACATAGGAGCATGCAGGGGGGTTTGGTGGGCAATGATGAGACTGTGG
CACTCACAGCCTTTGTGACCATCGCCCTTCATCATGGGCTGGCCGTCTTC
CAGGATGAGGGTGCAGAGCCATTGAAGCAGAGAGTGGAAGCCTCCATCTC
AAAGGCAAGCTCATTTTTGGGGGAGAAAGCAAGTGCTGGGCTCCTGGGTG
CCCACGCAGCTGCCATCACGGCCTATGCCCTGACACTGACCAAGGCCCCT
GCGGACCTGCGGGGTGTTGCCCACAACAACCTCATGGCAATGGCCCAGGA
GACTGGAGATAACCTGTACTGGGGCTCAGTCACTGGTTCTCAGAGCAATG
CCGTGTCGCCCACCCCGGCTCCTCGCAACCCATCCGACCCCATGCCCCAG
GCCCCAGCCCTGTGGATTGAAACCACAGCCTACGCCCTGCTGCACCTCCT
GCTTCACGAGGGCAAAGCAGAGATGGCAGACCAGGCTGCGGCCTGGCTCA
CCCGTCAGGGCAGCTTCCAAGGGGATTCCGCAGTACCCAAGACACGGTG
ATTGCCCTGGATGCCCTGTCTGCCTACTGGATTGCCTCCCACACCACTGA
GGAGAGGGGTCTCAATGTGACTCTCAGCTCCACAGGCCGG
```

SEQ ID No. 4:

Amino acid sequence of *homo sapiens* complement split product C4d (isoform C4d-B(C4Bd)). C4Bd aminoacid sequence, 380 aa; translation of Nucleotides 2920-4059 of NM_001002029.3 GI:178557738 Amino acids 957-1336 of C4B

```
TLEIPGNSDPNMIPDGDFNSYVRVTASDPLDTLGSEGALSPGGVASLLRL
PRGCGEQTMIYLAPTLAASRYLDKTEQWSTLPPETKDHAVDLIQKGYMRI
QQFRKADGSYAAWLSRGSSTWLTAFVLKVLSLAQEQVGGSPEKLQETSNW
LLSQQQADGSFQDLSPVIHRSMQGGLVGNDETVALTAFVTIALHHGLAVF
QDEGAEPLKQRVEASISKASSFLGEKASAGLLGAHAAAITAYALTLTKAP
ADLRGVAHNNLMAMAQETGDNLYWGSVTGSQSNAVSPTPAPRNPSDPMPQ
```

APALWIETTAYALLHLLLHEGKAEMADQAAAWLTRQGSFQGGFRSTQDTV

IALDALSAYWIASHTTEERGLNVTLSSTGR

SEQ ID No. 5:
Nucleotide sequence encoding *homo sapiens* complement split product C4A, alpha-chain (isoform C4A-alpha chain). C4A alpha chain nucleotide sequence encoding the C4A alpha chain (nucleotides 2089-4380) of C4A (NM_007293.2 GI:67190747)

AACGTGAACTTCCAAAAGGCGATTAATGAGAAATTGGGTCAGTATGCTTC

CCCGACAGCCAAGCGCTGCTGCCAGGATGGGGTGACACGTCTGCCCATGA

TGCGTTCCTGCGAGCAGCGGGCAGCCCGCGTGCAGCAGCCGGACTGCCGG

GAGCCCTTCCTGTCCTGCTGCCAATTTGCTGAGAGTCTGCGCAAGAAGAG

CAGGGACAAGGGCCAGGCGGGCCTCCAACGAGCCCTGGAGATCCTGCAGG

AGGAGGACCTGATTGATGAGGATGACATTCCCGTGCGCAGCTTCTTCCCA

GAGAACTGGCTCTGGAGAGTGGAAACAGTGGACCGCTTTCAAATATTGAC

ACTGTGGCTCCCCGACTCTCTGACCACGTGGGAGATCCATGGCCTGAGCC

TGTCCAAAACCAAAGGCCTATGTGTGGCCACCCCAGTCCAGCTCCGGGTG

TTCCGCGAGTTCCACCTGCACCTCCGCCTGCCCATGTCTGTCCGCCGCTT

TGAGCAGCTGGAGCTGCGGCCTGTCCTCTATAACTACCTGGATAAAAACC

TGACTGTGAGCGTCCACGTGTCCCCAGTGGAGGGCTGTGCCTGGCTGGG

GGCGGAGGGCTGGCCCAGCAGGTGCTGGTGCCTGCGGGCTCTGCCCGGCC

TGTTGCCTTCTCTGTGGTGCCCACGGCAGCCGCCGCTGTGTCTCTGAAGG

TGGTGGCTCGAGGGTCCTTCGAATTCCCTGTGGGAGATGCGGTGTCCAAG

GTTCTGCAGATTGAGAAGGAAGGGGCCATCCATAGAGAGGAGCTGGTCTA

TGAACTCAACCCCTTGGACCACCGAGGCCGGACCTTGGAAATACCTGGCA

ACTCTGATCCCAATATGATCCCTGATGGGGACTTTAACAGCTACGTCAGG

GTTACAGCCTCAGATCCATTGGACACTTTAGGCTCTGAGGGGCCTTGTC

ACCAGGAGGCGTGGCCTCCCTCTTGAGGCTTCCTCGAGGCTGTGGGGAGC

AAACCATGATCTACTTGGCTCCGACACTGGCTGCTTCCCGCTACCTGGAC

AAGACAGAGCAGTGGAGCACACTGCCTCCCGAGACCAAGGACCACGCCGT

GGATCTGATCCAGAAAGGCTACATGCGGATCCAGCAGTTTCGGAAGGCGA

ATGGTTCCTATGCGGCTTGGTTGTCACGGGACAGCAGCACCTGGCTCACA

GCCTTTGTGTTGAAGGTCCTGAGTTTGGCCCAGGAGCAGGTAGGAGGCTC

GCCTGAGAAACTGCAGGAGACATCTAACTGGCTTCTGTCCCAGCAGCAGG

CTGACGGCTCGTTCCAGGACCCCTGTCCAGTGTTAGACAGGAGCATGCAG

GGGGGTTTGGTGGGCAATGATGAGACTGTGGCACTCACAGCCTTTGTGAC

CATCGCCCTTCATCATGGGCTGGCCGTCTTCCAGGATGAGGGTGCAGAGC

CATTGAAGCAGAGAGTGGAAGCCTCCATCTCAAAGGCAAACTCATTTTTG

GGGGAGAAAGCAAGTGCTGGGCTCCTGGGTGCCCACGCAGCTGCCATCAC

GGCCTATGCCCTGACACTGACCAAGGCGCCTGTGGACCTGCTCGGTGTTG

CCCACAACAACCTCATGGCAATGGCCCAGGAGACTGGAGATAACCTGTAC

TGGGGCTCAGTCACTGGTTCTCAGAGCAATGCCGTGTCGCCCACCCCGGC

TCCTCGCAACCCATCCGACCCCATGCCCCAGGCCCCAGCCCTGTGGATTG

AAACCACAGCCTACGCCCTGCTGCACCTCCTGCTTCACGAGGGCAAAGCA

GAGATGGCAGACCAGGCTTCGGCCTGGCTCACCCGTCAGGGCAGCTTCCA

AGGGGGATTCCGCAGTACCCAAGACACGGTGATTGCCCTGGATGCCCTGT

CTGCCTACTGGATTGCCTCCCACACCACTGAGGAGAGGGGTCTCAATGTG

ACTCTCAGCTCCACAGGCCGGAATGGGTTCAAGTCCCACGCGCTGCAGCT

GAACAACCGCCAGATTCGCGGCCTGGAGGAGGAGCTGCAGTTTTCCTTGG

GCAGCAAGATCAATGTGAAGGTGGGAGGAAACAGCAAAGGAACCCTGAAG

GTCCTTCGTACCTACAATGTCCTGGACATGAAGAACACGACCTGCCAGGA

CCTACAGATAGAAGTGACAGTCAAAGGCCACGTCGAGTACACGATGGAAG

CAAACGAGGACTATGAGGACTATGAGTACGATGAGCTTCCAGCCAAGGAT

GACCCAGATGCCCCTCTGCAGCCCGTGACACCCCTGCAGCTG

SEQ ID No. 6:
Amino acid sequence of Nucleotide sequence encoding *homo sapiens* complement split product C4A, alpha-chain (isoform C4A-alpha chain). C4A alpha chain amino acid sequence mat_peptide/amino acid 680 . . . 1443 of NP_009224 (C4A)

NVNFQKAINEKLGQYASPTAKRCCQDGVTRLPMMRSCEQRAARVQQPDCR

EPFLSCCQFAESLRKKSRDKGQAGLQRALEILQEEDLIDEDDIPVRSFFP

ENWLWRVETVDRFQILTLWLPDSLTTWEIHGLSLSKTKGLCVATPVQLRV

FREFHLHLRLPMSVRRFEQLELRPVLYNYLDKNLTVSVHVSPVEGLCLAG

GGGLAQQVLVPAGSARPVAFSVVPTAAAAVSLKVVARGSFEFPVGDAVSK

VLQIEKEGAIHREELVYELNPLDHRGRTLEIPGNSDPNMIPDGDFNSYVR

VTASDPLDTLGSEGALSPGGVASLLRLPRGCGEQTMIYLAPTLAASRYLD

KTEQWSTLPPETKDHAVDLIQKGYMRIQQFRKADGSYAAWLSRDSSTWLT

AFVLKVLSLAQEQVGGSPEKLQETSNWLLSQQQADGSFQDPCPVLDRSMQ

GGLVGNDETVALTAFVTIALHHGLAVFQDEGAEPLKQRVEASISKANSFL

GEKASAGLLGAHAAAITAYALTLTKAPVDLLGVAHNNLMAMAQETGDNLY

WGSVTGSQSNAVSPTPAPRNPSDPMPQAPALWIETTAYALLHLLLHEGKA

EMADQASAWLTRQGSFQGGFRSTQDTVIALDALSAYWIASHTTEERGLNV

TLSSTGRNGFKSHALQLNNRQIRGLEEELQFSLGSKINVKVGGNSKGTLK

VLRTYNVLDMKNTTCQDLQIEVTVKGHVEYTMEANEDYEDYEYDELPAKD

DPDAPLQPVTPLQL

SEQ ID No. 7:
Nucleotide sequence encoding *homo sapiens* complement split product C4B, alpha-chain (isoform C4B-alpha chain). C4B alpha chain Nucleotide sequence encoding the C4B alpha chain (nucleotides 2089-4380) of C4B NM 001002029.3

AACGTGAACTTCCAAAAGGCGATTAATGAGAAATTGGGTCAGTATGCTTC

CCCGACAGCCAAGCGCTGCTGCCAGGATGGGGTGACACGTCTGCCCATGA

TGCGTTCCTGCGAGCAGCGGGCAGCCCGCGTGCAGCAGCCGGACTGCCGG

```
GAGCCCTTCCTGTCCTGCTGCCAATTTGCTGAGAGTCTGCGCAAGAAGAG

CAGGGACAAGGGCCAGGCGGGCCTCCAACGAGCCCTGGAGATCCTGCAGG

AGGAGGACCTGATTGATGAGGATGACATTCCCGTGCGCAGCTTCTTCCCA

GAGAACTGGCTCTGGAGAGTGGAAACAGTGGACCGCTTTCAAATATTGAC

ACTGTGGCTCCCCGACTCTCTGACCACGTGGGAGATCCATGGCCTGAGCC

TGTCCAAAACCAAAGGCCTATGTGTGGCCACCCCAGTCCAGCTCCGGGTG

TTCCGCGAGTTCCACCTGCACCTCCGCCTGCCCATGTCTGTCCGCCGCTT

TGAGCAGCTGGAGCTGCGGCCTGTCCTCTATAACTACCTGGATAAAAACC

TGACTGTGAGCGTCCACGTGTCCCCAGTGGAGGGGCTGTGCCTGGCTGGG

GGCGAGAGGGCTGGCCCAGCAGGTGCTGGTGCCTGCGGGCTCTGCCCGGCC

TGTTGCCTTCTCTGTGGTGCCCACGGCAGCCACCGCTGTGTCTCTGAAGG

TGGTGGCTCGAGGGTCCTTCGAATTCCCTGTGGGAGATGCGGTGTCCAAG

GTTCTGCAGATTGAGAAGGAAGGGGCCATCCATAGAGAGGAGCTGGTCTA

TGAACTCAACCCCTTGGACCACCGAGGCCGGACCTTGGAAATACCTGGCA

ACTCTGATCCCAATATGATCCCTGATGGGGACTTTAACAGCTACGTCAGG

GTTACAGCCTCAGATCCATTGGACACTTTAGGCTCTGAGGGGCCTTGTC

ACCAGGAGGCGTGGCCTCCCTCTTGAGGCTTCCTCGAGGCTGTGGGGAGC

AAACCATGATCTACTTGGCTCCGACACTGGCTGCTTCCCGCTACCTGGAC

AAGACAGAGCAGTGGAGCACACTGCCTCCCGAGACCAAGGACCACGCCGT

GGATCTGATCCAGAAAGGCTACATGCGGATCCAGCAGTTTCGGAAGGCGG

ATGGTTCCTATGCGGCTTGGTTGTCACGGGGCAGCAGCACCTGGCTCACA

GCCTTTGTGTTGAAGGTCCTGAGTTTGGCCCAGGAGCAGGTAGGAGGCTC

GCCTGAGAAACTGCAGGAGACATCTAACTGGCTTCTGTCCCAGCAGCAGG

CTGACGGCTCGTTCCAGGACCTCTCTCCAGTGATACATAGGAGCATGCAG

GGGGGTTTGGTGGGCAATGATGAGACTGTGGCACTCACAGCCTTTGTGAC

CATCGCCCTTCATCATGGGCTGGCCGTCTTCCAGGATGAGGGTGCAGAGC

CATTGAAGCAGAGAGTGGAAGCCTCCATCTCAAAGGCAAGCTCATTTTTG

GGGGAGAAAGCAAGTGCTGGGCTCCTGGGTGCCCACGCAGCTGCCATCAC

GGCCTATGCCCTGACACTGACCAAGGCCCCTGCGGACCTGCGGGGTGTTG

CCCACAACAACCTCATGGCAATGGCCCAGGAGACTGGAGATAACCTGTAC

TGGGGCTCAGTCACTGGTTCTCAGAGCAATGCCGTGTCGCCCACCCCGGC

TCCTCGCAACCCATCCGACCCCATGCCCCAGGCCCCAGCCCTGTGGATTG

AAACCACAGCCTACGCCCTGCTGCACCTCCTGCTTCACGAGGGCAAAGCA

GAGATGGCAGACCAGGCTGCGGCCTGGCTCACCCGTCAGGGCAGCTTCCA

AGGGGGATTCCGCAGTACCCAAGACACGGTGATTGCCCTGGATGCCCTGT

CTGCCTACTGGATTGCCTCCCACACCACTGAGGAGAGGGGTCTCAATGTG

ACTCTCAGCTCACAGGCCGGAATGGGTTCAAGTCCCACGCGCTGCAGCT

GAACAACCGCCAGATTCGCGGCCTGGAGGAGGAGCTGCAGTTTTCCTTGG

GCAGCAAGATCAATGTGAAGGTGGGAGGAAACAGCAAAGGAACCCTGAAG

GTCCTTCGTACCTACAATGTCCTGGACATGAAGAACACGACCTGCCAGGA

CCTACAGATAGAAGTGACAGTCAAAGGCCACGTCGAGTACACGATGGAAG
```

```
CAAACGAGGACTATGAGGACTATGAGTACGATGAGCTTCCAGCCAAGGAT

GACCCAGATGCCCCTCTGCAGCCCGTGACACCCCTGCAGCTG
```

SEQ ID No. 8:

Amino acid sequence of *homo sapiens* complement split product C4B, alpha-chain (isoform C4B-alpha chain). C4B alpha chain amino acid sequence mat_peptide/amino acid 680 . . . 1443 of NP_001002029.3 (C4B)

```
NVNFQKAINEKLGQYASPTAKRCCQDGVTRLPMMRSCEQRAARVQQPDCR

EPFLSCCQFAESLRKKSRDKGQAGLQRALEILQEEDLIDEDDIPVRSFFP

ENWLWRVETVDRFQILTLWLPDSLTTWEIHGLSLSKTKGLCVATPVQLRV

FREFHLHLRLPMSVRRFEQLELRPVLYNYLDKNLTVSVHVSPVEGLCLAG

GGGLAQQVLVPAGSARPVAFSVVPTAATAVSLKVVARGSFEFPVGDAVSK

VLQIEKEGAIHREELVYELNPLDHRGRTLEIPGNSDPNMIPDGDFNSYVR

VTASDPLDTLGSEGALSPGGVASLLRLPRGCGEQTMIYLAPTLAASRYLD

KTEQWSTLPPETKDHAVDLIQKGYMRIQQFRKADGSYAAWLSRGSSTWLT

AFVLKVLSLAQEQVGGSPEKLQETSNWLLSQQQADGSFQDLSPVIHRSMQ

GGLVGNDETVALTAFVTIALHHGLAVFQDEGAEPLKQRVEASISKASSFL

GEKASAGLLGAHAAAITAYALTLTKAPADLRGVAHNNLMAMAQETGDNLY

WGSVTGSQSNAVSPTPAPRNPSDPMPQAPALWIETTAYALLHLLLHEGKA

EMADQAAAWLTRQGSFQGGFRSTQDTVIALDALSAYWIASHTTEERGLNV

TLSSTGRNGFKSHALQLNNRQIRGLEEELQFSLGSKINVKVGGNSKGTLK

VLRTYNVLDMKNTTCQDLQIEVTVKGHVEYTMEANEDYEDYEYDELPAKD

DPDAPLQPVTPLQL
```

SEQ ID No. 9:

Nucleotide sequence encoding *homo sapiens* ILT4. The coding region ranges from nucleotide 199 to nucleotide 2036. Human ILT-4 NM_005874 2913 by mRNA; *Homo sapiens* leukocyte immunoglobulin-like receptor, subfamily B (with TM and ITIM domains), member 2 (LILRB2), transcript variant 1, mRNA. ACCESSION NM_005874, VERSION NM_005874.2 GI:125988399

```
AGTGTCAAGAAAGAAGTCAACTTTTCTTCCCCTACTTCCCTGCATTTCTC

CTCTGTGCTCACTGCCACACGCAGCTCAACCTGGACGGCACAGCCAGAGG

CGAGATGCTTCTCTGCTGATCTGAGTCTGCCTGCAGCATGGACCTGGGTC

TTCCCTGAAGCATCTCCAGGGCTGGAGGGACGACTGCCATGCACCGAGGG

CTCATCCATCCGCAGAGCAGGGCAGTGGGAGGAGACGCCATGACCCCCAT

CGTCACAGTCCTGATCTGTCTCGGGCTGAGTCTGGGCCCCAGGACCCACG

TGCAGACAGGGACCATTCCCAAGCCCACCCTGTGGGCTGAGCCAGACTCT

GTGATCACCCAGGGGAGTCCCGTCACCCTCAGTTGTCAGGGGAGCCTTGA

AGCCCAGGAGTACCGTCTATATAGGGAGAAAAAATCAGCATCTTGGATTA

CACGGATACGACCAGAGCTTGTGAAGAACGGCCAGTTCCACATCCCATCC

ATCACCTGGGAACACACAGGGCGATATGGCTGTCAGTATTACAGCCGCGC

TCGGTGGTCTGAGCTCAGTGACCCCCTGGTGCTGGTGATGACAGGAGCCT
```

```
ACCCAAAACCCACCCTCTCAGCCCAGCCCAGCCCTGTGGTGACCTCAGGA
GGAAGGGTGACCCTCCAGTGTGAGTCACAGGTGGCATTTGGCGGCTTCAT
TCTGTGTAAGGAAGGAGAAGAAGAACACCCACAATGCCTGAACTCCCAGC
CCCATGCCCGTGGGTCGTCCCGCGCCATCTTCTCCGTGGGCCCCGTGAGC
CCGAATCGCAGGTGGTCGCACAGGTGCTATGGTTATGACTTGAACTCTCC
CTATGTGTGGTCTTCACCCAGTGATCTCCTGGAGCTCCTGGTCCCAGGTG
TTTCTAAGAAGCCATCACTCTCAGTGCAGCCGGGTCCTGTCGTGGCCCCT
GGGGAAAGCCTGACCCTCCAGTGTGTCTCTGATGTCGGCTATGACAGATT
TGTTCTGTACAAGGAGGGGAACGTGACCTTCGCCAGCTCCCTGGCCGGC
AGCCCCAGGCTGGGCTCTCCCAGGCCAACTTCACCCTGGGCCCTGTGAGC
CGCTCCTACGGGGGCCAGTACAGATGCTACGGTGCACACAACCTCTCCTC
TGAGTGCTCGGCCCCCAGCGACCCCCTGGACATCCTGATCACAGGACAGA
TCCGTGGCACACCCTTCATCTCAGTGCAGCCAGGCCCCACAGTGGCCTCA
GGAGAGAACGTGACCCTGCTGTGTCAGTCATGGCGGCAGTTCCACACTTT
CCTTCTGACCAAGGCGGGAGCAGCTGATGCCCCACTCCGTCTAAGATCAA
TACACGAATATCCTAAGTACCAGGCTGAATTCCCCATGAGTCCTGTGACC
TCAGCCCACGCGGGGACCTACAGGTGCTACGGCTCACTCAACTCCGACCC
CTACCTGCTGTCTCACCCCAGTGAGCCCCTGGAGCTCGTGGTCTCAGGAC
CCTCCATGGGTTCCAGCCCCCCACCCACCGGTCCCATCTCCACACCTGCA
GGCCCTGAGGACCAGCCCCTCACCCCCACTGGGTCGGATCCCCAAAGTGG
TCTGGGAAGGCACCTGGGGGTTGTGATCGGCATCTTGGTGGCCGTCGTCC
TACTGCTCCTCCTCCTCCTCCTCTTCCTCATCCTCCGACATCGACGT
CAGGGCAAACACTGGACATCGACCCAGAGAAAGGCTGATTTCCAACATCC
TGCAGGGCTGTGGGGCCAGAGCCCACAGACAGAGGCCTGCAGTGGAGGT
CCAGCCCAGCTGCCGACGCCCAGGAAGAAAACCTCTATGCTGCCGTGAAG
GACACACAGCCTGAAGATGGGGTGGAGATGGACACTCGGGCTGCTGCATC
TGAAGCCCCCAGGATGTGACCTACGCCCAGCTGCACAGCTTGACCCTCA
GACGGAAGGCAACTGAGCCTCCTCCATCCCAGGAAAGGGAACCTCCAGCT
GAGCCCAGCATCTACGCCACCCTGGCCATCCACTAGCCCGGAGGGTACGC
AGACTCCACACTCAGTAGAAGGAGACTCAGGACTGCTGAAGGCACGGGAG
CTGCCCCCAGTGGACACCAATGAACCCCAGTCAGCCTGGACCCCTAACAA
AGACCATGAGGAGATGCTGGGAACTTTGGGACTCACTTGATTCTGCAGTC
GAAATAACTAATATCCCTACATTTTTAATTAAAGCAACAGACTTCTCAA
TAATCAATGAGTTAACCGAGAAAACTAAAATCAGAAGTAAGAATGTGCTT
TAAACTGAATCACAATATAAATATTACACATCACACAATGAAATTGAAAA
AGTACAAACCACAAATGAAAAAGTAGAAACGAAAAAAAAAAACTAGGAA
ATGAATGACGTTGGCTTTCGTATAAGGAATTTAGAAAAAGAATAACCAAT
TATTCCAAATGAAGGTGTAAGAAAGGGAATAAGAAGAAGAAGAGTTGCTC
ATGAGGAAAAACCAAAACTTGAAAATTCAACAAAGCCAATGAAGCTCATT
CTTGAAAATATTAATTACAGTCATAAATCCTAACTACATTGAGCAAGAGA
AAGAAAGAGCAGGCACGCATTTCCATATGGGAGTGAGCCAGCAGACAGCC
CAGCAGATCCTACACACATTTTCACAAACTAACCCCAGAACAGGCTGCAA
ACCTATACCAATATACTAGAAAATGCAGATTAAATGGATGAAATATTCAA
AACTGGAGTTTACATAATGAACGTAAGAGTAATCAGAGAATCTGACTCAT
TTTAAATGTGTGTGTATGTGTGTGTATATATATGTGTGTGTGTGTGTG
TGTGTGTGTGAAAAACATTGACTGTAATAAAAATGTTCCCATCGTAAA
AAAAAAAAAAAA
```

SEQ ID No. 10:
Amino acid sequence of *homo sapiens* ILT4. Human ILT-4 amino acid sequence (NM_005874 NM_005874.2), coding region translated (from 240-2036; 598 aa)

```
MTPIVTVLICLGLSLGPRTHVQTGTIPKPTLWAEPDSVITQGSPVTLSCQ
GSLEAQEYRLYREKKSASWITRIRPELVKNGQFHIPSITWEHTGRYGCQY
YSRARWSELSDPLVLVMTGAYPKPTLSAQPSPVVTSGGRVTLQCESQVAF
GGFILCKEGEEEHPQCLNSQPHARGSSRAIFSVGPVSPNRRWSHRCYGYD
LNSPYVWSSPSDLLELLVPGVSKKPSLSVQPGPVVAPGESLTLQCVSDVG
YDRFVLYKEGERDLRQLPGRQPQAGLSQANFTLGPVSRSYGGQYRCYGAH
NLSSECSAPSDPLDILITGQIRGTPFISVQPGPTVASGENVTLLCQSWRQ
FHTFLLTKAGAADAPLRLRSIHEYPKYQAEFPMSPVTSAHAGTYRCYGSL
NSDPYLLSHPSEPLELVVSGPSMGSSPPPTGPISTPAGPEDQPLTPTGSD
PQSGLGRHLGVVIGILVAVVLLLLLLLLLFLILRHRRQGKHWTSTQRKAD
FQHPAGAVGPEPTDRGLQWRSSPAADAQEENLYAAVKDTQPEDGVEMDTR
AAASEAPQDVTYAQLHSLTLRRKATEPPPSQEREPPAEPSIYATLAIH
```

All references cited herein are fully incorporated by reference. Having now fully described the invention, it will be understood by a person skilled in the art that the invention may be practiced within a wide and equivalent range of conditions, parameters and the like, without affecting the spirit or scope of the invention or any embodiment thereof.

REFERENCES

1. Kao A H, Navratil J S, Ruffing M J, et al. Erythrocyte C3d and C4d for monitoring disease activity in systemic lupus erythematosus. Arthritis and rheumatism 2010; 62(3): 837-44.
2. Liu C C, Kao A H, Hawkins D M, et al. Lymphocyte-bound complement activation products as biomarkers for diagnosis of systemic lupus erythematosus. Clinical and translational science 2009; 2(4):300-8.
3. Racusen L C, Colvin R B, Solez K, et al. Antibody-mediated rejection criteria—an addition to the Banff 97 classification of renal allograft rejection. Am J Transplant 2003; 3(6):708-14.
4. Colonna M, Samaridis J, Cella M, et al. Human myelomonocytic cells express an inhibitory receptor for classical and nonclassical MHC class I molecules. J Immunol 1998; 160(7):3096-100.
5. Hunt J S, Petroff M G, McIntire R H, Ober C. HLA-G and immune tolerance in pregnancy. Faseb J 2005; 19(7):681-93.
6. LeMaoult J, Zafaranloo K, Le Danff C, Carosella E D. HLA-G up-regulates ILT2, ILT3, ILT4, and KIR2DL4 in antigen presenting cells, NK cells, and T cells. Faseb J 2005; 19(6):662-4.

7. Ristich V, Liang S, Zhang W, Wu J, Horuzsko A. Tolerization of dendritic cells by HLA-G. European journal of immunology 2005; 35(4): 1133-42.
8. Campbell R D, Dodds A W, Porter R R. The binding of human complement component C4 to antibody-antigen aggregates. The Biochemical journal 1980; 189(1):67-80.
9. Dommett R M, Klein N, Turner M W. Mannose-binding lectin in innate immunity: past, present and future. Tissue antigens 2006; 68(3):193-209.
10. Korb L C, Ahearn J M. C1q binds directly and specifically to surface blebs of apoptotic human keratinocytes: complement deficiency and systemic lupus erythematosus revisited. J Immunol 1997; 158(10):4525-8.
11. Law S K, Dodds A W. The internal thioester and the covalent binding properties of the complement proteins C3 and C4. Protein Sci 1997; 6(2):263-74.
12. Nauta A J, Trouw L A, Daha M R, et al. Direct binding of C1q to apoptotic cells and cell blebs induces complement activation. European journal of immunology 2002; 32(6):1726-36.
13. Taylor P R, Carugati A, Fadok V A, et al. A hierarchical role for classical pathway complement proteins in the clearance of apoptotic cells in vivo. The Journal of experimental medicine 2000; 192(3):359-66.
14. Bohmig G A, Exner M, Habicht A, et al. Capillary C4d deposition in kidney allografts: a specific marker of alloantibody-dependent graft injury. J Am Soc Nephrol 2002; 13(4):1091-9.
15. Mauiyyedi S, Crespo M, Collins A B, et al. Acute humoral rejection in kidney transplantation: II. Morphology, immunopathology, and pathologic classification. J Am Soc Nephrol 2002; 13(3):779-87.
16. Steinberger P, Majdic O, Derdak S V, et al. Molecular characterization of human 4Ig-B7-H3, a member of the B7 family with four Ig-like domains. J Immunol 2004; 172(4):2352-9.
17. Colonna M, Navarro F, Bellon T, et al. A common inhibitory receptor for major histocompatibility complex class I molecules on human lymphoid and myelomonocytic cells. The Journal of experimental medicine 1997; 186(11):1809-18.
18. Cosman D, Fanger N, Borges L, et al. A novel immunoglobulin superfamily receptor for cellular and viral MHC class I molecules. Immunity 1997; 7(2):273-82.
19. Fanger N A, Cosman D, Peterson L, Braddy S C, Maliszewski C R, Borges L. The MHC class I binding proteins LIR-1 and LIR-2 inhibit Fc receptor-mediated signaling in monocytes. European journal of immunology 1998; 28(11):3423-34.
20. Anderson K J, Allen R L. Regulation of T-cell immunity by leucocyte immunoglobulin-like receptors: innate immune receptors for self on antigen-presenting cells. Immunology 2009; 127(1):8-17.
21. Chang C C, Ciubotariu R, Manavalan J S, et al. Tolerization of dendritic cells by T(S) cells: the crucial role of inhibitory receptors ILT3 and ILT4. Nature immunology 2002; 3 (3):237-43.
22. Le Rond S, Azema C, Krawice-Radanne I, et al. Evidence to support the role of HLA-G5 in allograft acceptance through induction of immunosuppressive/regulatory T cells. J Immunol 2006; 176(5):3266-76.
23. Manavalan J S, Kim-Schulze S, Scotto L, et al. Alloantigen specific CD8+CD28-FOXP3+T suppressor cells induce ILT3+ ILT4+ tolerogenic endothelial cells, inhibiting alloreactivity. International immunology 2004; 16(8):1055-68.
24. Manavalan J S, Rossi P C, Vlad G, et al. High expression of ILT3 and ILT4 is a general feature of tolerogenic dendritic cells. Transplant immunology 2003; 11(3-4):245-58.
25. Ristich V, Zhang W, Liang S, Horuzsko A. Mechanisms of prolongation of allograft survival by HLA-G/ILT4-modified dendritic cells. Human immunology 2007; 68(4):264-71.
26. Allan D S, Colonna M, Lanier L L, et al. Tetrameric complexes of human histocompatibility leukocyte antigen (HLA)-G bind to peripheral blood myelomonocytic cells. The Journal of experimental medicine 1999; 189(7):1149-56.
27. Borges L, Hsu M L, Fanger N, Kubin M, Cosman D. A family of human lymphoid and myeloid Ig-like receptors, some of which bind to MHC class I molecules. J Immunol 1997; 159(11):5192-6.
28. Lepin E J, Bastin J M, Allan D S, et al. Functional characterization of HLA-F and binding of HLA-F tetramers to ILT2 and ILT4 receptors. European journal of immunology 2000; 30(12):3552-61.
29. Navarro F, Llano M, Bellon T, Colonna M, Geraghty D E, Lopez-Botet M. The ILT2(LIR1) and CD94/NKG2A NK cell receptors respectively recognize HLA-G1 and HLA-E molecules co-expressed on target cells. European journal of immunology 1999; 29(1):277-83.
30. Vitale M, Castriconi R, Parolini S, et al. The leukocyte Ig-like receptor (LIR)-1 for the cytomegalovirus UL18 protein displays a broad specificity for different HLA class I alleles: analysis of LIR-1+NK cell clones. International immunology 1999; 11(1):29-35.
31. Borges L, Cosman D. LIRs/ILTs/MIRs, inhibitory and stimulatory Ig-superfamily receptors expressed in myeloid and lymphoid cells. Cytokine & growth factor reviews 2000; 11(3):209-17.
32. Kubo T, Uchida Y, Watanabe Y, et al. Augmented TLR9-induced Btk activation in PIR-B-deficient B-1 cells provokes excessive autoantibody production and autoimmunity. The Journal of experimental medicine 2009; 206(9):1971-82.
33. Nakamura A, Kobayashi E, Takai T. Exacerbated graft-versus-host disease in Pirb−/− mice. Nature immunology 2004; 5(6):623-9.
34. Botto M, Kirschfink M, Macor P, Pickering M C, Wurzner R, Tedesco F. Complement in human diseases: Lessons from complement deficiencies. Molecular immunology 2009; 46(14):2774-83.
35. Pickering M C, Botto M, Taylor P R, Lachmann P J, Walport M J. Systemic lupus erythematosus, complement deficiency, and apoptosis. Advances in immunology 2000; 76:227-324.
36. Yang Y, Chung E K, Wu Y L, et al. Gene copy-number variation and associated polymorphisms of complement component C4 in human systemic lupus erythematosus (SLE): low copy number is a risk factor for and high copy number is a protective factor against SLE susceptibility in European Americans. Am J Hum Genet 2007; 80(6):1037-54.
37. Chen Z, Koralov S B, Kelsoe G. Complement C4 inhibits systemic autoimmunity through a mechanism independent of complement receptors CR1 and CR2. The Journal of experimental medicine 2000; 192(9):1339-52.
38. Gaipl U S, Voll R E, Sheriff A, Franz S, Kalden J R, Herrmann M. Impaired clearance of dying cells in systemic lupus erythematosus. Autoimmunity reviews 2005; 4(4):189-94.

39. Helmy K Y, Katschke K J, Jr., Gorgani N N, et al. CRIg: a macrophage complement receptor required for phagocytosis of circulating pathogens. Cell 2006; 124(5):915-27.
40. Khera R, Das N. Complement Receptor 1: disease associations and therapeutic implications. Molecular immunology 2009; 46(5):761-72.
41. Mevorach D. Clearance of dying cells and systemic lupus erythematosus: the role of C1q and the complement system. Apoptosis 2010; 15(9): 1114-23.
42. Munoz L E, Janko C, Chaurio R A, Schett G, Gaipl U S, Herrmann M. IgG opsonized nuclear remnants from dead cells cause systemic inflammation in SLE. Autoimmunity 2010; 43(3):232-5.
43. Haas M, Segev D L, Racusen L C, et al. C4d deposition without rejection correlates with reduced early scarring in ABO-incompatible renal allografts. J Am Soc Nephrol 2009; 20(1): 197-204.
44. Blom A M, Hallstrom T, Riesbeck K. Complement evasion strategies of pathogens-acquisition of inhibitors and beyond. Molecular immunology 2009; 46(14):2808-17.
45. Pfistershammer K, Lawitschka A, Klauser C, et al. Allogeneic disparities in immunoglobulin-like transcript 5 induce potent antibody responses in hematopoietic stem cell transplant recipients. Blood 2009; 114(11):2323-32.
46. Clemenza L, Isenman D E. The C4A and C4B isotypic forms of human complement fragment C4b have the same intrinsic affinity for complement receptor 1 (CR1/CD35). J Immunol 2004; 172(3):1670-80.
47. Nagar B, Jones R G, Diefenbach R J, Isenman D E, Rini J M. X-ray crystal structure of C3d: a C3 fragment and ligand for complement receptor 2. Science (New York, N.Y. 1998; 280(5367): 1277-81.
48. van den Elsen J M, Martin A, Wong V, Clemenza L, Rose D R, Isenman D E. X-ray crystal structure of the C4d fragment of human complement component C4. Journal of molecular biology 2002; 322(5):1103-15.
49. Leitner J, Kuschei W, Grabmeier-Pfistershammer K, et al. T cell stimulator cells, an efficient and versatile cellular system to assess the role of costimulatory ligands in the activation of human T cells. Journal of immunological methods 2010; 362(1-2):131-41.
50. Kober J, Leitner J, Klauser C, et al. The capacity of the TNF family members 4-1BBL, OX40L, CD70, GITRL, CD30L and LIGHT to costimulate human T cells. European journal of immunology 2008; 38(10):2678-88.
51. Leitner J, Klauser C, Pickl W F, et al. B7-H3 is a potent inhibitor of human T-cell activation: No evidence for B7-H3 and TREML2 interaction. European journal of immunology 2009; 39(7): 1754-64.

The invention claimed is:

1. A method of treating a patient suffering from an arthritic condition, wherein said method comprises administering to the patient a therapeutically effective amount of a pharmaceutical composition comprising a polypeptide consisting of the amino acid sequence of SEQ ID NO:2 or SEQ ID NO:4 or a fragment of SEQ ID NO:2 or SEQ ID NO:4, wherein said fragment
   has up to 30 amino acids deleted from the N-terminus of SEQ ID NO:2 or SEQ ID NO:4.

2. The method of claim 1, wherein the pharmaceutical composition comprises a multimer of said polypeptide.

3. The method of claim 1, wherein the arthritic condition is selected from rheumatoid arthritis, erosive arthritis, or juvenile arthritis.

4. A method of suppressing or ameliorating an excessive immune response associated with elevated levels of TNF-α and IL6 in a patient suffering from an arthritic condition, wherein said method comprises administering to the patient a therapeutically effective amount of a pharmaceutical composition comprising a polypeptide consisting of the amino acid sequence of SEQ ID NO:2 or SEQ ID NO:4 or a fragment of SEQ ID NO:2 or SEQ ID NO:4, wherein said fragment
   has up to 30 amino acids deleted from the N-terminus of SEQ ID NO:2 or SEQ ID NO:4.

5. The method of claim 2, wherein the multimer is a homo-multimer.

6. The method of claim 2, wherein the polypeptides of the multimer are attached by a linker.

7. The method of claim 6, wherein the linker is flexible linker composed of glycine or serine residues.

8. The method of claim 1, wherein said polypeptide is SEQ ID NO:2.

9. The method of claim 8, wherein the arthritic condition is selected from rheumatoid arthritis, erosive arthritis, or juvenile arthritis.

10. The method of claim 8, wherein the pharmaceutical composition comprises a multimer of said polypeptide.

11. The method of claim 10, wherein the multimer is a homo-multimer.

12. The method of claim 11, wherein the multimer comprises from 2 to up to 20 polypeptides.

13. The method of claim 12, wherein the polypeptides of the multimer are attached by a linker.

14. The method of claim 13, wherein the linker is flexible linker composed of glycine or serine residues.

15. The method of claim 12, wherein the multimer comprises 4 polypeptides.

16. The method of claim 15, wherein the polypeptides of the multimer are attached by a linker.

17. The method of claim 16, wherein the linker is flexible linker composed of glycine or serine residues.

18. The method of claim 10, wherein the arthritic condition is selected from rheumatoid arthritis, erosive arthritis or juvenile arthritis.

19. The method of claim 4, wherein said polypeptide is SEQ ID NO:2.

20. The method of claim 19, wherein the pharmaceutical composition comprises a multimer of said polypeptide.

21. The method of claim 20, wherein the multimer is a homo-multimer.

22. The method of claim 21, wherein the multimer comprises from 2 to up to 20 polypeptides.

23. The method of claim 22, wherein the polypeptides of the multimer are attached by a linker.

24. The method of claim 23, wherein the linker is flexible linker composed of glycine or serine residues.

25. The method of claim 22, wherein the multimer comprises 4 polypeptides.

26. The method of claim 25, wherein the polypeptides of the multimer are attached by a linker.

27. The method of claim 26, wherein the linker is flexible linker composed of glycine or serine residues.

28. The method of claim 1, wherein said polypeptide is the fragment of SEQ ID NO:2 or SEQ ID NO:4.

29. The method of claim 4, wherein said polypeptide is the fragment of SEQ ID NO:2 or SEQ ID NO:4.

30. The method of claim 1, wherein said polypeptide is SEQ ID NO:4.

31. The method of claim 4, wherein said polypeptide is SEQ ID NO:4.

\* \* \* \* \*

SEQUENCE LISTING

```
<160> NUMBER OF SEQ ID NOS: 13

<210> SEQ ID NO 1
<211> LENGTH: 1140
<212> TYPE: DNA
<213> ORGANISM: Homo sapiens
<220> FEATURE:
<221> NAME/KEY: source
<222> LOCATION: 1..1140
<223> OTHER INFORMATION: /mol_type="unassigned DNA"
      /organism="Homo sapiens"

<400> SEQUENCE: 1
accttggaaa tacctggcaa ctctgatccc aatatgatcc ctgatgggga ctttaacagc      60
tacgtcaggg ttacagcctc agatccattg gacactttag gctctgaggg ggccttgtca     120
ccaggaggcg tggcctccct cttgaggctt cctcgaggct gtggggagca aaccatgatc     180
tacttggctc cgacactggc tgcttcccgc tacctggaca agacagagca gtggagcaca     240
ctgcctcccg agaccaagga ccacgccgtg gatctgatcc agaaaggcta catgcggatc     300
cagcagtttc ggaaggcgga tggttcctat gcggcttggt tgtcacggga cagcagcacc     360
tggctcacag cctttgtgtt gaaggtcctg agtttggccc aggagcaggt aggaggctcg     420
cctgagaaac tgcaggagac atctaactgg cttctgtccc agcagcaggc tgacggctcg     480
ttccaggacc cctgtccagt gttagacagg agcatgcagg ggggtttggt gggcaatgat     540
gagactgtgg cactcacagc ctttgtgacc atcgccttc atcatgggct ggccgtcttc     600
caggatgagg gtgcagagcc attgaagcag agagtggaag cctccatctc aaaggcaaac     660
tcattttggg gggagaaagc aagtgctggg ctcctgggtg cccacgcagc tgccatcacg     720
gcctatgccc tgacactgac caaggcgcct gtggacctgc tcggtgttgc ccacaacaac     780
ctcatggcaa tggcccagga gactggagat aacctgtact ggggctcagt cactggttct     840
cagagcaatg ccgtgtcgcc caccccggct cctcgcaacc catccgaccc catgcccag      900 gccccagccc tgtggattga aaccacagcc tacgccctgc tgcacctcct gcttcacgag     960
```

-continued

```
ggcaaagcag agatggcaga ccaggcttcg gcctggctca cccgtcaggg cagcttccaa    1020
gggggattcc gcagtaccca agacacggtg attgccctgg atgccctgtc tgcctactgg    1080
attgcctccc acaccactga ggagagggt ctcaatgtga ctctcagctc cacaggccgg    1140
```

<210> SEQ ID NO 2
<211> LENGTH: 380
<212> TYPE: PRT
<213> ORGANISM: Homo sapiens

<400> SEQUENCE: 2

```
Thr Leu Glu Ile Pro Gly Asn Ser Asp Pro Asn Met Ile Pro Asp Gly
1               5                   10                  15

Asp Phe Asn Ser Tyr Val Arg Val Thr Ala Ser Pro Leu Asp Thr
                20                  25                  30

Leu Gly Ser Glu Gly Ala Leu Ser Pro Gly Val Ala Ser Leu Leu
            35                  40                  45

Arg Leu Pro Arg Gly Cys Gly Glu Gln Thr Met Ile Tyr Leu Ala Pro
    50                  55                  60

Thr Leu Ala Ala Ser Arg Tyr Leu Asp Lys Thr Glu Gln Trp Ser Thr
65                  70                  75                  80

Leu Pro Pro Glu Thr Lys Asp His Ala Val Asp Leu Ile Gln Lys Gly
                85                  90                  95

Tyr Met Arg Ile Gln Gln Phe Arg Lys Ala Asp Gly Ser Tyr Ala Ala
                100                 105                 110

Trp Leu Ser Arg Asp Ser Ser Thr Trp Leu Thr Ala Phe Val Leu Lys
            115                 120                 125

Val Leu Ser Leu Ala Gln Glu Gln Val Gly Gly Ser Pro Glu Lys Leu
    130                 135                 140

Gln Glu Thr Ser Asn Trp Leu Leu Ser Gln Gln Ala Asp Gly Ser
145                 150                 155                 160

Phe Gln Asp Pro Cys Pro Val Leu Asp Arg Ser Met Gln Gly Gly Leu
                165                 170                 175

Val Gly Asn Asp Glu Thr Val Ala Leu Thr Ala Phe Val Thr Ile Ala
                180                 185                 190

Leu His His Gly Leu Ala Val Phe Gln Asp Glu Gly Ala Glu Pro Leu
            195                 200                 205

Lys Gln Arg Val Glu Ala Ser Ile Ser Lys Ala Asn Ser Phe Leu Gly
    210                 215                 220

Glu Lys Ala Ser Ala Gly Leu Leu Gly Ala His Ala Ala Ala Ile Thr
225                 230                 235                 240

Ala Tyr Ala Leu Thr Leu Thr Lys Ala Pro Val Asp Leu Leu Gly Val
                245                 250                 255

Ala His Asn Asn Leu Met Ala Met Ala Gln Glu Thr Gly Asp Asn Leu
                260                 265                 270

Tyr Trp Gly Ser Val Thr Gly Ser Gln Ser Asn Ala Val Ser Pro Thr
            275                 280                 285

Pro Ala Pro Arg Asn Pro Ser Asp Pro Met Pro Gln Ala Pro Ala Leu
    290                 295                 300

Trp Ile Glu Thr Thr Ala Tyr Ala Leu Leu His Leu Leu Leu His Glu
305                 310                 315                 320

Gly Lys Ala Glu Met Ala Asp Gln Ala Ser Ala Trp Leu Thr Arg Gln
                325                 330                 335

Gly Ser Phe Gln Gly Gly Phe Arg Ser Thr Gln Asp Thr Val Ile Ala
            340                 345                 350
```

```
Leu Asp Ala Leu Ser Ala Tyr Trp Ile Ala Ser His Thr Thr Glu Glu
            355                 360                 365

Arg Gly Leu Asn Val Thr Leu Ser Ser Thr Gly Arg
    370                 375                 380

<210> SEQ ID NO 3
<211> LENGTH: 1140
<212> TYPE: DNA
<213> ORGANISM: Homo sapiens
<220> FEATURE:
<221> NAME/KEY: source
<222> LOCATION: 1..1140
<223> OTHER INFORMATION: /mol_type="unassigned DNA"
      /organism="Homo sapiens"

<400> SEQUENCE: 3
accttggaaa tacctggcaa ctctgatccc aatatgatcc ctgatgggga ctttaacagc      60
tacgtcaggg ttacagcctc agatccattg acactttag gctctgaggg ggccttgtca     120
ccaggaggcg tggcctccct cttgaggctt cctcgaggct gtggggagca aaccatgatc     180
tacttggctc cgacactggc tgcttcccgc tacctggaca agacagagca gtggagcaca     240
ctgcctcccg agaccaagga ccacgccgtg gatctgatcc agaaaggcta catgcggatc     300
cagcagtttc ggaaggcgga tggttcctat gcggcttggt tgtcacgggg cagcagcacc     360
tggctcacag cctttgtgtt gaaggtcctg agtttggccc aggagcaggt aggaggctcg     420
cctgagaaac tgcaggagac atctaactgg cttctgtccc agcagcaggc tgacggctcg     480
ttccaggacc tctctccagt gatacatagg agcatgcagg ggggtttggt gggcaatgat     540
gagactgtgg cactcacagc ctttgtgacc atcgcccttc atcatgggct ggccgtcttc     600
caggatgagg gtgcagagcc attgaagcag agagtggaag cctccatctc aaaggcaagc     660
tcatttttgg gggagaaagc aagtgctggg ctcctgggtg cccacgcagc tgccatcacg     720
gcctatgccc tgacactgac caaggcccct gcggacctgc ggggtgttgc ccacaacaac     780
ctcatggcaa tggcccagga gactggagat aacctgtact ggggctcagt cactggttct     840
cagagcaatg ccgtgtcgcc caccccggct cctcgcaacc catccgaccc catgccccag     900
gccccagccc tgtggattga aaccacagcc tacgccctgc tgcacctcct gcttcacgag     960
ggcaaagcag agatggcaga ccaggctgcg gcctggctca cccgtcaggg cagcttccaa    1020
gggggattcc gcagtaccca agacacggtg attgccctgg atgccctgtc tgcctactgg    1080
attgcctccc acaccactga ggagagggt ctcaatgtga ctctcagctc cacaggccgg    1140

<210> SEQ ID NO 4
<211> LENGTH: 380
<212> TYPE: PRT
<213> ORGANISM: Homo sapiens

<400> SEQUENCE: 4

Thr Leu Glu Ile Pro Gly Asn Ser Asp Pro Asn Met Ile Pro Asp Gly
1               5                   10                  15

Asp Phe Asn Ser Tyr Val Arg Val Thr Ala Ser Asp Pro Leu Asp Thr
            20                  25                  30

Leu Gly Ser Glu Gly Ala Leu Ser Pro Gly Gly Val Ala Ser Leu Leu
        35                  40                  45

Arg Leu Pro Arg Gly Cys Gly Glu Gln Thr Met Ile Tyr Leu Ala Pro
    50                  55                  60

Thr Leu Ala Ala Ser Arg Tyr Leu Asp Lys Thr Glu Gln Trp Ser Thr
65                  70                  75                  80
```

```
Leu Pro Pro Glu Thr Lys Asp His Ala Val Asp Leu Ile Gln Lys Gly
                85                  90                  95
Tyr Met Arg Ile Gln Gln Phe Lys Ala Asp Gly Ser Tyr Ala Ala
            100                 105                 110
Trp Leu Ser Arg Gly Ser Ser Thr Trp Leu Thr Ala Phe Val Leu Lys
            115                 120                 125
Val Leu Ser Leu Ala Gln Glu Gln Val Gly Gly Ser Pro Glu Lys Leu
            130                 135                 140
Gln Glu Thr Ser Asn Trp Leu Leu Ser Gln Gln Gln Ala Asp Gly Ser
145                 150                 155                 160
Phe Gln Asp Leu Ser Pro Val Ile His Arg Ser Met Gln Gly Gly Leu
                165                 170                 175
Val Gly Asn Asp Glu Thr Val Ala Leu Thr Ala Phe Val Thr Ile Ala
            180                 185                 190
Leu His His Gly Leu Ala Val Phe Gln Asp Glu Gly Ala Glu Pro Leu
            195                 200                 205
Lys Gln Arg Val Glu Ala Ser Ile Ser Lys Ala Ser Ser Phe Leu Gly
            210                 215                 220
Glu Lys Ala Ser Ala Gly Leu Leu Gly Ala His Ala Ala Ala Ile Thr
225                 230                 235                 240
Ala Tyr Ala Leu Thr Leu Thr Lys Ala Pro Ala Asp Leu Arg Gly Val
                245                 250                 255
Ala His Asn Asn Leu Met Ala Met Ala Gln Gly Thr Gly Asp Asn Leu
            260                 265                 270
Tyr Trp Gly Ser Val Thr Gly Ser Gln Ser Asn Ala Val Ser Pro Thr
            275                 280                 285
Pro Ala Pro Arg Asn Pro Ser Asp Pro Met Pro Gln Ala Pro Ala Leu
            290                 295                 300
Trp Ile Glu Thr Thr Ala Tyr Ala Leu Leu His Leu Leu Leu His Glu
305                 310                 315                 320
Gly Lys Ala Glu Met Ala Asp Gln Ala Ala Ala Trp Leu Thr Arg Gln
                325                 330                 335
Gly Ser Phe Gln Gly Gly Phe Arg Ser Thr Gln Asp Thr Val Ile Ala
            340                 345                 350
Leu Asp Ala Leu Ser Ala Tyr Trp Ile Ala Ser His Thr Thr Glu Glu
            355                 360                 365
Arg Gly Leu Asn Val Thr Leu Ser Ser Thr Gly Arg
            370                 375                 380

<210> SEQ ID NO 5
<211> LENGTH: 2292
<212> TYPE: DNA
<213> ORGANISM: Homo sapiens
<220> FEATURE:
<221> NAME/KEY: source
<222> LOCATION: 1..2292
<223> OTHER INFORMATION: /mol_type="unassigned DNA"
      /organism="Homo sapiens"

<400> SEQUENCE: 5
aacgtgaact tccaaaaggc gattaatgag aaattgggtc agtatgcttc cccgacagcc      60
aagcgctgct gccaggatgg ggtgacacgt ctgcccatga tgcgttcctg cgagcagcgg     120
gcagcccgcg tgcagcagcc ggactgccgg gagcccttcc tgtcctgctg ccaatttgct     180
gagagtctgc gcaagaagag cagggacaag ggccaggcgg cctccaacg agccctggag      240
```

| | |
|---|---|
| atcctgcagg aggaggacct gattgatgag gatgacattc ccgtgcgcag cttcttccca | 300 |
| gagaactggc tctggagagt ggaaacagtg gaccgctttc aaatattgac actgtggctc | 360 |
| cccgactctc tgaccacgtg ggagatccat ggcctgagcc tgtccaaaac caaaggccta | 420 |
| tgtgtggcca ccccagtcca gctccgggtg ttccgcgagt tccacctgca cctccgcctg | 480 |
| cccatgtctc tccgccgctt tgagcagctg gagctgcggc ctgtcctcta taactacctg | 540 |
| gataaaaacc tgactgtgag cgtccacgtg tccccagtgg aggggctgtg cctggctggg | 600 |
| ggcggagggc tggcccagca ggtgctggtg cctgcgggct ctgcccggcc tgttgccttc | 660 |
| tctgtggtgc ccacggcagc cgccgctgtg tctctgaagg tggtggctcg agggtccttc | 720 |
| gaattccctg tgggagatgc ggtgtccaag gttctgcaga ttgagaagga aggggccatc | 780 |
| catagagagg agctggtcta tgaactcaac cccttggacc accgaggccg gaccttggaa | 840 |
| atacctggca actctgatcc caatatgatc cctgatgggg actttaacag ctacgtcagg | 900 |
| gttacagcct cagatccatt ggacacttta ggctctgagg gggccttgtc accaggaggc | 960 |
| gtggcctccc tcttgaggct tcctcgaggc tgtgggggagc aaaccatgat ctacttggct | 1020 |
| ccgacactgg ctgcttcccg ctacctggac aagacagagc agtggagcac actgcctccc | 1080 |
| gagaccaagg accacgccgt ggatctgatc cagaaaggct acatgcggat ccagcagttt | 1140 |
| cggaaggcgg atggttccta tgcggcttgg ttgtcacggg acagcagcac ctggctcaca | 1200 |
| gcctttgtgt tgaaggtcct gagtttggcc caggagcagg taggaggctc gcctgagaaa | 1260 |
| ctgcaggaga catctaactg gcttctgtcc cagcagcagg ctgacggctc gttccaggac | 1320 |
| ccctgtccag tgttagacag gagcatgcag gggggtttgg tgggcaatga tgagactgtg | 1380 |
| gcactcacag cctttgtgac catcgcccTt catcatgggc tggccgtctt ccaggatgag | 1440 |
| ggtgcagagc cattgaagca gagagtggaa gcctccatct caaaggcaaa ctcattttg | 1500 |
| ggggagaaag caagtgctgg gctcctgggt gcccacgcag ctgccatcac ggcctatgcc | 1560 |
| ctgacactga ccaaggcgcc tgtggacctg ctcggtgttg cccacaacaa cctcatggca | 1620 |
| atggcccagg agactggaga taacctgtac tggggctcag tcactggttc tcagagcaat | 1680 |
| gccgtgtcgc ccaccccggc tcctcgcaac ccatccgacc ccatgcccca ggccccagcc | 1740 |
| ctgtggattg aaaccacagc ctacgccctg ctgcacctcc tgcttcacga gggcaaagca | 1800 |
| gagatggcag accaggcttc ggcctggctc acccgtcagg gcagcttcca aggggggattc | 1860 |
| cgcagtaccc aagacacggt gattgccctg gatgccctgt ctgcctactg gattgcctcc | 1920 |
| cacaccactg aggagagggg tctcaatgtg actctcagct ccacaggccg gaatgggttc | 1980 |
| aagtcccacg cgctgcagct gaacaaccgc cagattcgcg gcctggagga ggagctgcag | 2040 |
| ttttccttgg gcagcaagat caatgtgaag gtgggaggaa acagcaaagg aaccctgaag | 2100 |
| gtccttcgta cctacaatgt cctggacatg aagaacacga cctgccagga cctacagata | 2160 |
| gaagtgacag tcaaaggcca cgtcgagtac acgatggaag caaacgagga ctatgaggac | 2220 |
| tatgagtacg atgagcttcc agccaaggat gacccagatg cccctctgca gcccgtgaca | 2280 |
| cccctgcagc tg | 2292 |

<210> SEQ ID NO 6
<211> LENGTH: 764
<212> TYPE: PRT
<213> ORGANISM: Homo sapiens

<400> SEQUENCE: 6

```
Asn Val Asn Phe Gln Lys Ala Ile Asn Glu Lys Leu Gly Gln Tyr Ala
1               5                   10                  15

Ser Pro Thr Ala Lys Arg Cys Cys Gln Asp Gly Val Thr Arg Leu Pro
            20                  25                  30

Met Met Arg Ser Cys Glu Gln Arg Ala Ala Arg Val Gln Gln Pro Asp
        35                  40                  45

Cys Arg Glu Pro Phe Leu Ser Cys Cys Gln Phe Ala Glu Ser Leu Arg
    50                  55                  60

Lys Lys Ser Arg Asp Lys Gly Gln Ala Gly Leu Gln Arg Ala Leu Glu
65                  70                  75                  80

Ile Leu Gln Glu Glu Asp Leu Ile Asp Glu Asp Ile Pro Val Arg
                85                  90                  95

Ser Phe Phe Pro Glu Asn Trp Leu Trp Arg Val Glu Thr Val Asp Arg
            100                 105                 110

Phe Gln Ile Leu Thr Leu Trp Leu Pro Asp Ser Leu Thr Thr Trp Glu
        115                 120                 125

Ile His Gly Leu Ser Leu Ser Lys Thr Lys Gly Leu Cys Val Ala Thr
    130                 135                 140

Pro Val Gln Leu Arg Val Phe Arg Glu Phe His Leu His Leu Arg Leu
145                 150                 155                 160

Pro Met Ser Val Arg Arg Phe Glu Gln Leu Glu Leu Arg Pro Val Leu
                165                 170                 175

Tyr Asn Tyr Leu Asp Lys Asn Leu Thr Val Ser Val His Val Ser Pro
            180                 185                 190

Val Glu Gly Leu Cys Leu Ala Gly Gly Gly Gly Leu Ala Gln Gln Val
        195                 200                 205

Leu Val Pro Ala Gly Ser Ala Arg Pro Val Ala Phe Ser Val Val Pro
    210                 215                 220

Thr Ala Ala Ala Val Ser Leu Lys Val Val Ala Arg Gly Ser Phe
225                 230                 235                 240

Glu Phe Pro Val Gly Asp Ala Val Ser Lys Val Leu Gln Ile Glu Lys
                245                 250                 255

Glu Gly Ala Ile His Arg Glu Glu Leu Val Tyr Glu Leu Asn Pro Leu
            260                 265                 270

Asp His Arg Gly Arg Thr Leu Glu Ile Pro Gly Asn Ser Asp Pro Asn
        275                 280                 285

Met Ile Pro Asp Gly Asp Phe Asn Ser Tyr Val Arg Val Thr Ala Ser
    290                 295                 300

Asp Pro Leu Asp Thr Leu Gly Ser Glu Gly Ala Leu Ser Pro Gly Gly
305                 310                 315                 320

Val Ala Ser Leu Leu Arg Leu Pro Arg Gly Cys Gly Glu Gln Thr Met
                325                 330                 335

Ile Tyr Leu Ala Pro Thr Leu Ala Ala Ser Arg Tyr Leu Asp Lys Thr
            340                 345                 350

Glu Gln Trp Ser Thr Leu Pro Pro Glu Thr Lys Asp His Ala Val Asp
        355                 360                 365

Leu Ile Gln Lys Gly Tyr Met Arg Ile Gln Gln Phe Arg Lys Ala Asp
    370                 375                 380

Gly Ser Tyr Ala Ala Trp Leu Ser Arg Asp Ser Ser Thr Trp Leu Thr
385                 390                 395                 400

Ala Phe Val Leu Lys Val Leu Ser Leu Ala Gln Glu Gln Val Gly Gly
                405                 410                 415
```

-continued

```
Ser Pro Glu Lys Leu Gln Glu Thr Ser Asn Trp Leu Leu Ser Gln Gln
                420                 425                 430

Gln Ala Asp Gly Ser Phe Gln Asp Pro Cys Pro Val Leu Asp Arg Ser
            435                 440                 445

Met Gln Gly Gly Leu Val Gly Asn Asp Glu Thr Val Ala Leu Thr Ala
450                 455                 460

Phe Val Thr Ile Ala Leu His His Gly Leu Ala Val Phe Gln Asp Glu
465                 470                 475                 480

Gly Ala Glu Pro Leu Lys Gln Arg Val Glu Ala Ser Ile Ser Lys Ala
                485                 490                 495

Asn Ser Phe Leu Gly Glu Lys Ala Ser Ala Gly Leu Leu Gly Ala His
            500                 505                 510

Ala Ala Ala Ile Thr Ala Tyr Ala Leu Thr Leu Thr Lys Ala Pro Val
        515                 520                 525

Asp Leu Leu Gly Val Ala His Asn Asn Leu Met Ala Met Ala Gln Glu
    530                 535                 540

Thr Gly Asp Asn Leu Tyr Trp Gly Ser Val Thr Gly Ser Gln Ser Asn
545                 550                 555                 560

Ala Val Ser Pro Thr Pro Ala Pro Arg Asn Pro Ser Asp Pro Met Pro
                565                 570                 575

Gln Ala Pro Ala Leu Trp Ile Glu Thr Thr Ala Tyr Ala Leu Leu His
            580                 585                 590

Leu Leu Leu His Glu Gly Lys Ala Glu Met Ala Asp Gln Ala Ser Ala
        595                 600                 605

Trp Leu Thr Arg Gln Gly Ser Phe Gln Gly Gly Phe Arg Ser Thr Gln
    610                 615                 620

Asp Thr Val Ile Ala Leu Asp Ala Leu Ser Ala Tyr Trp Ile Ala Ser
625                 630                 635                 640

His Thr Thr Glu Glu Arg Gly Leu Asn Val Thr Leu Ser Ser Thr Gly
                645                 650                 655

Arg Asn Gly Phe Lys Ser His Ala Leu Gln Leu Asn Asn Arg Gln Ile
            660                 665                 670

Arg Gly Leu Glu Glu Glu Leu Gln Phe Ser Leu Gly Ser Lys Ile Asn
        675                 680                 685

Val Lys Val Gly Gly Asn Ser Lys Gly Thr Leu Lys Val Leu Arg Thr
    690                 695                 700

Tyr Asn Val Leu Asp Met Lys Asn Thr Thr Cys Gln Asp Leu Gln Ile
705                 710                 715                 720

Glu Val Thr Val Lys Gly His Val Glu Tyr Thr Met Glu Ala Asn Glu
                725                 730                 735

Asp Tyr Glu Asp Tyr Glu Tyr Asp Glu Leu Pro Ala Lys Asp Asp Pro
            740                 745                 750

Asp Ala Pro Leu Gln Pro Val Thr Pro Leu Gln Leu
        755                 760

<210> SEQ ID NO 7
<211> LENGTH: 2292
<212> TYPE: DNA
<213> ORGANISM: Homo sapiens
<220> FEATURE:
<221> NAME/KEY: source
<222> LOCATION: 1..2292
<223> OTHER INFORMATION: /mol_type="unassigned DNA"
      /organism="Homo sapiens"
```

<400> SEQUENCE: 7

```
aacgtgaact tccaaaaggc gattaatgag aaattgggtc agtatgcttc cccgacagcc      60
aagcgctgct gccaggatgg ggtgacacgt ctgcccatga tgcgttcctg cgagcagcgg     120
gcagcccgcg tgcagcagcc ggactgccgg gagcccttcc tgtcctgctg ccaatttgct     180
gagagtctgc gcaagaagag cagggacaag ggccaggcgg gcctccaacg agccctggag     240
atcctgcagg aggaggacct gattgatgag gatgacattc ccgtgcgcag cttcttccca     300
gagaactggc tctggagagt ggaaacagtg gaccgctttc aaatattgac actgtggctc     360
cccgactctc tgaccacgtg ggagatccat ggcctgagcc tgtccaaaac caaaggccta     420
tgtgtggcca ccccagtcca gctccgggtg ttccgcgagt tccacctgca cctccgcctg     480
cccatgtctg tccgccgctt tgagcagctg gagctgcggc ctgtcctcta taactacctg     540
gataaaaacc tgactgtgag cgtccacgtg tccccagtgg aggggctgtg cctggctggg     600
ggcggagggc tggcccagca ggtgctggtg cctgcgggct ctgcccggcc tgttgccttc     660
tctgtggtgc ccacggcagc caccgctgtg tctctgaagg tggtggctcg agggtccttc     720
gaattccctg tgggagatgc ggtgtccaag gttctgcaga ttgagaagga aggggccatc     780
catagagagg agctggtcta tgaactcaac cccttggacc accgaggccg gaccttggaa     840
atacctggca actctgatcc caatatgatc cctgatgggg actttaacag ctacgtcagg     900
gttacagcct cagatccatt ggacacttta ggctctgagg gggccttgtc accaggaggc     960
gtggcctccc tcttgaggct tcctcgaggc tgtggggagc aaaccatgat ctacttggct    1020
ccgacactgg ctgcttcccg ctacctggac aagacagagc agtggagcac actgcctccc    1080
gagaccaagg accacgccgt ggatctgatc cagaaaggct acatgcggat ccagcagttt    1140
cggaaggcgg atggttccta tgcggcttgg ttgtcacggg gcagcagcac ctggctcaca    1200
gcctttgtgt tgaaggtcct gagtttggcc caggagcagg taggaggctc gcctgagaaa    1260
ctgcaggaga catctaactg gcttctgtcc cagcagcagg ctgacggctc gttccaggac    1320
ctctctccag tgatacatag gagcatgcag gggggtttgg tgggcaatga tgagactgtg    1380
gcactcacag ccttttgtgac catcgcccctt catcatgggc tggccgtctt ccaggatgag    1440
ggtgcagagc cattgaagca gagagtggaa gcctccatct caaaggcaag ctcattttg    1500
ggggagaaag caagtgctgg gctcctgggt gcccacgcag ctgccatcac ggcctatgcc    1560
ctgacactga ccaaggcccc tgcggacctg cggggtgttg cccacaacaa cctcatggca    1620
atggcccagg agactggaga taacctgtac tggggctcag tcactggttc tcagagcaat    1680
gccgtgtcgc ccaccccggc tcctcgcaac ccatccgacc ccatgcccca ggccccagcc    1740
ctgtggattg aaaccacagc ctacgccctg ctgcacctcc tgcttcacga gggcaaagca    1800
gagatggcag accaggctgc ggcctggctc acccgtcagg gcagcttcca aggggattc    1860
cgcagtaccc aagacacggt gattgccctg gatgccctgt ctgcctactg gattgcctcc    1920
cacaccactg aggagagggg tctcaatgtg actctcagct ccacaggccg gaatgggttc    1980
aagtcccacg cgctgcagct gaacaaccgc cagattcgcg gcctggagga ggagctgcag    2040
ttttccttgg gcagcaagat caatgtgaag gtggaggaa acagcaaagg aacccctgaag    2100
gtccttcgta cctacaatgt cctggacatg aagaacacga cctgccagga cctacagata    2160
gaagtgacag tcaaaggcca cgtcgagtac acgatggaag caaacgagga ctatgaggac    2220
tatgagtacg atgagcttcc agccaaggat gacccagatg cccctctgca gcccgtgaca    2280
cccctgcagc tg                                                         2292
```

-continued

```
<210> SEQ ID NO 8
<211> LENGTH: 764
<212> TYPE: PRT
<213> ORGANISM: Homo sapiens

<400> SEQUENCE: 8

Asn Val Asn Phe Gln Lys Ala Ile Asn Glu Lys Leu Gly Gln Tyr Ala
1               5                   10                  15

Ser Pro Thr Ala Lys Arg Cys Cys Gln Asp Gly Val Thr Arg Leu Pro
            20                  25                  30

Met Met Arg Ser Cys Glu Gln Arg Ala Ala Arg Val Gln Gln Pro Asp
        35                  40                  45

Cys Arg Glu Pro Phe Leu Ser Cys Cys Gln Phe Ala Glu Ser Leu Arg
    50                  55                  60

Lys Lys Ser Arg Asp Lys Gly Gln Ala Gly Leu Gln Arg Ala Leu Glu
65                  70                  75                  80

Ile Leu Gln Glu Glu Asp Leu Ile Asp Glu Asp Ile Pro Val Arg
                85                  90                  95

Ser Phe Phe Pro Glu Asn Trp Leu Trp Arg Val Glu Thr Val Asp Arg
            100                 105                 110

Phe Gln Ile Leu Thr Leu Trp Leu Pro Asp Ser Leu Thr Thr Trp Glu
        115                 120                 125

Ile His Gly Leu Ser Leu Ser Lys Thr Lys Gly Leu Cys Val Ala Thr
    130                 135                 140

Pro Val Gln Leu Arg Val Phe Arg Glu Phe His Leu His Leu Arg Leu
145                 150                 155                 160

Pro Met Ser Val Arg Arg Phe Glu Gln Leu Glu Leu Arg Pro Val Leu
                165                 170                 175

Tyr Asn Tyr Leu Asp Lys Asn Leu Thr Val Ser Val His Val Ser Pro
            180                 185                 190

Val Glu Gly Leu Cys Leu Ala Gly Gly Gly Gly Leu Ala Gln Gln Val
        195                 200                 205

Leu Val Pro Ala Gly Ser Ala Arg Pro Val Ala Phe Ser Val Val Pro
    210                 215                 220

Thr Ala Ala Thr Ala Val Ser Leu Lys Val Val Ala Arg Gly Ser Phe
225                 230                 235                 240

Glu Phe Pro Val Gly Asp Ala Val Ser Lys Val Leu Gln Ile Glu Lys
                245                 250                 255

Glu Gly Ala Ile His Arg Glu Glu Leu Val Tyr Glu Leu Asn Pro Leu
            260                 265                 270

Asp His Arg Gly Arg Thr Leu Glu Ile Pro Gly Asn Ser Asp Pro Asn
        275                 280                 285

Met Ile Pro Asp Gly Asp Phe Asn Ser Tyr Val Arg Val Thr Ala Ser
    290                 295                 300

Asp Pro Leu Asp Thr Leu Gly Ser Glu Gly Ala Leu Ser Pro Gly Gly
305                 310                 315                 320

Val Ala Ser Leu Leu Arg Leu Pro Arg Gly Cys Gly Glu Gln Thr Met
                325                 330                 335

Ile Tyr Leu Ala Pro Thr Leu Ala Ala Ser Arg Tyr Leu Asp Lys Thr
            340                 345                 350

Glu Gln Trp Ser Thr Leu Pro Pro Glu Thr Lys Asp His Ala Val Asp
        355                 360                 365

Leu Ile Gln Lys Gly Tyr Met Arg Ile Gln Gln Phe Arg Lys Ala Asp
    370                 375                 380
```

Gly Ser Tyr Ala Ala Trp Leu Ser Arg Gly Ser Ser Thr Trp Leu Thr
385                 390                 395                 400

Ala Phe Val Leu Lys Val Leu Ser Leu Ala Gln Glu Gln Val Gly Gly
            405                 410                 415

Ser Pro Glu Lys Leu Gln Glu Thr Ser Asn Trp Leu Ser Gln Gln
            420                 425                 430

Gln Ala Asp Gly Ser Phe Gln Asp Leu Ser Pro Val Ile His Arg Ser
            435                 440                 445

Met Gln Gly Gly Leu Val Gly Asn Asp Glu Thr Val Ala Leu Thr Ala
    450                 455                 460

Phe Val Thr Ile Ala Leu His His Gly Leu Ala Val Phe Gln Asp Glu
465                 470                 475                 480

Gly Ala Glu Pro Leu Lys Gln Arg Val Glu Ala Ser Ile Ser Lys Ala
            485                 490                 495

Ser Ser Phe Leu Gly Glu Lys Ala Ser Ala Gly Leu Leu Gly Ala His
            500                 505                 510

Ala Ala Ala Ile Thr Ala Tyr Ala Leu Thr Leu Thr Lys Ala Pro Ala
            515                 520                 525

Asp Leu Arg Gly Val Ala His Asn Asn Leu Met Ala Met Ala Gln Glu
530                 535                 540

Thr Gly Asp Asn Leu Tyr Trp Gly Ser Val Thr Gly Ser Gln Ser Asn
545                 550                 555                 560

Ala Val Ser Pro Thr Pro Ala Pro Arg Asn Pro Ser Asp Pro Met Pro
            565                 570                 575

Gln Ala Pro Ala Leu Trp Ile Glu Thr Thr Ala Tyr Ala Leu Leu His
            580                 585                 590

Leu Leu Leu His Glu Gly Lys Ala Glu Met Ala Asp Gln Ala Ala Ala
            595                 600                 605

Trp Leu Thr Arg Gln Gly Ser Phe Gln Gly Gly Phe Arg Ser Thr Gln
            610                 615                 620

Asp Thr Val Ile Ala Leu Asp Ala Leu Ser Ala Tyr Trp Ile Ala Ser
625                 630                 635                 640

His Thr Thr Glu Glu Arg Gly Leu Asn Val Thr Leu Ser Ser Thr Gly
            645                 650                 655

Arg Asn Gly Phe Lys Ser His Ala Leu Gln Leu Asn Asn Arg Gln Ile
            660                 665                 670

Arg Gly Leu Glu Glu Glu Leu Gln Phe Ser Leu Gly Ser Lys Ile Asn
            675                 680                 685

Val Lys Val Gly Gly Asn Ser Lys Gly Thr Leu Lys Val Leu Arg Thr
    690                 695                 700

Tyr Asn Val Leu Asp Met Lys Asn Thr Thr Cys Gln Asp Leu Gln Ile
705                 710                 715                 720

Glu Val Thr Val Lys Gly His Val Glu Tyr Thr Met Glu Ala Asn Glu
            725                 730                 735

Asp Tyr Glu Asp Tyr Glu Tyr Asp Glu Leu Pro Ala Lys Asp Asp Pro
            740                 745                 750

Asp Ala Pro Leu Gln Pro Val Thr Pro Leu Gln Leu
    755                 760

<210> SEQ ID NO 9
<211> LENGTH: 2913
<212> TYPE: DNA
<213> ORGANISM: Homo sapiens

```
<220> FEATURE:
<221> NAME/KEY: source
<222> LOCATION: 1..2913
<223> OTHER INFORMATION: /mol_type="unassigned DNA"
      /organism="Homo sapiens"

<400> SEQUENCE: 9
agtgtcaaga aagaagtcaa cttttcttcc cctacttccc tgcatttctc ctctgtgctc       60
actgccacac gcagctcaac ctggacggca cagccagagg cgagatgctt ctctgctgat      120
ctgagtctgc ctgcagcatg gacctgggtc ttccctgaag catctccagg gctggaggga      180
cgactgccat gcaccgaggg ctcatccatc cgcagagcag ggcagtggga ggagacgcca      240 tgaccccat cgtcacagtc ctgatctgtc tcgggctgag tctgggcccc aggacccacg       300
tgcagacagg gaccattccc aagcccaccc tgtgggctga ccagactct gtgatcaccc        360 aggggagtcc cgtcacccct cagttgtcagg ggagccttga agcccaggag taccgtctat      420
atagggagaa aaaatcagca tcttggatta cacggatacg accagagctt gtgaagaacg      480
gccagttcca catcccatcc atcacctggg aacacacagg gcgatatggc tgtcagtatt      540
acagccgcgc tcggtggtct gagctcagtg acccctggt gctggtgatg acaggagcct       600
acccaaaacc caccctctca gcccagccca gccctgtggt gacctcagga ggaagggtga     660
ccctccagtg tgagtcacag gtggcatttg gcggcttcat tctgtgtaag gaaggagaag     720
aagaacaccc acaatgcctg aactcccagc ccatgcccg tgggtcgtcc cgcgccatct       780
tctccgtggg ccccgtgagc ccgaatcgca ggtggtcgca caggtgctat ggttatgact     840
tgaactctcc ctatgtgtgg tcttcaccca gtgatctcct ggagctcctg gtcccaggtg     900
tttctaagaa gccatcactc tcagtgcagc cgggtcctgt cgtggcccct ggggaaagcc     960 tgacctcca gtgtgtctct gatgtcggct atgacagatt tgttctgtac aaggaggggg   1020
aacgtgacct tcgccagctc cctggccggc agcccaggc tgggctctcc caggccaact   1080
tcaccctggg ccctgtgagc cgctcctacg ggggccagta cagatgctac ggtgcacaca   1140
acctctcctc tgagtgctcg gccccagcg acccctgga catcctgatc acaggacaga    1200
tccgtggcac acccttcatc tcagtgcagc caggccccac agtggcctca ggagagaacg   1260
tgaccctgct gtgtcagtca tggcggcagt tccacacttt ccttctgacc aaggcgggag   1320
cagctgatgc cccactccgt ctaagatcaa tacacgaata tcctaagtac caggctgaat   1380
tccccatgag tcctgtgacc tcagcccacg cggggaccta caggtgctac ggctcactca   1440
actccgaccc ctacctgctg tctcacccca gtgagcccct ggagctcgtg gtctcaggac   1500
cctccatggg ttccagcccc ccaccaccg gtccatctc cacacctgca ggccctgagg    1560
accagcccct caccccact gggtcggatc cccaaagtgg tctgggaagg cacctggggg   1620
ttgtgatcgg catcttggtg gccgtcgtcc tactgctcct cctcctcctc ctcctcttcc   1680
tcatcctccg acatcgacgt caaggcaaac actggacatc gacccagaga aaggctgatt   1740
tccaacatcc tgcaggggct gtggggccag agccacagaa cagaggcctg cagtggaggt   1800
ccagcccagc tgccgacgcc caggaagaaa acctctatgc tgccgtgaag gacacacagc   1860
ctgaagatgg ggtggagatg gacactcggg ctgctgcatc tgaagccccc caggatgtga   1920
cctacgccca gctgcacagc ttgacccta gacggaaggc aactgagcct cctccatccc   1980
aggaaaggga acctccagct gagcccagca tctacgccac cctggccatc cactagcccg   2040
gagggtacgc agactccaca ctcagtagaa ggagactcag gactgctgaa ggcacggag    2100 ctgccccag tggacaccaa tgaaccccag tcagcctgga cccctaacaa agaccatgag   2160
```

-continued

```
gagatgctgg gaactttggg actcacttga ttctgcagtc gaaataacta atatccctac    2220
attttttaat taaagcaaca gacttctcaa taatcaatga gttaaccgag aaaactaaaa    2280
tcagaagtaa gaatgtgctt taaactgaat cacaatataa atattacaca tcacacaatg    2340
aaattgaaaa agtacaaacc acaaatgaaa aaagtagaaa cgaaaaaaaa aaactaggaa    2400
atgaatgacg ttggctttcg tataaggaat ttagaaaaag aataaccaat tattccaaat    2460
gaaggtgtaa gaaagggaat aagaagaaga agagttgctc atgaggaaaa accaaaactt    2520
gaaaattcaa caaagccaat gaagctcatt cttgaaaata ttaattacag tcataaatcc    2580 taactcacatt gagcaagaga aagaaagagc aggcacgcat ttccatatgg gagtgagcca    2640
gcagacagcc cagcagatcc tacacacatt ttcacaaact aaccccagaa caggctgcaa    2700
acctatacca atatactaga aaatgcagat taaatggatg aaatattcaa aactggagtt    2760
tacataatga acgtaagagt aatcagagaa tctgactcat tttaaatgtg tgtgtatgtg    2820
tgtgtatata tatgtgtgtg tgtgtgtgtg tgtgtgtgtg tgaaaaacat tgactgtaat    2880
aaaaatgttc ccatcgtaaa aaaaaaaaa aaa                                  2913
```

<210> SEQ ID NO 10
<211> LENGTH: 598
<212> TYPE: PRT
<213> ORGANISM: Homo sapiens

<400> SEQUENCE: 10

```
Met Thr Pro Ile Val Thr Val Leu Ile Cys Leu Gly Leu Ser Leu Gly
1               5                   10                  15

Pro Arg Thr His Val Gln Thr Gly Thr Ile Pro Lys Pro Thr Leu Trp
            20                  25                  30

Ala Glu Pro Asp Ser Val Ile Thr Gln Gly Ser Pro Val Thr Leu Ser
        35                  40                  45

Cys Gln Gly Ser Leu Glu Ala Gln Glu Tyr Arg Leu Tyr Arg Glu Lys
    50                  55                  60

Lys Ser Ala Ser Trp Ile Thr Arg Ile Arg Pro Glu Leu Val Lys Asn
65                  70                  75                  80

Gly Gln Phe His Ile Pro Ser Ile Thr Trp Glu His Thr Gly Arg Tyr
                85                  90                  95

Gly Cys Gln Tyr Tyr Ser Arg Ala Arg Trp Ser Glu Leu Ser Asp Pro
            100                 105                 110

Leu Val Leu Val Met Thr Gly Ala Tyr Pro Lys Pro Thr Leu Ser Ala
        115                 120                 125

Gln Pro Ser Pro Val Val Thr Ser Gly Gly Arg Val Thr Leu Gln Cys
    130                 135                 140

Glu Ser Gln Val Ala Phe Gly Gly Phe Ile Leu Cys Lys Glu Gly Glu
145                 150                 155                 160

Glu Glu His Pro Gln Cys Leu Asn Ser Gln Pro His Ala Arg Gly Ser
                165                 170                 175

Ser Arg Ala Ile Phe Ser Val Gly Pro Val Ser Pro Asn Arg Arg Trp
            180                 185                 190

Ser His Arg Cys Tyr Gly Tyr Asp Leu Asn Ser Pro Tyr Val Trp Ser
        195                 200                 205

Ser Pro Ser Asp Leu Leu Glu Leu Leu Val Pro Gly Val Ser Lys Lys
    210                 215                 220

Pro Ser Leu Ser Val Gln Pro Gly Pro Val Val Ala Pro Gly Glu Ser
225                 230                 235                 240
```

```
Leu Thr Leu Gln Cys Val Ser Asp Val Gly Tyr Asp Arg Phe Val Leu
                245                 250                 255

Tyr Lys Glu Gly Glu Arg Asp Leu Arg Gln Leu Pro Gly Arg Gln Pro
            260                 265                 270

Gln Ala Gly Leu Ser Gln Ala Asn Phe Thr Leu Gly Pro Val Ser Arg
        275                 280                 285

Ser Tyr Gly Gly Gln Tyr Arg Cys Tyr Gly Ala His Asn Leu Ser Ser
    290                 295                 300

Glu Cys Ser Ala Pro Ser Asp Pro Leu Asp Ile Leu Ile Thr Gly Gln
305                 310                 315                 320

Ile Arg Gly Thr Pro Phe Ile Ser Val Gln Pro Gly Pro Thr Val Ala
                325                 330                 335

Ser Gly Glu Asn Val Thr Leu Leu Cys Gln Ser Trp Arg Gln Phe His
            340                 345                 350

Thr Phe Leu Leu Thr Lys Ala Gly Ala Ala Asp Ala Pro Leu Arg Leu
        355                 360                 365

Arg Ser Ile His Glu Tyr Pro Lys Tyr Gln Ala Glu Phe Pro Met Ser
    370                 375                 380

Pro Val Thr Ser Ala His Ala Gly Thr Tyr Arg Cys Tyr Gly Ser Leu
385                 390                 395                 400

Asn Ser Asp Pro Tyr Leu Leu Ser His Pro Ser Glu Pro Leu Glu Leu
                405                 410                 415

Val Val Ser Gly Pro Ser Met Gly Ser Ser Pro Pro Thr Gly Pro
            420                 425                 430

Ile Ser Thr Pro Ala Gly Pro Glu Asp Gln Pro Leu Thr Pro Thr Gly
        435                 440                 445

Ser Asp Pro Gln Ser Gly Leu Gly Arg His Leu Gly Val Val Ile Gly
    450                 455                 460

Ile Leu Val Ala Val Val Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
            500                 505                 510

Thr Asp Arg Gly Leu Gln Trp Arg Ser Ser Pro Ala Ala Asp Ala Gln
        515                 520                 525

Glu Glu Asn Leu Tyr Ala Ala Val Lys Asp Thr Gln Pro Glu Asp Gly
    530                 535                 540

Val Glu Met Asp Thr Arg Ala Ala Ala Ser Glu Ala Pro Gln Asp Val
545                 550                 555                 560

Thr Tyr Ala Gln Leu His Ser Leu Thr Leu Arg Arg Lys Ala Thr Glu
                565                 570                 575

Pro Pro Pro Ser Gln Glu Arg Glu Pro Pro Ala Glu Pro Ser Ile Tyr
            580                 585                 590

Ala Thr Leu Ala Ile His
        595

<210> SEQ ID NO 11
<211> LENGTH: 12
<212> TYPE: DNA
<213> ORGANISM: Artificial Sequence
```

```
<220> FEATURE:
<221> NAME/KEY: source
<222> LOCATION: 1..12
<223> OTHER INFORMATION: /mol_type="unassigned DNA"
      /note="Linker"
      /organism="Artificial Sequence"

<400> SEQUENCE: 11
gggsgggsgg gs                                                             12

<210> SEQ ID NO 12
<211> LENGTH: 643
<212> TYPE: PRT
<213> ORGANISM: Artificial Sequence
<220> FEATURE:
<223> OTHER INFORMATION: C4Ad-Immunoglobulin G1 fusion protein

<400> SEQUENCE: 12
```

Met Pro Met Gly Ser Leu Gln Pro Leu Ala Thr Leu Tyr Leu Leu Gly
1               5                   10                  15

Met Leu Val Ala Ser Cys Leu Gly Thr Leu Glu Ile Pro Gly Asn Ser
            20                  25                  30

Asp Pro Asn Met Ile Pro Asp Gly Asp Phe Asn Ser Tyr Val Arg Val
        35                  40                  45

Thr Ala Ser Asp Pro Leu Asp Thr Leu Gly Ser Glu Gly Ala Leu Ser
    50                  55                  60

Pro Gly Gly Val Ala Ser Leu Arg Leu Pro Arg Gly Cys Gly Glu
65                  70                  75                  80

Gln Thr Met Ile Tyr Leu Ala Pro Thr Leu Ala Ala Ser Arg Tyr Leu
                85                  90                  95

Asp Lys Thr Glu Gln Trp Ser Thr Leu Pro Pro Glu Thr Lys Asp His
            100                 105                 110

Ala Val Asp Leu Ile Gln Lys Gly Tyr Met Arg Ile Gln Gln Phe Arg
        115                 120                 125

Lys Ala Asp Gly Ser Tyr Ala Ala Trp Leu Ser Arg Asp Ser Ser Thr
    130                 135                 140

Trp Leu Thr Ala Phe Val Leu Lys Val Leu Ser Leu Ala Gln Glu Gln
145                 150                 155                 160

Val Gly Gly Ser Pro Glu Lys Leu Gln Glu Thr Ser Asn Trp Leu Leu
                165                 170                 175

Ser Gln Gln Gln Ala Asp Gly Ser Phe Gln Asp Pro Cys Pro Val Leu
            180                 185                 190

Asp Arg Ser Met Gln Gly Gly Leu Val Gly Asn Asp Glu Thr Val Ala
        195                 200                 205

Leu Thr Ala Phe Val Thr Ile Ala Leu His His Gly Leu Ala Val Phe
    210                 215                 220

Gln Asp Glu Gly Ala Glu Pro Leu Lys Gln Arg Val Glu Ala Ser Ile
225                 230                 235                 240

Ser Lys Ala Asn Ser Phe Leu Gly Glu Lys Ala Ser Ala Gly Leu Leu
                245                 250                 255

Gly Ala His Ala Ala Ala Ile Thr Ala Tyr Ala Leu Thr Leu Thr Lys
            260                 265                 270

Ala Pro Val Asp Leu Leu Gly Val Ala His Asn Asn Leu Met Ala Met
        275                 280                 285

Ala Gln Glu Thr Gly Asp Asn Leu Tyr Trp Gly Ser Val Thr Gly Ser
    290                 295                 300

```
Gln Ser Asn Ala Val Ser Pro Thr Pro Ala Pro Arg Asn Pro Ser Asp
305                 310                 315                 320

Pro Met Pro Gln Ala Pro Ala Leu Trp Ile Glu Thr Thr Ala Tyr Ala
            325                 330                 335

Leu Leu His Leu Leu His Glu Gly Lys Ala Glu Met Ala Asp Gln
        340                 345                 350

Ala Ala Ala Trp Leu Thr Arg Gln Gly Ser Phe Gln Gly Phe Arg
        355                 360                 365

Ser Thr Gln Asp Thr Val Ile Ala Leu Asp Ala Leu Ser Ala Tyr Trp
    370                 375                 380

Ile Ala Ser His Thr Thr Glu Glu Arg Gly Leu Asn Val Thr Leu Ser
385                 390                 395                 400

Ser Thr Gly Arg Gly Gly Gly Asp Pro Glu Gly Asp Pro Lys Ser Cys
            405                 410                 415

Asp Lys Thr His Thr Cys Pro Pro Cys Pro Ala Pro Glu Leu Leu Gly
            420                 425                 430

Gly Pro Ser Val Phe Leu Phe Pro Pro Lys Pro Lys Asp Thr Leu Met
            435                 440                 445

Ile Ser Arg Thr Pro Glu Val Thr Cys Val Val Val Asp Val Ser His
450                 455                 460

Glu Asp Pro Glu Val Lys Phe Asn Trp Tyr Val Asp Gly Val Glu Val
465                 470                 475                 480

His Asn Ala Lys Thr Lys Pro Arg Glu Glu Gln Tyr Asn Ser Thr Tyr
            485                 490                 495

Arg Val Val Ser Val Leu Thr Val Leu His Gln Asp Trp Leu Asn Gly
            500                 505                 510

Lys Glu Tyr Lys Cys Lys Val Ser Asn Lys Ala Leu Pro Ala Pro Ile
            515                 520                 525

Glu Lys Thr Ile Ser Lys Ala Lys Gly Gln Pro Arg Glu Pro Gln Val
            530                 535                 540

Tyr Thr Leu Pro Pro Ser Arg Asp Glu Leu Thr Lys Asn Gln Val Ser
545                 550                 555                 560

Leu Thr Cys Leu Val Lys Gly Phe Tyr Pro Ser Asp Ile Ala Val Glu
            565                 570                 575

Trp Glu Ser Asn Gly Gln Pro Glu Asn Asn Tyr Lys Thr Thr Pro Pro
            580                 585                 590

Val Leu Asp Ser Asp Gly Ser Phe Phe Leu Tyr Ser Lys Leu Thr Val
            595                 600                 605

Asp Lys Ser Arg Trp Gln Gln Gly Asn Val Phe Ser Cys Ser Val Met
            610                 615                 620

His Glu Ala Leu His Asn His Tyr Thr Gln Lys Ser Leu Ser Leu Ser
625                 630                 635                 640

Pro Gly Lys

<210> SEQ ID NO 13
<211> LENGTH: 643
<212> TYPE: PRT
<213> ORGANISM: Artificial Sequence
<220> FEATURE:
<223> OTHER INFORMATION: C4Bd-Immunoglobulin G1 fusion protein
```

```
<400> SEQUENCE: 13

Met Pro Met Gly Ser Leu Gln Pro Leu Ala Thr Leu Tyr Leu Leu Gly
1               5                   10                  15

Met Leu Val Ala Ser Cys Leu Gly Thr Leu Glu Ile Pro Gly Asn Ser
            20                  25                  30

Asp Pro Asn Met Ile Pro Asp Gly Asp Phe Asn Ser Tyr Val Arg Val
        35                  40                  45

Thr Ala Ser Asp Pro Leu Asp Thr Leu Gly Ser Glu Gly Ala Leu Ser
    50                  55                  60

Pro Gly Gly Val Ala Ser Leu Leu Arg Leu Pro Arg Gly Cys Gly Glu
65                  70                  75                  80

Gln Thr Met Ile Tyr Leu Ala Pro Thr Leu Ala Ala Ser Arg Tyr Leu
                85                  90                  95

Asp Lys Thr Glu Gln Trp Ser Thr Leu Pro Pro Glu Thr Lys Asp His
            100                 105                 110

Ala Val Asp Leu Ile Gln Lys Gly Tyr Met Arg Ile Gln Gln Phe Arg
        115                 120                 125

Lys Ala Asp Gly Ser Tyr Ala Ala Trp Leu Ser Arg Asp Ser Ser Thr
    130                 135                 140

Trp Leu Thr Ala Phe Val Leu Lys Val Leu Ser Leu Ala Gln Glu Gln
145                 150                 155                 160

Val Gly Gly Ser Pro Glu Lys Leu Gln Glu Thr Ser Asn Trp Leu Leu
                165                 170                 175

Ser Gln Gln Gln Ala Asp Gly Ser Phe Gln Asp Leu Ser Pro Val Ile
            180                 185                 190

His Arg Ser Met Gln Gly Gly Leu Val Gly Asn Asp Glu Thr Val Ala
        195                 200                 205

Leu Thr Ala Phe Val Thr Ile Ala Leu His His Gly Leu Ala Val Phe
    210                 215                 220

Gln Asp Glu Gly Ala Glu Pro Leu Lys Gln Arg Val Glu Ala Ser Ile
225                 230                 235                 240

Ser Lys Ala Asn Ser Phe Leu Gly Glu Lys Ala Ser Ala Gly Leu Leu
                245                 250                 255

Gly Ala His Ala Ala Ile Thr Ala Tyr Ala Leu Thr Leu Thr Lys
            260                 265                 270

Ala Pro Val Asp Leu Leu Gly Val Ala His Asn Asn Leu Met Ala Met
        275                 280                 285

Ala Gln Glu Thr Gly Asp Asn Leu Tyr Trp Gly Ser Val Thr Gly Ser
    290                 295                 300

Gln Ser Asn Ala Val Ser Pro Thr Pro Ala Pro Arg Asn Pro Ser Asp
305                 310                 315                 320

Pro Met Pro Gln Ala Pro Ala Leu Trp Ile Glu Thr Thr Ala Tyr Ala
                325                 330                 335

Leu Leu His Leu Leu Leu His Glu Gly Lys Ala Glu Met Ala Asp Gln
            340                 345                 350

Ala Ala Ala Trp Leu Thr Arg Gln Gly Ser Phe Gln Gly Gly Phe Arg
        355                 360                 365

Ser Thr Gln Asp Thr Val Ile Ala Leu Asp Ala Leu Ser Ala Tyr Trp
    370                 375                 380

Ile Ala Ser His Thr Thr Glu Glu Arg Gly Leu Asn Val Thr Leu Ser
385                 390                 395                 400

Ser Thr Gly Arg Gly Gly Gly Asp Pro Glu Gly Asp Pro Lys Ser Cys
                405                 410                 415
```

-continued

```
Asp Lys Thr His Thr Cys Pro Pro Cys Pro Ala Pro Glu Leu Leu Gly
            420             425             430
Gly Pro Ser Val Phe Leu Phe Pro Pro Lys Pro Lys Asp Thr Leu Met
        435             440             445
Ile Ser Arg Thr Pro Glu Val Thr Cys Val Val Val Asp Val Ser His
    450             455             460
Glu Asp Pro Glu Val Lys Phe Asn Trp Tyr Val Asp Gly Val Glu Val
465             470             475             480
His Asn Ala Lys Thr Lys Pro Arg Glu Glu Gln Tyr Asn Ser Thr Tyr
            485             490             495
Arg Val Val Ser Val Leu Thr Val Leu His Gln Asp Trp Leu Asn Gly
            500             505             510
Lys Glu Tyr Lys Cys Lys Val Ser Asn Lys Ala Leu Pro Ala Pro Ile
            515             520             525
Glu Lys Thr Ile Ser Lys Ala Lys Gly Gln Pro Arg Glu Pro Gln Val
        530             535             540
Tyr Thr Leu Pro Pro Ser Arg Asp Glu Leu Thr Lys Asn Gln Val Ser
545             550             555             560
Leu Thr Cys Leu Val Lys Gly Phe Tyr Pro Ser Asp Ile Ala Val Glu
            565             570             575
Trp Glu Ser Asn Gly Gln Pro Glu Asn Asn Tyr Lys Thr Thr Pro Pro
            580             585             590
Val Leu Asp Ser Asp Gly Ser Phe Phe Leu Tyr Ser Lys Leu Thr Val
            595             600             605
Asp Lys Ser Arg Trp Gln Gln Gly Asn Val Phe Ser Cys Ser Val Met
        610             615             620
His Glu Ala Leu His Asn His Tyr Thr Gln Lys Ser Leu Ser Leu Ser
625             630             635             640
Pro Gly Lys
```